United States Patent
Zaharevitz et al.

(10) Patent No.: US 6,610,684 B2
(45) Date of Patent: Aug. 26, 2003

(54) FUSED AZEPINONE CYCLIN DEPENDENT KINASE INHIBITORS

(75) Inventors: Daniel W. Zaharevitz, Camp Springs, MD (US); Rick P. Gussio, Frederick, MD (US); Ravi K. Jalluri, San Diego, CA (US); Edward A. Sausville, Silver Spring, MD (US); Conrad Kunick, Hamburg (DE); Laurent Meijer, Roscoff (FR)

(73) Assignees: The United States of America as represented by the Department of Health and Human Services, Washington, DC (US); Centre National de la Recherche Scientifique (FR)

( * ) Notice: Subject to any disclaimer, the term of this patent is extended or adjusted under 35 U.S.C. 154(b) by 0 days.

(21) Appl. No.: 09/739,534

(22) Filed: Dec. 14, 2000

(65) Prior Publication Data

US 2002/0042412 A1 Apr. 11, 2002

Related U.S. Application Data

(63) Continuation-in-part of application No. PCT/US99/13577, filed on Jun. 16, 1999.
(60) Provisional application No. 60/089,619, filed on Jun. 16, 1998.

(51) Int. Cl.$^7$ .................. C07D 487/04; C07D 495/14; A61K 31/55
(52) U.S. Cl. .................. 514/212.06; 540/521
(58) Field of Search ....... 540/521; 514/212.06

(56) References Cited

FOREIGN PATENT DOCUMENTS

DE          2051 230         4/1971

OTHER PUBLICATIONS

Kunick, C., "Synthese von 7,12–Dihydro–indolo[3,2–d][1]benzazepin–6–(5H)–onen und 6,11–Dihydro–thieno–[3',2':2,3]azepino[4,5–b]indol–5(4H)–on," *Arch. Pharm.*, 325:297–299 (1992).

Zaharevitz, D.W. et al., "Discovery and Initial Characterization of the Paullones, a Novel Class of Small–Molecule Inhibitors of Cyclin–dependent Kinases," *Cancer Research*, 59:2566–2569 (Jun. 1, 1999).

Kozikowski, A.P. et al., "Chemistry, Binding Affinities, and Behavioral Properties of a New Class of 'Antineophobic' Mitochondrial DBI Receptor Complex (mDRC) Ligands," *J. Med. Chem.*, 36:2908–2920 (1993).

Kozikowski, A.P. et al., "Synthese von (2–Arylindol–3–yl) acetamiden als Sonden zur Untersuchung der mitochondrialen Steroidbildung—ein neuer Mechanismus fur die GABA–Rezeptormodulation," *Angewandte Chemie*, 104:1092–1094 (1992).

Sedlacek, H.H. et al., "Flavopiridol (L86 8275; NSC 649890), A New Kinase Inhibitor for Tumor Therapy," *Int. J. Oncology*, 9:1143–1168 (1996).

Brooks, E.E. et al., "CVT–313, a Specific and Potent Inhibitor of CDK2 That Prevents Neointimal Proliferation," *J. Biol. Chem.*, 272:29207–29211 (Nov. 14, 1997).

International Search Report for PCT Application US99/13579 (Oct. 29, 1999).

*Primary Examiner*—Bruck Kifle
(74) *Attorney, Agent, or Firm*—Klarquist Sparkman, LLP

(57) ABSTRACT

A new class of cyclin dependent kinase inhibitors that also have antiproliferative activity in human tumor cell line assays are described. Most of these compounds satisfy the formula

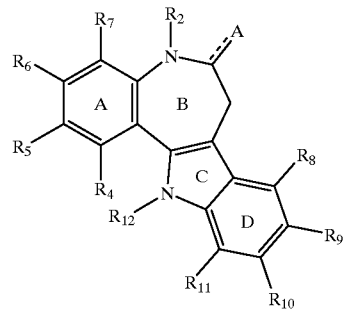

wherein A is oxygen or sulfur coupled to the right by a single or double bond; $R_2$ is selected from the group consisting of hydrogen, aryl, lower aliphatic substituents, particularly alkyl and lower alkyl ester; $R_4$–$R_7$ are independently selected from the group consisting of alkoxy, amino, acyl, aliphatic substituents, particularly alkyl, alkenyl and alkinyl substituents, aliphatic alcohols, particularly alkyl alcohols, aliphatic nitriles, particularly alkyl nitriles, cyano, nitro, carboxyl, halogen, hydrogen, hydroxyl, imino, and α, β, unsaturated ketones; $R_8$–$R_{11}$ are independently selected from the group consisting of aliphatic substituents, particularly alkyl, alkenyl and alkinyl substituents, particularly lower aliphatic substituents, alipahatic alcohols, particularly alkyl alcohols, alkoxy, acyl, cyano, nitro, epoxy, haloalkyl groups, halogen, hydrogen and hydroxyl; $R_{12}$ is selected from the group consisting of aliphatic groups, particularly lower alkyl groups, aliphatic alcohols, particularly alkyl alcohols, carboxylic acids and hydrogen. Compositions comprising effective amounts of such compounds also are described. These compounds and compositions can be used in a method for inhibiting the proliferation of living cells in a subject comprising administering an effective amount of the compound(s), or composition(s) comprising the compound(s), to a subject to inhibit the proliferation of living cells, such as neoplastic cells.

39 Claims, 12 Drawing Sheets

FIG. 1B

| Panel/Cell Line | Log₁₀ LC50 | LC50 |
|---|---|---|
| Leukemia | | |
| CCRF-CEM | -4.30 | |
| HL-60(TB) | -4.30 | |
| K-562 | -4.30 | |
| MOLT-4 | -4.30 | |
| RPMI-8226 | -4.30 | |
| SR | -4.30 | |
| Non-Small Cell Lung Cancer | | |
| A549/ATCC | -4.30 | |
| EKVX | -4.30 | |
| HOP-62 | -4.30 | |
| HOP-92 | -4.30 | |
| NCI-H226 | -4.30 | |
| NCI-H23 | -4.30 | |
| NCI-H322M | -4.30 | |
| NCI-H460 | -4.30 | |
| NCI-H522 | -4.30 | |
| Colon Cancer | | |
| COLO 205 | -4.30 | |
| HCC-2998 | -4.30 | |
| HCT-116 | -4.30 | |
| HCT-15 | -4.30 | |
| HT29 | -4.30 | |
| KM12 | -4.30 | |
| SW-620 | -4.30 | |
| CNS Cancer | | |
| SF-268 | -4.30 | |
| SF-295 | -4.30 | |
| SF-539 | -4.30 | |
| SNB-19 | -4.30 | |
| U251 | -4.30 | |
| Melanoma | | |
| LOX IMVI | -4.30 | |
| M14 | -4.30 | |
| SK-MEL-2 | -4.30 | |
| SK-MEL-28 | -4.30 | |
| UACC-257 | -4.30 | |
| UACC-62 | -4.30 | |
| Ovarian Cancer | | |
| IGROV1 | -4.30 | |
| OVCAR-3 | -4.30 | |
| OVCAR-4 | -4.30 | |
| OVCAR-5 | -4.30 | |
| OVCAR-8 | -4.30 | |
| SK-OV-3 | -4.30 | |
| Renal Cancer | | |
| 786-0 | -4.30 | |
| ACHN | -4.30 | |
| CAKI-1 | -4.30 | |
| SN12C | -4.30 | |
| TK-10 | -4.30 | |
| UO-31 | -4.30 | |
| Prostate Cancer | | |
| PC-3 | -4.30 | |
| DU-145 | -4.30 | |
| Breast Cancer | | |
| MCF7 | -4.30 | |
| MCF7/ADR-RES | -4.30 | |
| MDA-MB-231/ATCC | -4.30 | |
| HS 578T | -4.30 | |
| MDA-MB-435 | -4.30 | |
| MDA-N | -4.30 | |
| BT-549 | -4.30 | |
| T-47D | -4.30 | |
| MG_MID | -4.30 | |
| Delta | 0.00 | |
| Range | 0.00 | |

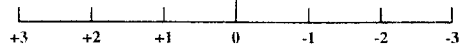

FUSED AZEPINONE CYCLIN DEPENDENT KINASE INHIBITORS

CROSS REFERENCE TO RELATED APPLICATION

This application is a continuation-in-part application of prior international application PCT/US99/13579, filed Jun. 16, 1999, which claims the benefit of Provisional application Ser. No. 60/089,619, filed Jun. 16, 1998, which is incorporated herein by reference.

FIELD

This invention concerns fused azepinone cyclin dependent kinase inhibitors, compositions comprising these compounds, and methods for administering such compounds for diseases of cellular proliferation and/or abnormal protein phosphorylation.

BACKGROUND

A major advance in the understanding of the control of the cell cycle has been the discovery of a family of enzymes called cyclin dependent kinases (cdk). Structurally they consist of a catalytic subunit and a regulatory subunit. The catalytic subunit is similar to the catalytic region in a number of serine/threonine kinases and at least eight distinct subunits have been described (cdk1(=cdc2)-cdk8). The regulatory subunit is necessary for activity and a number of proteins in this family have been described (cyclin A-cyclin H). Most cyclins can interact with more than one cdk and each known cyclin-cdk pair seems to have a distinct role in regulating the cell cycle. These activities are regulated not only through transcriptional and translational control of the subunits, but also through phosphorylation and dephosphorylation of the subunits. In addition, negative regulatory proteins have been discovered (p15, p16$^{INK4}$, p21$^{cip1}$ and p27$^{Kip1}$) which bind to the cyclin-cdk complex and inhibit activity. Structural understanding of the cdks and their regulation has been advanced by the solution of crystal structures for cdk2, cyclin A, cdk2-cyclin A, and cdk2-cyclin A-p27$^{Kip1}$. [Russo et al., "Crystal Structure of the P$_{27}$$^{Kip1}$ Cyclin-Dependent Kinase-4 Bound to the Cyclin-A-Cdk2 Complex," *Nature*, 382(6589):325–331 (1996).]

It is clear then that the cdks are important in the control of the cell cycle. As a result, it appears that alterations in cdk expression, function or regulation are associated with diseases of cellular proliferation. Alterations that would increase cdk activity (overexpression of the catalytic and/or positive regulatory subunit, or underexpression or deletion of negative regulatory proteins) have been reported in many cancers. The most common observation has been the deletion of the p16 (also called MTS1, CDKN2, p16$^{INK}$) gene. This gene codes for a protein that inhibits the activity of cdk4 and cdk6. This loss of inhibitory activity has been observed in a wide variety of primary human tumors and human tumor-derived cell lines, including lung, breast, brain, bone, skin, bladder, kidney, ovary, liver, colon, pancreas and leukemias. Overexpression of cdk1 in ovarian carcinoma and overexpression of cyclin D in non-small cell lung cancer also has been observed.

Clinical studies have shown that alterations in cdk pathways have prognostic significance. Deletion of the p 16 gene has shown to be associated with poor prognosis in B cell lymphomas [R. Garcia-Sanz et al., "Deletions and Rearrangement of Cyclin-Dependent Kinase 4 Inhibitor Gene p16 are Associated with Poor Prognosis in B cell Non-Hodgkin's Lymphomas," *Leukemia*, 11(11):1915–20 (1997)], and pediatric acute lymphoblastic leukemia [e.g., U. R. Kees et al. "Homozygous Deletion of the p16/MTS1 Gene in Pediatric Acute Lymphoblastic Leukemia is Associated with Unfavorable Clinical Outcome," *Blood*, 89(11): 4161–6 (1997)]. High expression of cyclin D1 has also been shown to predict early relapse in pediatric ALL. [U. R. Kees et al., "Deletions of the p16 Gene in Pediatric Leukemia and Corresponding Cell Lines," *Oncogene*, 12(10):2235–9 (1996).] High expression of cdk1 predicts disease recurrence in prostate adenocarcinoma. [B. V. Kallakury et al., "The Prognostic Significance of p34$^{cdc2}$ and Cyclin D1 Protein Expression in Prostate Adenocarcinoma," Cancer, 80(4): 753–63 (1997). Loss of p21 expression resulted in a significantly higher risk of recurrence following surgery for gastric carcinoma. M. Ogawa et al., "Loss of p21$^{WAF1/CIP1}$ Expression Correlates with Disease Progression in Gastric Carcinoma," *Br. J Cancer*, 75(11):1617–20 (1997).] Higher p27 expression has correlated with longer survival times in breast [e.g., C. Catzavelos et al., "Decreased Levels of the Cell-Cycle Inhibitor of p27$^{KIP1}$ Protein: Prognostic Implications in Primary Breast Cancer," *Nat. Med.*, 3(2):227–30 (1997)], and non-small cell lung cancer [V. Esposito, "Prognostic Role of the Cyclin-Dependent Kinase Inhibitor p27 in Non-Small Lung Cancer," *Cancer Res.*, 57(16):3381–5 (1997)].

Atherosclerosis is another disease associated with excessive cellular proliferation. An important signal for proliferation of vascular smooth muscle cells is increased expression of cdk2 and associated regulatory subunits, cyclin E and cyclin A. [E.g., C. Ihling, et al., "Topographical Association Between the Cyclin-Dependent Kinases Inhibitor P21, p53 Accumulation, and Cellular Proliferation in Human Atherosclerotic Tissue," *Arterioscler. Thromb. Vasc. Biol.*, 17(10): 2218–24 (1997).] This is consistent with the observation that high levels of homocysteine, known to cause occlusive arterial disease, causes increases in aortic cdk activity. [B. Lubec et al., "Homocysteine Increases Cyclin-dependent Kinase in Aortic Rat Tissue," *Circulation*, 94(10):2620–5 (1996).] The involvement of cdk2 also is consistent with the report that an antisense cdk2 oligonucleotide can prevent graft coronary arteriosclerosis. [J. Suzuki et al., "Prevention of Graft Coronary Arteriosclerosis by Antisense cdk2 Kinase Oligonucleotide," *Nat. Med.*, 3(8):900–3 (1997).]

Other diseases in which there is evidence that inhibitors of cdks may be of therapeutic use include mesangial proliferative glomerulonephritis [J. W. Pippin et al., "Direct in vivo Inhibition of the Nuclear Cell Cycle Cascade in Experimental Mesangial Proliferative Glomerulonephritis with Roscovitine, a Novel Cyclin-Dependent Kinase Antagonist," *J. Clin. Invest.*, 1900(9):2512–20 (1997)], infection with human cytomegalo-virus [W. A. Bresnahan et al., "Inhibition of Cellular cdk2 Activity Blocks Human Cytomegalovirus Replication," *Virology*, 231(2):239–47 (1997)], and malaria [R. Graeser et al., "Plasmodium Falciparum Protein Kinase 5 and the Malarial Nuclear Division Cycles," *Mol. Biochem. Parasitol*, 82(1):37–49 (1996)]. Abnormal phosphorylation of tau protein is a characteristic of Alzheimer's disease. Recent reports have shown that this phosphorylation is carried out, at least in part, by brain cdk5 [e.g., A. Sengupta et al., "Potentiation of GSK-3-Catalyzed Alzheimer-like Phosphorylation of Human tau by cdk5," *Mol Cell. Biochem.*, 167(1–2):99–105 (1997)]. Inhibitors of cdk5 should be useful in the treatment of the disease.

The potential role of cdk inhibitors in therapy of numerous diseases has led to efforts to find small molecules that inhibit all or some of the cdks. Several small molecules have been discovered that inhibit cdks specifically. These include the purine analogs, olomoucine, roscovitine, and CVT-313; the flavonoid, flavopiridol; and butyrolactone I. Other potent inhibitors of cdks are known, including staurosporine, UCN-01, and suramin, but these compounds also are potent inhibitors of other protein kinases. Crystal structures for several specific cdk inhibitors in complex with cdk2 have been determined, including olomoucine, roscovitine, and flavopiridol. One specific inhibitor of cdks has reached clinical trials, flavopiridol [H. H. Sadlacek et al., "Flavopiridol (186–8275, NSC-649890), a New Kinase Inhibitor for Tumor Therapy," *International Journal of Oncology*, 9:1143 (1996)], which has shown antitumor activity in Phase I trials in a number of tumor types and is progressing to Phase II trials. All other known cdk inhibitors have been shown to inhibit the growth of tumor cells in culture, although none are as potent as flavopiridol. No in vivo anti-tumor studies have been reported for these compounds, although there is an anecdotal report of a response to olomoucine in a spontaneous dog melanoma.

Several cdk inhibitors have shown activity in models for other diseases. Animal studies have shown that CVT-313 is an effective inhibitor of neointimal proliferation in a rat restenosis model. [E. E. Brooks et al., "CVT-313, a Specific and Potent Inhibitor of CDK2 that Prevents Neointimal Proliferation," *J. Biol. Chem.*, 272(46):29207–11 (1997).] Roscovitine has been reported to improve renal function in a rat model of glomerulonephritis, and to be an inhibitor of human cytomegalovirus replication in culture. Roscovitine also inhibits DNA synthesis in plasmodiumfalciparum, the malarial parasite. R. Graser et al., *supra*.

7,12-dihydro-indolo[3,2-d][1]benzazepin-6(5H)-one is a known compound. This compound originally was synthesized by Dr. Conrad Kunick, then at the Pharmazeutisches Institut der Universität Bonn. C. Kunick, "Synthese von 7,12-dihydro-indolo[3,2-d][1]benzazepin-6(5H)-onen und 6,11-dihydro-indolo[3', 2': 2,3]azepino[4,5-b]indol-5(4H)-on," *Arch. Pharm. (Weinheim)*, 325:297–299 (1992).

From the above discussion it is clear that known cyclin-dependent kinase inhibitors are useful for treating diseases of cellular proliferation and/or abnormal protein phosphorylation. But, there still is a need for new potent, and preferably selective, cdk inhibitors.

SUMMARY

The present invention provides a new class of cyclin dependent kinase inhibitors that also have shown antiproliferative activity in human tumor cell line assays. These compounds typically satisfy the formula

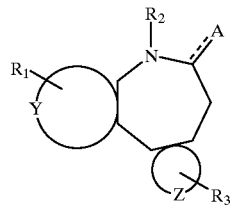

wherein A is oxygen or sulfur coupled to the ring by a single or a double bond, Y and Z are conjugated rings, the Y ring has at least one carbon atom with a substituent $R_1$ selected from the group consisting of alkoxy, amino, acyl, aliphatic substituents, particularly alkyl, alkenyl and alkinyl substituents, and even more particularly lower aliphatic substitutents, cyano, nitro, carboxyl, halogen, hydrogen, hydroxyl and imino, $R_2$ is selected from the group consisting of hydrogen, benzyl, lower alkyl, and lower alkyl ester, the Z ring has a substituent $R_3$ selected from the group consisting of hydrogen, lower aliphatic substituents, particularly lower alkyl substituents, or cyclic alkyl. "Lower" as used herein typically refers to compounds or substituents having 10 or fewer carbon atoms in a chain, and includes all position, geometric and stereoisomers of such substituents or compounds. Furthermore, if $R_1$ and $R_2$ are hydrogen and the Z ring comprises a five membered ring fused to a six membered ring then the six membered ring includes a substituent other than bromine. A is most typically a double bond, and the majority of compounds made to date have A double bonded to oxygen.

Most of the compounds of the present invention further satisfy the formula wherein A is oxygen or sulfur coupled to the ring by a single or double bond, $R_2$ is selected from the group consisting of hydrogen, aryl, lower aliphatic substituents, particularly alkyl and

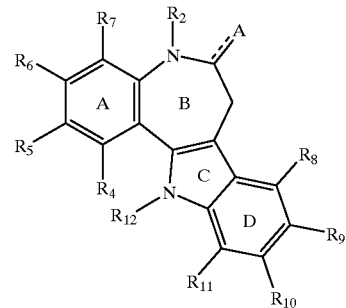

lower alkyl ester, $R_4$–$R_7$ are independently selected from the group consisting of alkoxy, amino, acyl, aliphatic substituents, particularly alkyl, alkenyl and alkinyl substituents, aliphatic alcohols, particularly alkyl alcohols, aliphatic nitrites, particularly alkyl nitrites, cyano, nitro, carboxyl, halogen, hydrogen, hydroxyl, imino, and α, β unsaturated ketones, $R_8$–$R_{11}$, are independently selected from the group consisting of aliphatic substituents, particularly alkyl, alkenyl and alkinyl substituents, particularly lower aliphatic substituents, aliphatic alcohols, particularly alkyl alcohols, alkoxy, acyl, , cyano, nitro, epoxy, haloalkyl groups, halogen, hydrogen, hydroxyl, cyano groups, and nitro groups, and $R_{12}$ is selected from the group consisting of aliphatic groups, particularly lower alkyl groups, aliphatic alcohols, particularly alkyl alcohols, carboxylic acids, and hydrogen. Particular examples of compounds satisfying these formulas have: $R_2$ selected from the group consisting of H, —CH$_2$COOCH$_3$, —CH$_3$, and —CH$_2$Ph, preferably hydrogen; $R_4$–$R_7$ independently selected from the group consisting of alkoxy, amino, acyl, alkyl, alkenyl, alkinyl, cyano, nitro, carboxyl, halogen, hydrogen, hydroxyl and imino, lower aliphatic alcohols, lower aliphatic nitrites, and α, β unsaturated ketones, cyano groups, and nitro groups, particularly —H, —OH, —C(=NH)NH$_2$, —CO$_2$H, —Br and —OCH$_3$; $R_8$–$R_{11}$, independently selected from the group consisting of alcohols, alkoxy, acyl, alkyl, alkenyl, alkinyl, cyano, nitro, epoxy, haloalkyl, halogen, hydrogen, hydroxyl and lower alkyl, particularly —H, halogens, —OH, —CH$_2$OH, —CH$_2$CHOCH$_2$, —CH$_2$CH$_2$CHOCH$_2$, —CF$_3$ and —OCH$_3$; and $R_{12}$ selected from the group consisting of alcohols, carboxylic acids, hydrogen and lower alkyl groups, particularly —H, —CH$_2$CH$_2$OH, —CH$_3$ and —CH$_2$CH$_3$.

The present invention also provides compositions comprising effective amounts of a compound, or compounds, satisfying the formulas above. Such compositions may further comprise inert carriers, excipients, diagnostics, direct compression binders, buffers, stabilizers, fillers, disintegrants, flavors, colors, lubricants, other active ingredients, other materials conventionally used in the formulation of pharmaceutical compositions, and mixtures thereof.

A method for inhibiting the proliferation of living cells in a subject, such as hyperproliferative cells and/or neoplastic cells, or for treating a neoplasm in a subject also is provided. The method first comprises providing a compound or compounds, or a composition comprising the compound or compounds, as described above. An effective amount of the compound(s) or composition(s) is then administered to a subject to inhibit the proliferation of living cells. Administering the compound(s) or composition(s) generally comprises administering topically, orally, intramuscularly, intranasally, subcutaneously, intraperitoneally, intralesionally or intravenously. The currently preferred administration method is intravenous. The effective amount should be as high as the subject can tolerate, but typically is from about 0.1 gram to about 3.0 grams of a compound, and from about 30 mg/kg of subject/dose to about 400 mg/kg of subject/dose, preferably from about 30 mg/kg of subject/dose to about 50 mg/kg of subject/dose.

BRIEF DESCRIPTION OF THE DRAWINGS

FIG. 1B provides cell line $LC_{50}$ data for 2-(2,3-Epoxypropyl)-9-trifluoromethyl-7,12-dihydroindolo[3,2-d][1]benzazepin-6(5H)-one.

DETAILED DESCRIPTION

Figure 1:
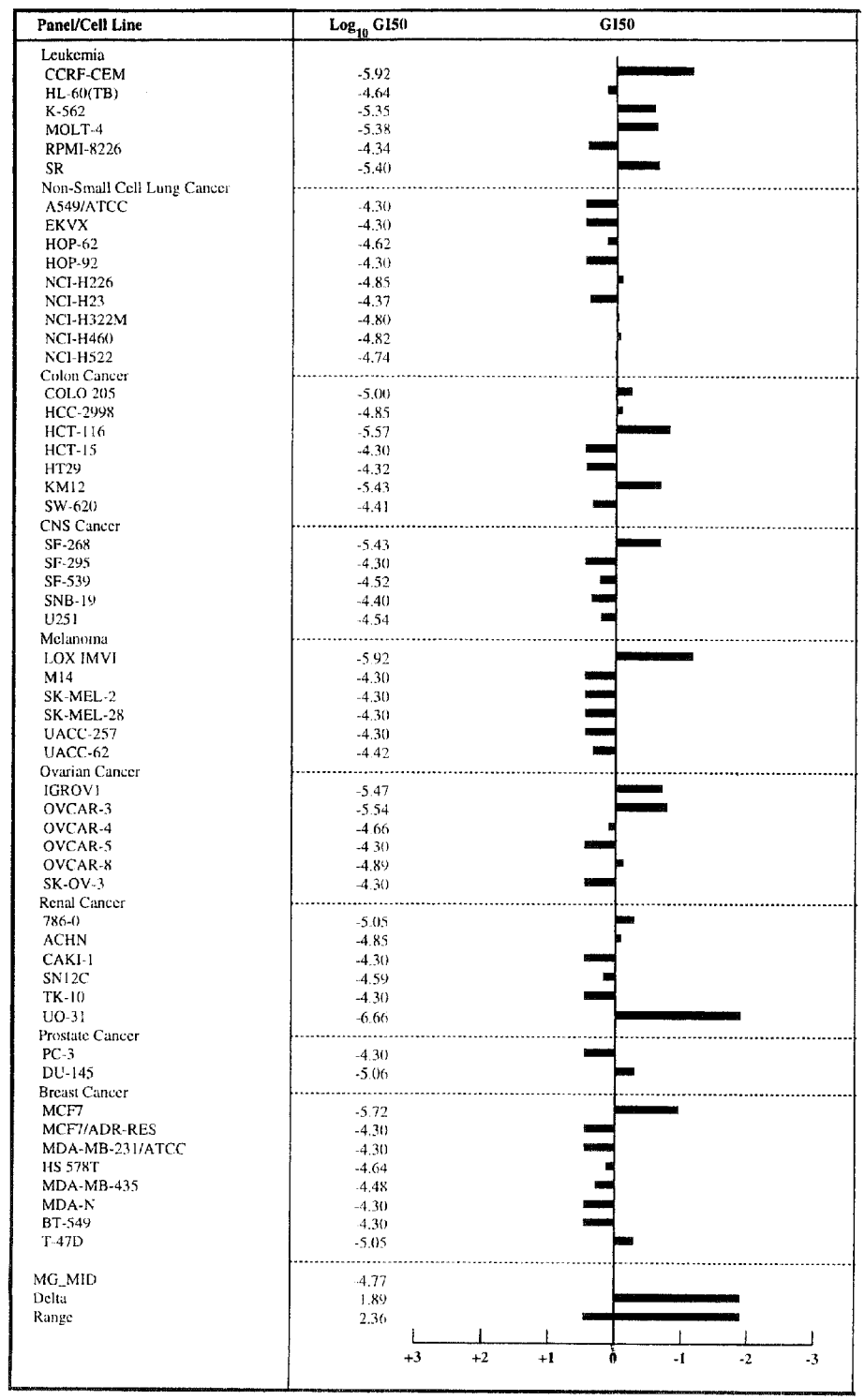
FIG. 1 provides cell line $GI_{50}$ data for 2-(2,3-Epoxypropyl)-9-trifluoromethyl-7,12-dihydroindolo[3,2-d][1]benzazepin-6(5H)-one.
Figure 1A:
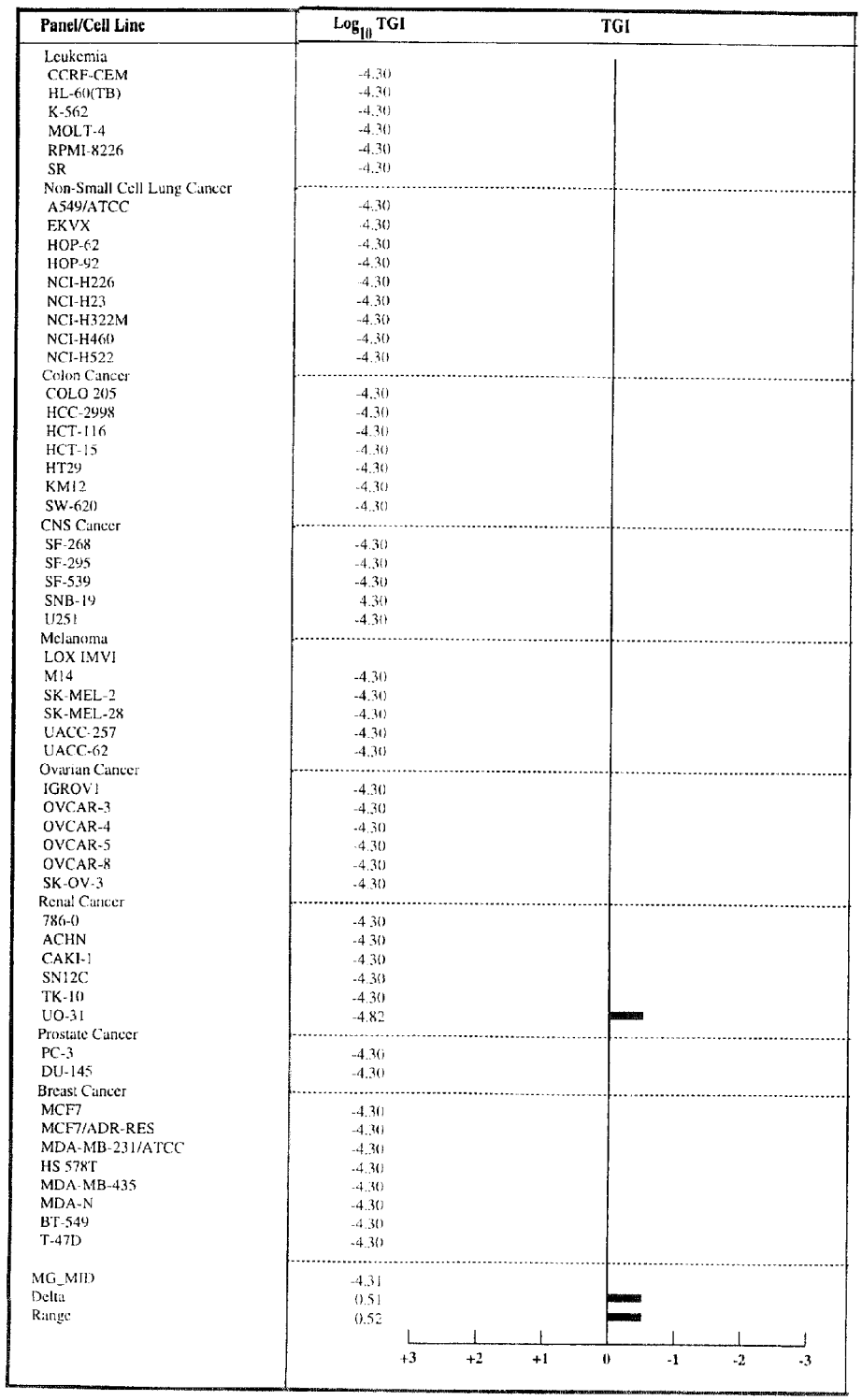
FIG. 1A provides cell line TGI data for 2-(2,3-Epoxypropyl)-9-trifluoromethyl-7,12-dihydroindolo[3,2-d][1]benzazepin-6(5H)-one.

The compounds of the present invention are specific cdk inhibitors, and also have significant biological activity in human tumor cell line assays. The following paragraphs describe how to make the compounds of the present invention, pharmaceutical compositions comprising such compounds, and methods for administering such compounds for treating diseases of cellular proliferation and/or abnormal protein phosphorylation and/or infectious diseases, such as cancer, atherosclerosis, Alzheimeres disease, and malaria.

I. COMPOUNDS

A. General Molecular Formula

Compounds of the present invention generally satisfy Formula I below.

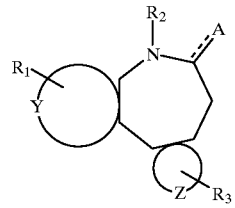

Formula 1

With reference to Formula 1, A is a oxygen or sulfur coupled to the B ring by a single or double bond, typically a double bond. If A is a single bond, then it also includes a hydrogen or lower aliphatic group, particularly a lower alkyl group bonded thereto. Y and Z are conjugated rings or conjugated heterocyclic rings, and generally are independently 5- or 6-membered rings. "Conjugated" means that the rings include at least one double bond separated by a single bond from a double bond or heteroatom having a lone pair of electrons, such as O, S or N, or two or more double bonds separated by single bonds. Unless specified otherwise, the terms "ring" and "rings" include rings having just carbon atoms form the ring structure, as well as rings that include heteroatoms, i.e., heterocycles, that form the ring structure. Working examples of compounds made according to the present invention have included benzene rings and thiophenes as the Y ring, and the Z ring has included pyrolidines and pyridines.

Y and Z also can comprise fused ring systems. For example, as described in more detail below, one example of a class of compounds satisfying Formula I have a Z ring comprising a five-membered ring fused to a six-membered ring. Additional examples of ring structures are provided below in Table 1.

Y and Z also can include substituents other than hydrogen coupled thereto. Examples of compounds satisfying Formula 1 include a Y ring having at least one carbon atom with a substituent $R_1$ coupled thereto. $R_1$ typically is selected from the group consisting of acyl, aliphatic substituents, particularly alkyl, alkenyl and alkinyl substituents, cyano, nitro, alkoxy (e.g., RO—), amino (e.g., $NR_2$, including primary, secondary and tertiary amines), carboxyl (—$CO_2H$), halogen, hydrogen, hydroxyl and imino [nitrogen-containing organic groups having a carbon-to-nitrogen double bond]. Particular compounds of the present invention have included $R_1$ groups selected from the group consisting of H, —OH, —C(=NH)—$NH_2$, —$CO_2H$, Br and —$OCH_3$.

$R_2$ typically is selected from the group consisting of hydrogen, aryl, lower aliphatic, particularly lower alkyl, alkyl aryl, e.g., benzyl, and lower alkyl ester. Examples of particular groups attached to the amide nitrogen of Formula 1 include H, —$CH_2COOCH_3$, —$CH_3$, and —$CH_2Ph$.

Compounds satisfying Formula 1 include a Z ring having at least one carbon atom with a substituent $R_3$ coupled thereto. $R_3$ generally is selected from the group consisting of hydrogen, lower alkyl or cyclic alkyl, e.g., cyclohexyl. Moreover, if $R_1$ and $R_2$ are hydrogen and the Z ring comprises a five membered ring fused to a six membered ring then the six membered ring includes a substituent other than bromine.

While Formula 1 is generic to compounds of the present invention, most of the compounds of the invention further satisfy Formula 2.

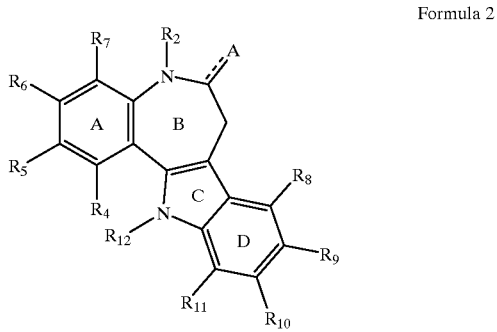

Formula 2

With reference to Formula 2, A is oxygen or sulfur coupled to the B ring by a single bond or a double bond, generally a double bond. $R_2$ is selected from the group consisting of hydrogen, acyl, aliphatic substituents, particularly alkyl, alkenyl and alkinyl substituents, even more particularly lower alkyl substituents, cyano, nitro, aryl, and lower alkyl ester, preferably hydrogen. $R_4$–$R_7$ are independently selected from the group consisting of alkoxy, amino, carboxyl, halogen, hydrogen, hydroxyl, imino, aliphatic alcohols, particularly lower alkyl alcohols, aliphatic nitriles, particularly lower aliphatic nitriles, and α, β unsaturated ketones. Particular examples of $R_4$–$R_7$, without limitation, include —H, —OH, —C(=NH)NH$_2$, —CO$_2$H, cyanoethyl, 3-hydroxy-1-propinyl, 3-oxo-1-butenyl, 2-(1-hydroxycyclohexyl)-ethinyl, halogens, particularly —Br, and —OCH$_3$. $R_8$–$R_{11}$ are independently selected from the group consisting of aliphatic-alcohols, particularly lower alkyl alcohols, alkoxides, acyl substituents, aliphatic substituents, particularly alkyl, alkenyl and alkinyl substituents, even more particularly lower alkyl substituents, cyano, nitro, epoxides, α, β-unsaturated carbonyl-bearing groups, ethers, haloaliphatic substituents, such as haloalkyl (e.g., fluoromethyl, difluoromethyl, trifluoromethyl), halogen, hydrogen, and hydroxyl. Particular examples of $R_8$–$R_{11}$ include, without limitation, —H, —CN, Br, Cl, and F, —OH, —CH$_2$OH, —CH$_2$CHOCH$_2$ (propylene oxide), —CH$_2$CH$_2$CHOCH$_2$ (butylene oxide), —CF$_3$, and —OCH$_3$.

$R_{12}$ generally is selected from the group consisting of lower aliphatic, particularly lower alkyl, lower aliphatic alcohols, particularly lower alkyl alcohols, carboxylic acids, and hydrogen. Particular examples of $R_{12}$ include, without limitation, —H, —CH$_2$CH$_2$OH, —CH$_3$ and —CH$_2$CH$_3$.

Examples of compounds satisfying both Formulas 1 and 2 can be selected, without limitation, from the group consisting of 7,12-dihydro-indolo[3,2-d][1]benzazepin-6(5H)-one, 2-bromo-7,12-dihydro-indolo[3,2-d][1]benzazepin-6(5H)-one, 9-bromo-7,12-dihydro-indolo[3,2-d][1]benzazepin-6(5H)-one, 9-chloro-7,12-dihydro-indolo[3,2-d][1]benzazepin-6(5H)-one, 11-chloro-7,12-dihydro-indolo[3,2-d][1]benzazepin-6(5H)-one, 10-bromo-7,12-dihydro-indolo [3,2-d][1]benzazepin-6(5H)-one, 8-bromo-6,11-dihydro-thieno[3', 2': 2,3azepino[4,5-b]indol-5(4H)-one, 9-bromo-7,12-dihydro-4-methoxy-indolo[3,2-d][1]benzazepin-6(5H)-one, 9-bromo-7,12-dihydro-4-hydroxy-indolo[3,2-d][1]benzazepin-6(5H)-one, 7,12-dihydro-4-methoxy-indolo[3,2-d][1]benzazepin-6(5H)-one, 9-bromo-7,12-dihydro-2,3-dimethoxy-indolo[3,2-d][1]benzazepin-6(5H)-one, 9-bromo-7,12-dihydro-2,3-dihydroxy-indolo[3,2-d][1]benzazepin-6(5H)-one, 7,12-dihydro-2,3-dimethoxy-indolo[3,2-d][1]benzazepin-6(5H)-one, 7,12-dihydro-9-trifluorynethyl-indolo[3,2-d][1]benzazepin-6(5H)-one, 7,12-dihydro-2,3-dimethoxy-9-trifluoromethyl-indolo [3,2-d][1]benzazepin-6(5H)-one, 2-bromo-7,12-dihydro-9-trifluoromethyl -indolo[3,2-d][1]benzazepin-6(5H)-one, 9-bromo-7,12-dihydro-indolo[3,2-d][1]benzazepin-6(5H)-thione, 9-bromo-5,12-bis-(t-butyloxycarbonyl)-7,12-dihydro-indolo[3,2-d][1]benzazepin-6(5H)-one, 9-bromo-12-(t-butyloxycarbonyl)-7,12-dihydro-indolo[3,2-d][1]benzazepin-6(5H)-one, 9-bromo-5,7-bis-(t-butyloxycarbonyl)-7,12-dihydro-indolo[3,2-d][1]benzazepin-6(5H)-one, 9-bromo-5,7,12-tri-(t-butyloxycarbonyl)-7,12-dihydro-indolo[3,2-d][1]benzazepin-6(5H)-one, 9-bromo-7,12-dihydro-5-methyloxycarbonylmethyl-indolo[3,2-d][1]benzazepin-6(5H)-one, 9-bromo-7,12-dihydro-12-methyloxycarbonylmethyl-indolo[3,2-d][1]benzazepin-6(5H)-one, 9-bromo-7,12-dihydro-12-(2-hydroxyethyl)-indolo[3,2-d][1]benzazepin-6(5H)-one, 2,9-dibromo-7,12-dihydro-indolo[3,2-d][1]benzazepin-6(5H)-one, 8,10-dichloro-7,12-dihydro-indolo[3,2-d][1]benzazepin-6(5H)-one, 9-cyano-7,12-dihydro-indolo [3,2-d [1]benzazepin-6(5H)-one, 9-bromo-7,12-dihydro-5-methyl-indolo[3,2-d][1]benzazepin-6(5H)-one, 5-benzyl-9-bromo-7,12-dihydro-5-methyl-indolo[3,2-d][1]benzazepin-6(5H)-one, 9-bromo-7,12-dihydro-12-methyl-indolo[3,2-d][1]benzazepin-6(5H)-one, 9-bromo-12-ethyl-7,12-dihydro-indolo[3,2-d][1]benzazepin-6(5H)-one, 9-bromo-7,12-dihydro-12-(2-propenyl)-indolo[3,2-d][1]benzazepin-6(5H)-one, 7,12-dihydro-9-methyl-indolo [3,2-d][1]benzazepin-6(5H)-one, 7,12-dihydro-9-methoxy-indolo[3,2-d][1]benzazepin-6(5H)-one, 9-fluoro-7,12-dihydro-12-(2-propenyl)-indolo[3,2-dl[1]benzazepin-6(5H)-one, 11-bromo-7,12-dihydro-indolo[3,2-d][1]benzazepin-6(5H)-one, 9-bromo-7,12-dihydro-2-(methyliminoamine)-indolo[3,2-d][1]benzazepin-6(5H)-one, 9-bromo-7,12-dihydro-2-(carboxylic acid)-indolo[3,2-d][1]benzazepin-6(5H)-one, 9-bromo-7,12-dihydro-10-hydroxy-indolo[3,2-d [1]benzazepin-6(5H)-one, 9-bromo-7,12-dihydro-11-hydroxymethyl-indolo[3,2-d][1]benzazepin-6(5H)-one, 7,12-dihydro-4-hydroxy-indolo[3,2-dl][1]benzazepin-6(5H)-one and 7,12-dihydro-2,3-dihydroxy-indolo[3,2-d][1]benzazepin-6(5H)-one, 2,3-dimethoxy-9-nitro-7,12-dihydro-indolo[3,2-d][1]benzazepin-6(5H)-one, 9-cyano-7,12-dihydro-indolo[3,2-d][1]benzazepin-6(5H)-one, 2,3-dimethoxy-9-cyano-7,12-dihydro-indolo[3,2-d][1]benzazepin-6(5H)-one, 9-nitro-7,12-dihydro-indolo[3,2-d][1]benzazepin-6(5H)-one, 2-bromo-9-nitro-7,12-dihydro-indolo[3,2-d][1]benzazepin-6(5H)-one, 2-(3-hydroxy-1-propinyl), 9-trifluoromethyl-7,12-dihydro-indolo[3,2-d][1]benzazepin-6(5H1)-one, 2-iodo-9-bromo-7,12-dihydro-indolo [3,2-d][1]benzazepin-6(5H)-one, 2-(3-oxo-1-butenyl), 9-trifluoromethyl-7,12-tetrahydro-indolo[3,2-d][1]benzazepin-6(5H)-one, 2-iodo,9-trifluoromethyl-7,12-dihydro-indolo[3,2-d][1]benzazepin-6(5H)-one, 7,12-dihydro-pyrido[3', 2':4,5]pyrrolo[3,2-d][I ]benzazepin-6(5H)-one, 11-methyl-7,12-dihydro-indolo[3,2-d][1]-benzazepin-6(5H)-one, 2-[2-(1-hydroxycyclohexyl)-ethinyl], 9-trifluoromethyl-7,12-dihydro-indolo[3,2-d][1]benzazepin-6(5H)-one, 2-cyano-7,12-dihydro-indolo[3,2-d

[1]benzazepin-6(5H)-one, 2-iodo-7,12-dihydro-indolo[3,2-d][]benzazepin-6(5H)-one, 11-ethyl-7,12-dihydro-indolo[3,2-d][1]-benzazepin-6(5H)-one, 2-(2,3-epoxypropyl)-9-trifluoromethyl-7,12-dihydroindolo[3,2-d][1]benzazepin-6 (5H)-one, 2-(epoxyethyl)-9-trifluoromethyl-7,12-dihydroindolo[3,2-d][1]benzazepin-6(5H)-one, 9-bromo-(2-epoxyethyl)-7,12-dihydroindolo[3,2-d][1]benzazepin-6 (5H)-one, 9-bromo-2--(2,3-epoxypropyl)-7,12-dihydroindolo[3,2-d][1]benzazepin-6(5H)-one, 2-(2-oxopropyl)-9-trifluoromethyl-7,12-dihydroindolo[3,2-d][1]benzazepin-6(5H)-one, 8-bromo-6,11-dihydro-thieno[3',2':2,3]azepino[4,5-b]indol-5(4H)-one, 8-chloro-6,11-dihydro-thieno[3',2':2,3]azepino[4,5-b] indol-5(4H)-one, 8-methyl-6,11-dihydro-thieno[3',2': 2,3]azepino[4,5-b]indol-5 (4H)-one, 3-(6-oxo-9-trifluoromethyl-5,6,7,12-tetrahydro-indolo[3,2-d][1]benzazepin-2-yl)-propionitrile, 3-(6-oxo-9-trifluoromethyl-5,6,7,12-tetrahydro-indolo[3,2-d][1]benzazepin-2-yl)-acrylonitrile, 3-(6-Oxo-9-trifluoromethyl-5,6,7,12-tetrahydro-indolo[3,2-d][1]-benzazepin-2-yl)-acrylic acid, methyl ester.

Additional examples of compounds of the present invention are provided below as Formulas 3–5.

Formula 3

Formula 4

Formula 5

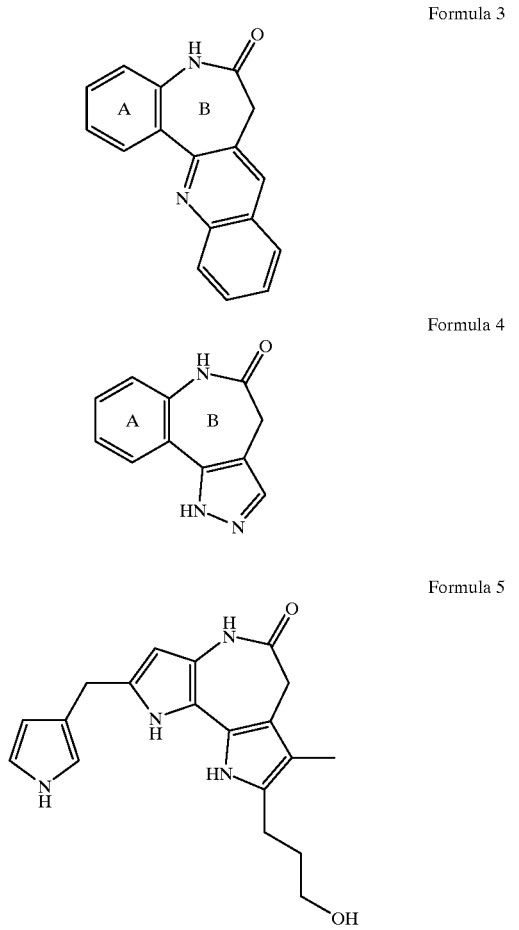

B. Synthesis of Compounds

There are several synthetic approaches to the basic ring system of Formula 1. The first known example of 7,12-dihydroindolo[3,2-d][1]benzazepin -6(5H)-one to be described was the lactam shown below in Scheme 1, which was synthesized as an intermediate in a sequence towards the iboga alkaloid selenium dehydrogenation products. This lactam was obtained via an eleven step procedure, the last step being the lactam ring closure initiated by cleavage of the tosyl protecting group in the lactam precursor shown in Scheme 1.

Scheme 1

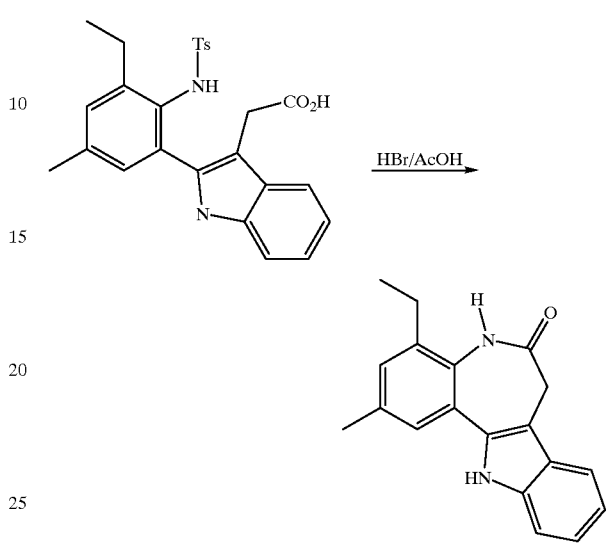

One method for synthesizing 7,12-dihydroindolo[3,2-d][1]benzazepin -6(5H)-ones was reported by Kunick as shown below in Scheme 2.

Scheme 2

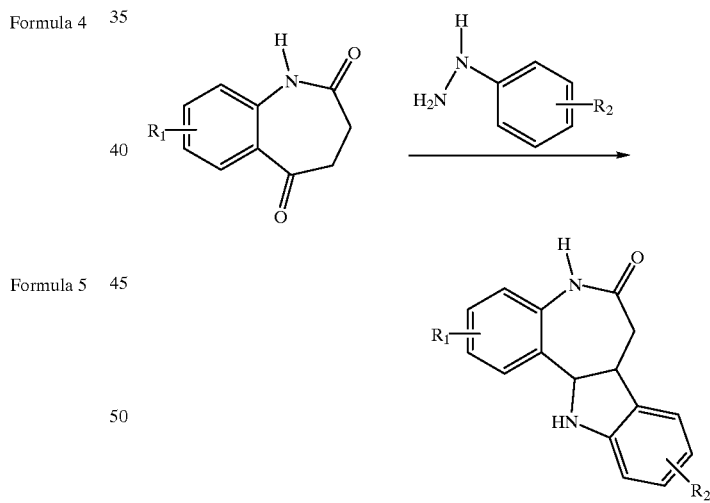

Kunick's method employs a Fischer indolization. An analog synthesis was published shortly after by the group of A. P. Kozikowski, who prepared the unsubstituted lactam as a putative ligand of the mitochondrial DBI (diazepam binding inhibitor) receptor complex.

The annelated azepinones are key intermediates in the synthesis of [b,d]-fused azepinones. Several strategies towards the structures have been reported. A general route to [1]benzazepin-2,5(3H, 4H)-diones was described by Witte and Boekelheide [J. Witte and V. Boekelheide, "Stereoselective Syntheses of Isoquinuclidones," *J. Org. Chem.*, 32:2849–2853 (1972), which is incorporated herein by reference], illustrated below as Scheme 3. Kunick has reported an alternative general strategy in having fewer steps and good overall yields.

Scheme 3

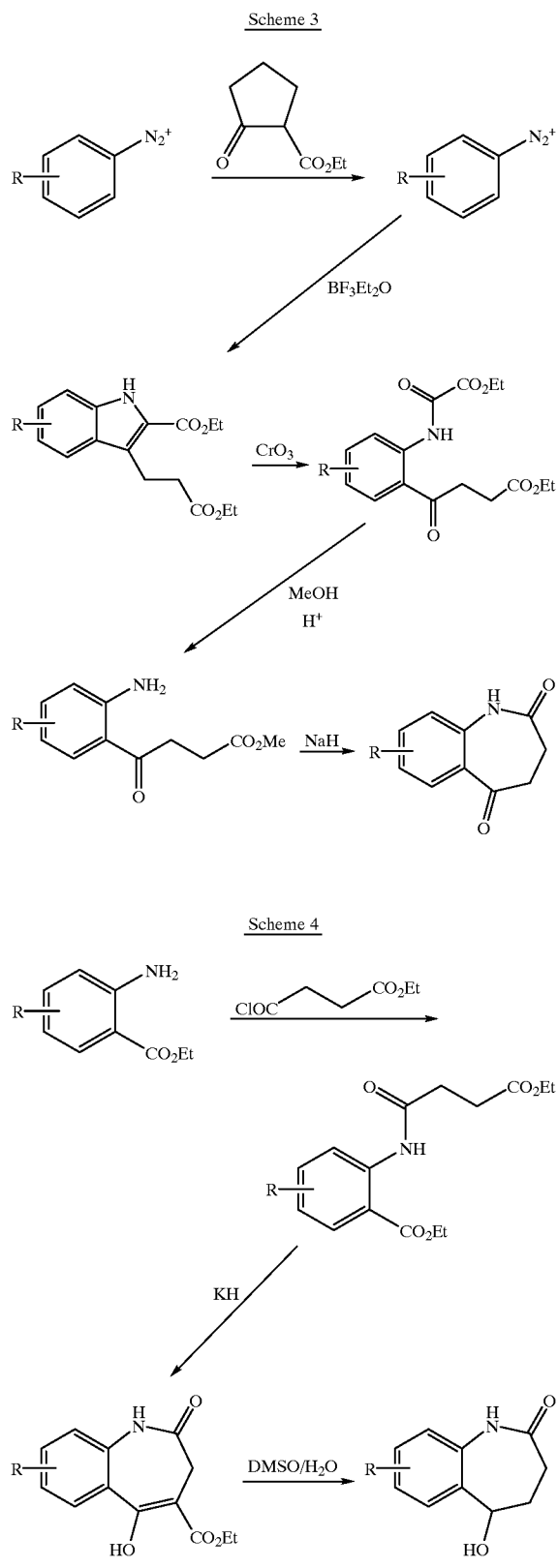

On the basis of the ring system of Formula 2, the synthesis of compounds according to the present invention may be achieved by the following strategies:

Introducing substituents in Ring A, and formation of heterocyclic rings. Substituents can be coupled to position 2 via electrophilic aromatic substitution at several stages in the synthetic pathway. For example, halogens and nitro substituents can be introduced. Other substituents can be introduced by nucleophilic exchange of the halogen or via diazonium intermediates, derived from the nitro compound. Carbon chains may be introduced at the 2 position by palladium catalyzed reactions employing halogen substituted derivatives. For compounds having one or more substituents in positions 1, 3, and/or 4, or a hetero atom in ring A, the synthetic route starts with an appropriate amino-substituted aromatic carboxylic acid. An example of this strategy is provided below as Scheme 5.

Scheme 5

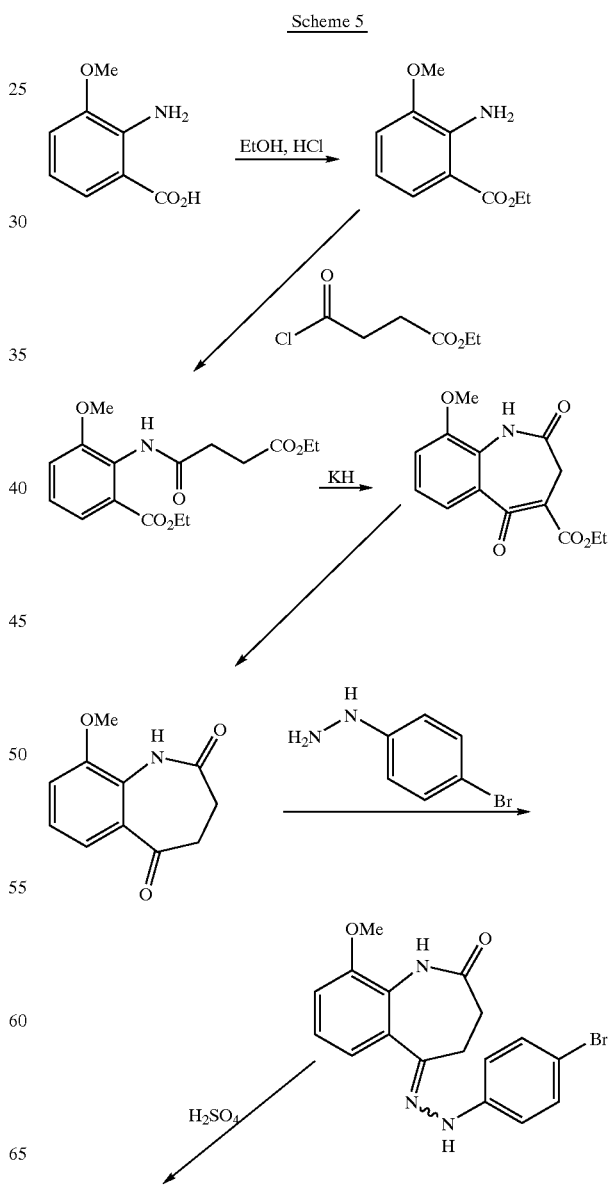

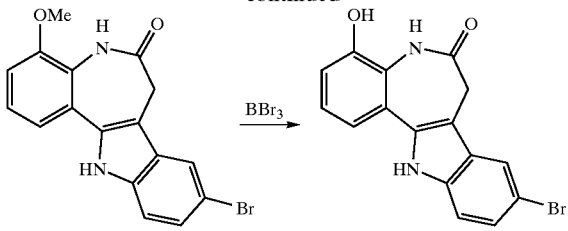

Modifications at positions 5 and 6. A nitrogen substitution at position 5 is achieved by reaction with an alkyl halide in the presence of a base. Sulfur can be exchanged for the oxygen by reaction with phosphorus sulfide. This thiolactam serves as starting material for compounds annelated at the 5,6 site, or the synthesis of methylthioimidates by reaction with iodomethane.

Introducing substituents into the D-Ring. Substituents intended at position 9 or 11, or appropriate precursor groups, are included in the phenylhydrazine (Scheme 2). Substitutions at position 10 are included via electrophilic aromatic substitution. Halogen substituents, e.g. the bromo substituent in the 9, 10 or 11 position, may be exchanged for other substituents, e.g. the cyano group, via a Rosenmund-von Braun reaction. The bromo substituent furthermore may serve as a reaction center for palladium catalyzed coupling reactions, e.g. Heck-reactions. Methyl substituents at positions 9 and 11 may be oxidized to carboxyl groups, which can be transformed by well known methods to other functional groups, e.g. alcohols, esters, ketones, aldehydes, etc.

Introduction of substituents in position 12. The nitrogen in position 12 can be alkylated selectively with alkyl halides using appropriate bases. Aminoalkyl chains can be placed at position 12 by a Mannich reaction.

Substitution of the indole part C,D for other ring systems. The aryl-(CO)—$CH_2$ motif of the intermediate shown in the Schemes above provides the structural basis for the annelation of various heterocyclic ring systems. For example, the following heterocycles have been annelated at this site utilizing the electrophilicity of the keto function and the C,H-acidity of the $CH_2$ group in the vicinal position: pyrazoles, pyrimidines, pyranes, pyridines, quinolines, and quinoxalines. Alternatively, the lactam ring closure strategy can be used for the preparation of the derivatives in which the C,D-system is substituted for another system.

Additional information concerning general synthetic approaches are provided below in Examples 1–5. Synthesis of particular compounds are described in Examples 6–30.

II. COMPOSITIONS

The compounds described herein can be formulated into compositions for administration to humans and animals (i.e., subjects) to, for example, inhibit the proliferation of living cells, particularly hyperproliferative or neoplastic cells. Such compositions include "effective amounts" of the compounds described above, and may further comprise inert carriers, excipients, diagnostics, direct compression binders, buffers, stabilizers, fillers, disintegrants, flavors, colors, lubricants, other active ingredients, other materials conventionally used in the formulation of pharmaceutical compositions, and mixtures thereof.

The method of the present invention comprises administering to humans or animals "effective amounts" of a compound, a mixture of compounds, or compositions comprising "effective amounts" of a compound or mixture of compounds. Persons of ordinary skill in the art will realize that an "effective amount" varies. It currently is believed that "administering an effective amount" comprises administering to subjects a total amount of compound per treatment of from about 0.3 gram to about 3 grams, preferably from about 0.5 gram to about 1 gram, of a compound or compounds, or compositions comprising the compound(s), according to the present invention. Moreover, it typically is desirable to provide as large a dose as possible to a subject, depending upon the ability of the subject receiving the compound, or compositions comprising the compound(s), to tolerate the dose. Effective amounts also can be stated with reference to amounts of a material per unit mass of the subject receiving the compounds. It currently is believed that such dosage for the present invention should be from about 30 mg/Kg of subject/dose to about 400 mg/Kg of subject/dose.

Tests performed using nearly sixty different cancer cell lines (see Examples below, drawings published with PCTIUS99/13579, and FIGS. 1–4 as attached hereto) indicate that the cytotoxic profile of the compounds of the present invention share certain similarities with other agents that are useful as antineoplastics. Thus, it would be within the purview of persons skilled in the art of preparing pharmaceutical formulations to add such compounds to pharmaceutical inert carriers, excipients, etc. suitable for administration to a subject, in a manner similar to that used for preparing such formulations of known antineoplastics. Compounds of the present invention can be administered to subjects using dosage protocols that are substantially similar to protocols used with other antineoplastics.

The compounds or compositions can be administered by any number of methods including, but not limited to, topically, orally, intramuscularly, intranasally, subcutaneously, intraperitoneally, intralesionally or intravenously. Currently, oral and intravenous administration are believed to be the preferred methods for administering the compounds and compositions.

III. BIOLOGICAL RESULTS

Compounds of the present invention also have been subjected to various biological analyses to determine their biological activity. The biological analyses include cdk inhibition assays and the drug screening procedure employed by the National Cancer Institute for the screening of drugs having possible anticancer utility.

A. Enzyme Inhibition Assays

The enzyme inhibition activity of compounds of the present invention have been assayed by Dr. Larent Meijer of CNRS, Roscoff, France, using his cdk inhibition assay. The assay is described by V. Rialet's and L. Meijer's "A Screening Test for Antimitotic Compounds Using the Universal M Phase-specific Protein Kinase, p34$^{cdc2}$/Cyclin b$^{cdc13}$, Affinity-Immobilized on p13sucl-Coated Microtitration Plates," *Anticancer Res.*, 11(4):1581–90 (1991), which is incorporated herein by reference. The results of these assays are provided below in Table 1. Where only substitutions are stated in Table 1, such substitutions refer to substituents on core compound 7,12-dihydro-indolo [3,2-d][1]benzazapine 6(5H)-one (or thione). Otherwise complete IUPAC names are provided. The following $IC_{50}$ values of known compounds are provided for purposes of comparison: flavopiridol=0.4 μM; olomoucine=7.0 μm; roscovitine=4.2 μM; CVT-313=4.2 μM; and butyrolactone I=0.6 μM.

TABLE 1

| Substitution | IC$_{50}$($\mu$M) cdc2/cyclin B | Cdk5 |
|---|---|---|
| 9-cyano | 0.024 | 0.044 |
| 2,3-dimethoxy, 9-nitro | 0.024 | |
| 9-nitro | 0.035 | |
| 2,3-dimethoxy, 9-cyano | 0.044 | |
| 3-(6-oxo-9-trifluoromethyl-5,6,7,12-tetrahydro-indolo[3,2-d][1]benzazepin-2-yl)-propionitrile | 0.047 | |
| 2-Br,9-nitro | 0.053 | |
| 2,3-dimethoxy-9-Br | 0.200 | 0.500 |
| 2-Br,9-trifluoromethyl | 0.240 | |
| 3-(6-oxo-9-trifluoromethyl-5,6,7,12-tetrahydro-indolo[3,2-d][1]benzazepin-2-yl)-acrylonitrile | 0.270 | |
| 2,3-dimethoxy,9-trifluoromethyl | 0.280 | 0.430 |
| 2-Br,9-Br | 0.300 | 10.100 |
| 2-(3-hydroxy-1-propinyl),9-trifluoromethyl | 0.300 | |
| 2-I,9-Br | 0.320 | |
| 2-(3-oxo-1-butenyl), 9-trifluoromethyl | 0.320 | |
| 9-Br | 0.400 | 0.850 |
| 9-trifluoromethyl | 0.400 | 0.600 |
| 8-trifluoromethyl-6,11-dihydro-thieno[3',2':2,3]azepino[4,5-b]indol-5(4H)-one | 0.500 | |
| 8-bromo-6,11-dihydro-thieno[3',2':2,3]azepino[4,5-b]indol-5(4H)-one. | 0.600 | |
| 2-I,9-trifluoromethyl | 0.700 | |
| 9-OCH$_3$ | 0.900 | 2.100 |
| 10-Br | 1.300 | 2.700 |
| 11-Br | 1.300 | 1.400 |
| 11-Cl | 1.400 | 2.900 |
| 12-CH$_2$COOMe | 1.400 | |
| 9-F | 1.600 | 1.300 |
| 9-CH$_3$ | 2.000 | 6.300 |
| 7,12-dihydro-pyrido[3',2':4,5]pyrrolo[3,2-d][1]benzazepin-6(5H)-one. | 2.200 | |
| 6 = S, 9-Br | 2.300 | 8.000 |
| 8,10-dichloro | 2.500 | |
| 12-CH$_2$CH$_2$OH | 3.000 | |
| 2,3-dihydroxy,9-Br | 3.000 | 8.000 |
| 11-methyl | 3.000 | |
| 2-[2-(1-hydroxycyclohexyl)-ethinyl],9-trifluoromethyl | 3.200 | |
| 2-Br | 3.300 | 5.000 |
| 2-cyano | 3.300 | |
| 2-I | 3.700 | |
| 11-ethyl | 3.800 | |
| 8-methyl-6,11-dihydro-thieno[3',2':2,3]azepino[4,5-b]indol-5(4H)-one | 4.000 | |
| 2,3-dimethoxy | 4.300 | 5.400 |
| 3-(6-Oxo-9-trifluoromethyl-5,6,7,12-tetrahydro-indolo[3,2-d][1]-benzazepin-2-yl)-acrylic acid, methyl ester | 4.300 | |
| 12-CH$_3$,9-Br | 6.200 | |
| 5-CH$_2$COOMe,9-Br | 6.40 | 5.300 |
| None | 7.000 | 10.100 |
| 5-CH$_3$,9-Br | 20.000 | 130.000 |
| 12-ethyl,9-Br | 23.000 | |
| 5-CH$_2$-Ph | 35.000 | 270.000 |
| 4-OH,9-Br | 40.000 | 1000.000 |
| 6-thiomethyl, 9-Br | 43.000 | 160.000 |
| 2-(2,3-epoxypropyl)-9-trifluoromethyl | 0.9 | |
| 2-(epoxyethyl)-9-trifluoromethyl | 0.3 | |
| 2-(2-oxopropyl)-9-trifluoromethyl | 0.2 | |
| 6-thiomethyl,9-Br | 43.000 | 160.000 |

Table 1 clearly shows that compounds provided as being representative of the present invention are potent inhibitors of cdc2/cyclin B. Disclosed compounds of the present invention typically have IC$_{50's}$ of less than about 50 $\mu$M, preferably less than about 10 $\mu$M, even more preferably less than about 5 $\mu$M, and particular disclosed compounds have IC$_{50's}$ of less than about 1 $\mu$M. The first 12 compounds listed in Table 1 have IC$_{50's}$ lower than most known compounds, and in the range of about 0.3 $\mu$M or less. The 9-cyano compound currently is the best known compound in terms of its inhibitory effects for cdc2/cyclin B.

Preferred compounds of the present invention having IC50's, of less than about 10 $\mu$M can be selected from the group consisting of 9-cyano-7,12-dihydro-indolo[3,2-d][1]benzazepin-6(5H)-one, 9-bromo-7,12-dihydro-2,3-dimethoxy-indolo[3,2-d][1]benzazepin-6(5H)-one, 2-bromo-7,12-dihydro-9-trifluoromethyl-indolo[3,2-d][1]benzazepin-6(5H)-one, 7,12-dihydro-2,3-dimethoxy-9-trifluoromethyl-indolo[3,2-d][1]benzazepin-6(5H)-one, 2,9-dibromo-7,12-dihydro-indolo [3,24d][1]benzazepin-6(5H)-one, 7,12-dihydro-9-trifluormethyl-indolo[3,2-d][1]benzazepin-6(5H)-one, 9-chloro-7,12-dihydro-indolo[3,2-d][1]benzazepin-6(5H)-one, 8-bromo-6,11-dihydro-thieno[3',2':2,3]azepino[4,5-b]indol-5(4H)-one, 7,12-dihydro-9-methoxy-indolo [3,2-d][1]benzazepin-6(5H)-one, 10-bromo-7,12-dihydro-indolo[3,2-dj [1]benzazepin-6(5H)-one, 11-bromo-7,12-dihydro-indolo[3,2-d][1]benzazepin-6(5H)-one, 11-chloro-7,12-dihydro-indolo [3,2-d][1]benzazepin-6(5H)-one, 9-fluoro-7,12-dihydro-indolo[3,2-d][1]benzazepin-6(5H)-one, 9-methyl-7,12-dihydro-indolo[3,2-d][1]benzazepin-6(5H)-one, 9-bromo-7,12-dihydro-indolo[3,2-d][1]benzazepin-6(5H)-thione, 8,10-dichloro-7,12-dihydro-indolo [3,2-d][1]benzazepin-6(5H)-one, 9-bromo-7,12-dihydro-12-(2-hydroxyethyl)-indolo[3,2-d][1]benzazepin-6(5H)-one, 9-bromo-7,12-dihydro-2,3-dihydroxy-indolo[3,2-d][1]benzazepin-6(5H)-one, 2-bromo-7,12-dihydro-indolo[3,2-d][1]benzazepin-6(5H)-one, 7,12-dihydro-2,3-dimethoxy-indolo [3,2-4[1]benzazepin-6(5H)-one, 9-bromo-7,12-dihydro-12-methyl-indolo [3,2-d][1]benzazepin-6(5H)-one, 9-bromo-7,12-dihydro-5-methyloxycarbonylmethyl-indolo [3,2-d][1]benzazepin-6(5H)-one, 7,12-dihydro-indolo[3,2-d][1]benzazepin-6(5H)-one, 7,12-dihydro-pyrido[3 ', 2': 4,5]pyrrolo[3,2-d][1]benzazepin-6(5H)-one, 11-methyl-7,12-dihydro-indolo [3,2-d][1]-benzazepin-6(5H)-one, 2-[2-(1-hydroxycyclohexyl)-ethinyl], 9-trifluoromethly-7,12-dihydro-indolo [3,2-d][1]benzazepin-6(5H-one, 2-cyano-7,12-dihydro-indolo [3,2-d][1]benzazepin-6(5H)-one, 2-iodo-7,12-dihydro-indolo[3,2-d][1]benzazepin-6(5H)-one, 11-ethyl-7,12-dihydro-indolo[3,2-d][1]-benzazepin-6(5H)-one, 8-methyl-6,11-dihydro-thieno [3', 2': 2,3]azepino[4,5-b]indol-5(4H)-one, 2—CH=CH—COOCH$_3$, 9-trifluoromethyl-7,12-dihydro-indolo [3,2-d][1]-benzazepin-6(5H)-one, 9-nitro-7,12-dihydro-2,3-dimethoxy-indolo[3,2-d][1]benzazepin-6(5H)-one, -nitro-7,12-dihydro-indolo[3,2-d][1]benzazepin-6(5H)-one, -cyano-7,12-dihydro-2,3-dimethoxy-indolo[3,2-d][1]benzazepin-6(5H)-one, 9-trifluoromethyl-7,12-dihydro-2—CH$_2$CH$_2$-CN-indolo[3,2-d][1]benzazepin-6(5H)-one, 2-bromo-9-nitro-7,12-dihydro-indolo[3,2-d][1]benzazepin-6(5H)-one, 9-cyano-7,12-dihydro-2,3-dimethoxy-indolo[3,2-d][1]benzazepin-6(5H)-one, 9-trifluoromethyl-7,12-dihydro-2-CH=CH—CN-indolo[3,2-d][1]benzazepin-6(5H)-one, 9-trifluoromethyl-7,12-dihydro-2-(3-hydroxy-1-propinyl)-indolo[3,2-d][1]benzazepin-6(5H)-one, 2-iodo-9-bromo-7,12-dihydro-indolo [3,2-d][1]benzazepin-6(5H)-one, 9-trifluoromethyl-7,12-dihydro-2-(3-oxo-1-butenyl)-indolo[3,2-d][1]benzazepin-6(5H)-one, 8-bromo-6,11-dihydro-thieno[3', 2':2,3]azepino[4,5-b]indol-5(4H)-one, 8-chloro-6,11-dihydro-thieno[3', 2':2,3]azepino[4,5-b]indol-5(4H)-one, 2-iodo-9-trifluoromethyl-7,12-dihydro-indolo[3,2-d][1]benzazepin-6(5H)-one, 9—OCH$_3$-7,12-dihydro-indolo[3,2-d][1]benzazepin-6(5H)-one, 12—CH$_2$COOMe-7,12- dihydro-indolo[3,2-d][1]benzazepin-6(5H)-one, and 6=S-9-bromo-7,12-dihydro-indolo[3,2-d][1]benzazepin-6(5H)-one.

Particularly preferred compounds for cdk inhibition have $IC_{50}s$ of less than about 1 μM.

These compounds include 9-cyano-7,12-dihydro-indolo[3,2-d][1]benzazepin-6(5H)-one, 9-bromo-7, 12-dihydro-2,3-dimethoxy-indolo[3,2-d][1]benzazepin-6(5H)-one, 2-bromo-7,12-dihydro-9-trifluoromethyl-indolo[3,2-d][1]benzazepin-6(5H)-one, 7,12-dihydro-2,3-dimethoxy-9-trifluoromethyl-indolo[3,2-d][1]benzazepin-6(5H)-one, 2,9-dibromo-7,12-dihydro-indolo[3,2-d][1]benzazepin-6(5H)-one, 7,12-dihydro-9-trifluoromethyl-indolo[3,2-d][1]benzazepin-6(5H)-one, 9-chloro-7,12-dihydro-indolo[3,2-d][1]benzazepin-6(5H)-one, 8-bromo-6,11-dihydro-thieno[3',2':2,3]azepino[4,5-b] indol-5(4H)-one, 7,12-dihydro-9-methoxy-indolo[3,2-d][1]benzazepin-6(5H)-one, (green compounds need IUPAC names) 2,3-dimethoxy-9-nitro-7,12-dihydro-indolo[3,2-d][1]benzazepin-6(5H)-one, 2,3-dimethoxy, 9-cyano-7,12-dihydro-indolo[3,2-d][1]benzazepin-6(5H)-one, 2—$CH_2CH_2$-CN,9-trifluoromethyl-7,12-dihydro-indolo[3,2-][1I]benzazepin-6(5H)-one, 2-bromo-9-nitro-7,12-dihydro-indolo[3,2-d][1]benzazepin-6(5H)-one, 2—CH=CH—CN, 9-trifluoromethyl-7,12-dihydro-indolo[3,2-d][I]benzazepin-6(5H)-one, 2-(3-hydroxy-1-propinyl), 9-trifluoromethyl-7,12-dihydro-indolo[3,2-4][1]benzazepin-6(5H)-one, 2-iodo-9-bromo-7,12-dihydro-indolo[3,2-d][1]benzazepin-6(5H)-one, 2-(3-oxo-1-butenyl), 9-trifluoromethyl-7,12-tetrahydro-indolo[3,2-d][1]benzazepin-6(5H)-one, 8-chloro-6,11-dihydro-thieno[3', 2': 2,3]azepino[4,5-b] indol-5(4H)-one, 2-iodo,9-trifluoromethyl-7,12-dihydro-indolo[3,2-d][1]benzazepin-6(5H)-one, 9-nitro-7, 12-dihydro-indolo[3,2-d][1]benzazepin-6(5H)-one, 9-bromo-7,12-dihydro-2,3-dimethoxy-indolo[3,2-d][1]benzazepin-6(5H)-one, 9-bromo-7,12-dihydro-indolo[3,2-d][1]benzazepin-6(5H)-one, 8-bromo-6, 1-1 dihydro-thieno[3', 2': 2,3]azepino[4,5-b] indol-5(4H)-one and 9—$OCH_3$-7,12-dihydro-indolo[3,2-d][1]benzazepin-6(5H)-one.

B. In Vitro Human Tumor Cell Line Assay

The human tumor cell line screening procedure uses a diverse, disease-oriented panel consisting of approximately 60 different human tumor cell lines organized into disease-specific subpanels. The compounds of the present invention were tested over a range of concentrations for cytotoxic or growth-inhibitory effects against cell lines comprising the panel. The eight subpanels represented diverse histologies (leukemias, melanomas, and tumors of the lung, colon, kidney, breast, ovary, and brain).

Compounds of the present invention were tested over a period of several days. During this period the cells were continuously exposed to various concentrations of the compounds tested. The tests produced individual dose-responses, one for each cell line (i.e., one for each example), and the data are disclosed in dose-response curves. The data provided by these dose response curves are summarized using a mean-graph format illustrated by FIGS. 1-30 as published with PCT/US99/13579, which is incorporated herein by reference.

To produce data for the mean-graph format, a compound concentration that produced a target level response was calculated for each cell line. Three different response parameters were evaluated. The first response parameter was the growth inhibition ("$GI_{50}$"). $GI_{50}$ is the concentration of compounds made according to the present invention that results in an apparent 50% decrease in the number of tumor cells relative to control tumor cells (not exposed to the compounds of the present invention) at the end of the incubation period.

The second response parameter was the total growth inhibition ("TGI"). TGI is the concentration at which the number of tumor cells remaining at the end of the incubation period substantially equal the number of tumor cells existing at the start of the incubation period.

The third response parameter was the lethal concentration ("$LC_{50}$"). $LC_{50}$ is the concentration of compounds made according to the present invention that caused an apparent 50% reduction in the number of tumor cells relative to the number of tumor cells present at the start of the incubation period.

In a typical $GI_{50}$ mean graph (e.g., FIG. 1 of the present application), the relative position of the vertical reference line along the horizontal concentration axis was obtained by averaging the negative $log_{10}GI_{50}$ values for all the cell lines tested against the compound. Horizontal bars were then plotted for the individual negative $log_{10}GI_{50}$ values of each cell line relative to the vertical reference line. The $GI_{50}$ graph thus provides a characteristic fingerprint for the compound, displaying the individual cell lines that are proportionately more sensitive than average (bars extending to the right of the reference line) or proportionately less sensitive than average (bars extending to the left of the reference line). The length of a bar is proportional to the difference between the $log_{10}GI_{50}$ value obtained with the particular cell line and the mean (represented by the vertical reference line). Similar mean graphs are shown in FIG. 2A for the TGI and in FIG. 2B for the $LC_{50}$ response parameters.

Figure 2:
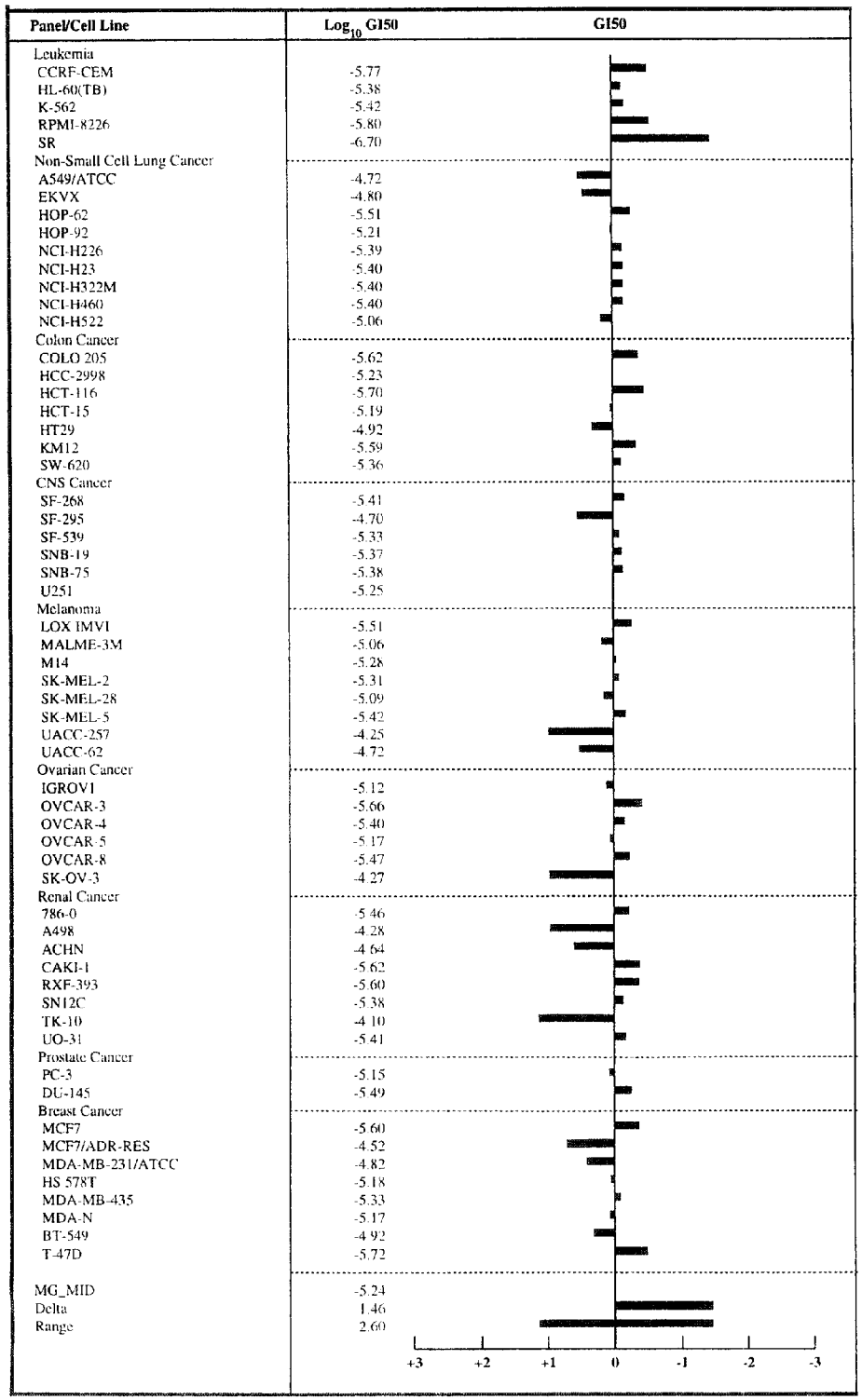
FIG. 2 provides cell line $GI_{50}$ data for 2-(Epoxypropyl)-9-trifluoromethyl-7,12-dihydroindolo[3,2-d][1]benzazepin-6(5H)-one.
Figure 2A:
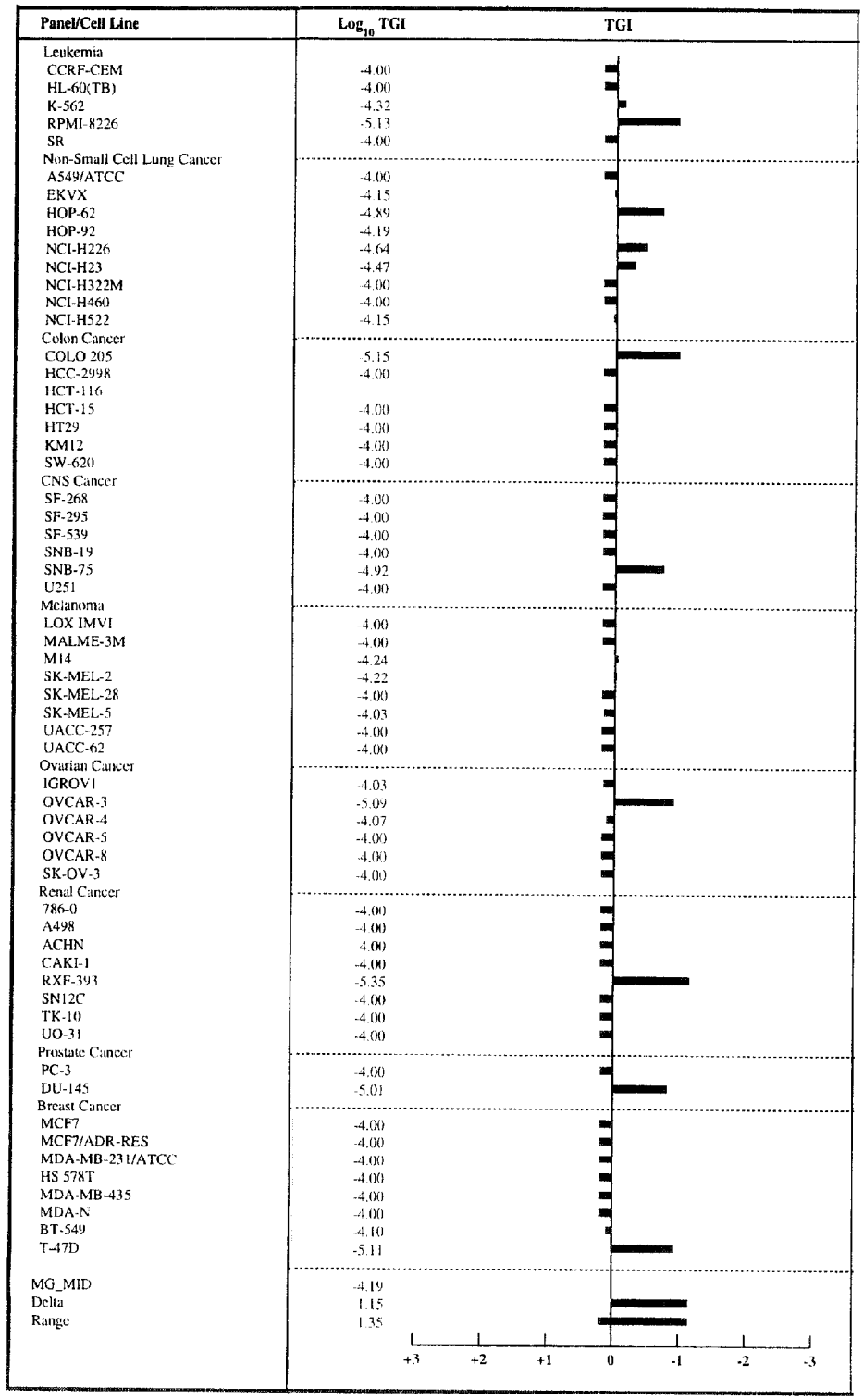
FIG. 2A provides cell line TGI data for 2-(Epoxypropyl)-9-trifluoromethyl-7,12-dihydroindolo[3,2-d][1]benzazepin-6(5H)-one.
Figure 2B:
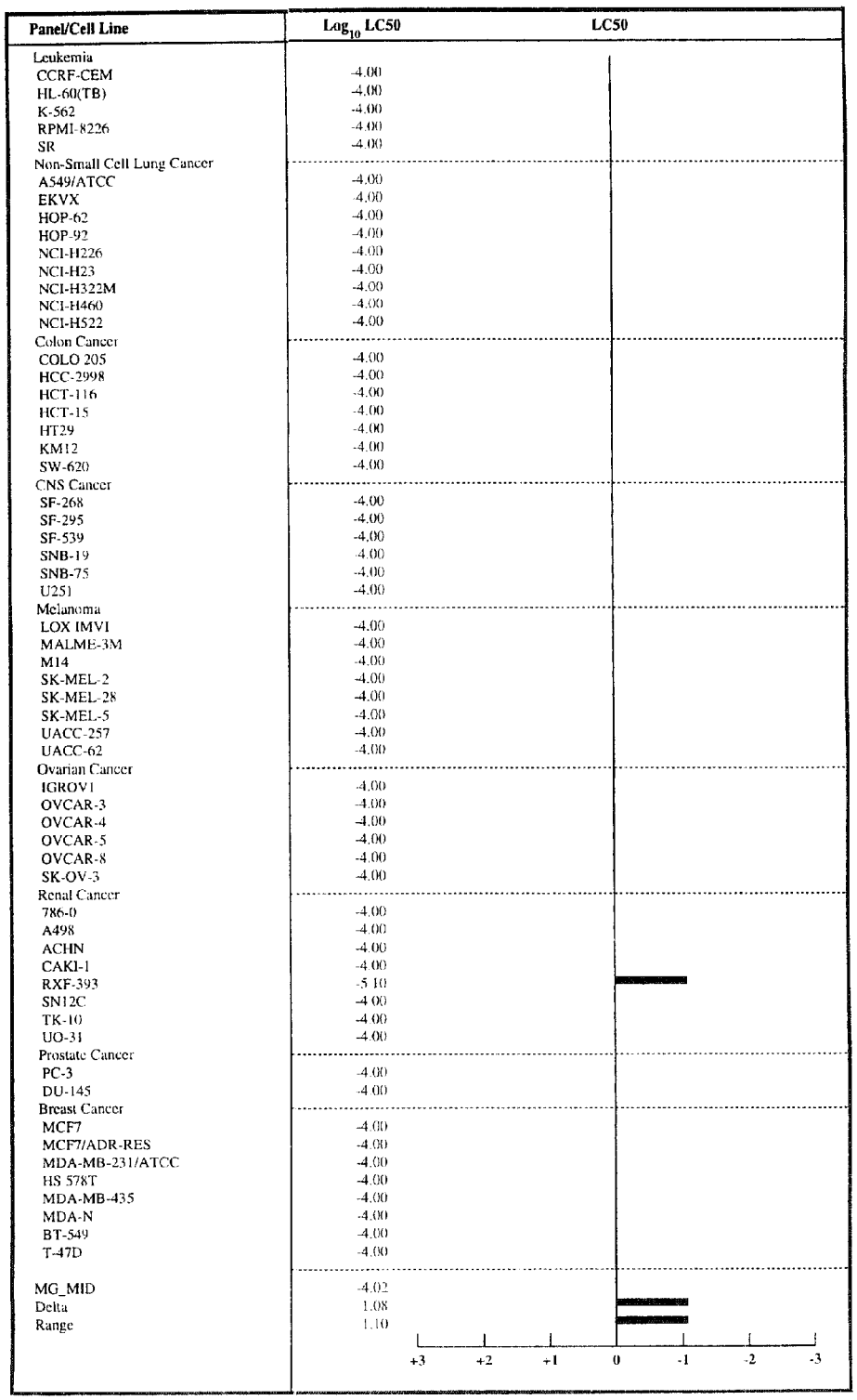
FIG. 2B provides cell line $LC_{50}$ data for 2-(Epoxypropyl)-9-trifluoromethyl-7,12-dihydroindolo[3,2-d][1]benzazepin-6(5H)-one.
Figure 3:
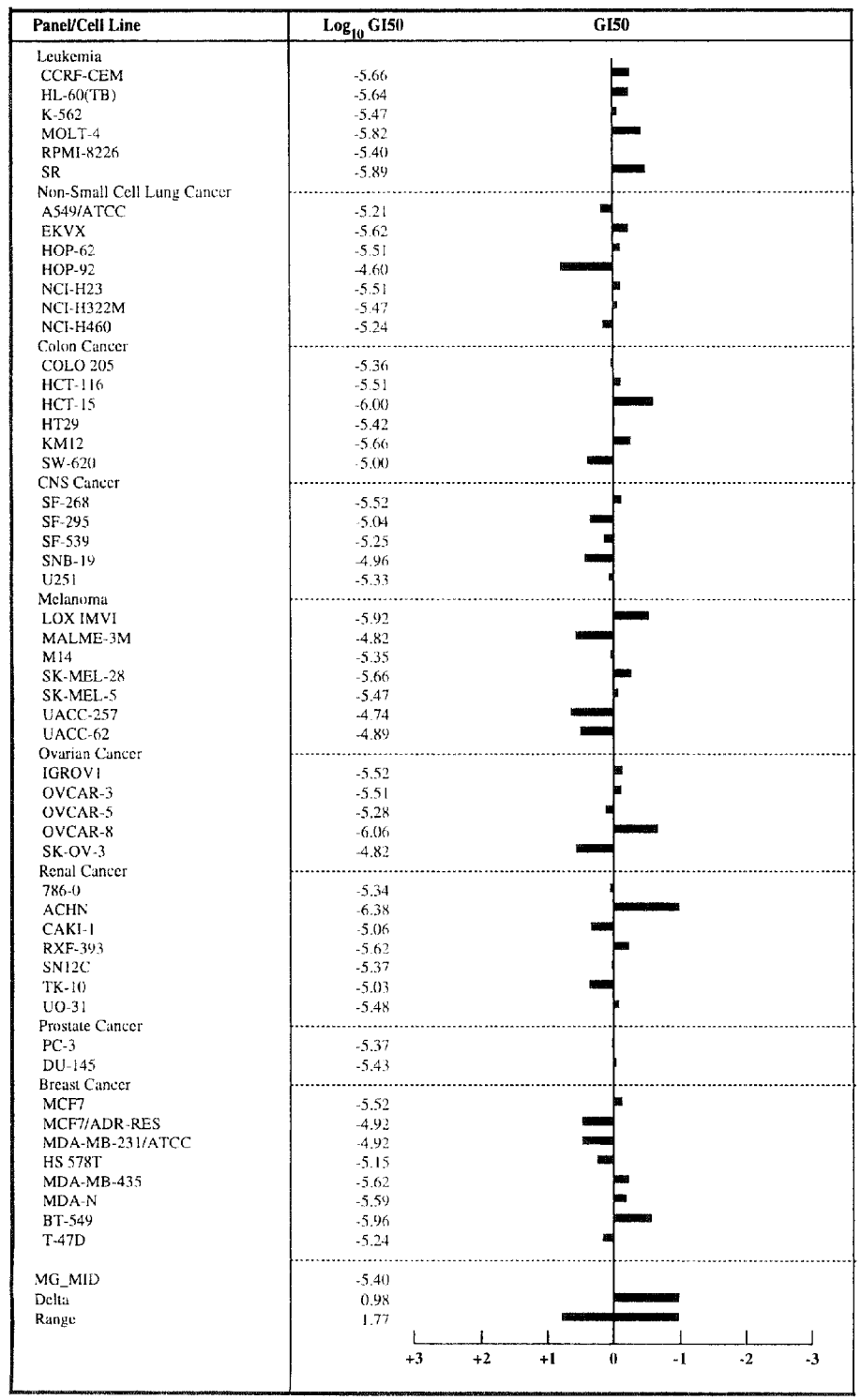
FIG. 3 provides cell line $GI_{50}$ data for 9-Bromo-2-(2,3-epoxypropyl-7,12-dihydroindolo[3,2-d][1]benzazepin-6(5H)-one.
Figure 3A:
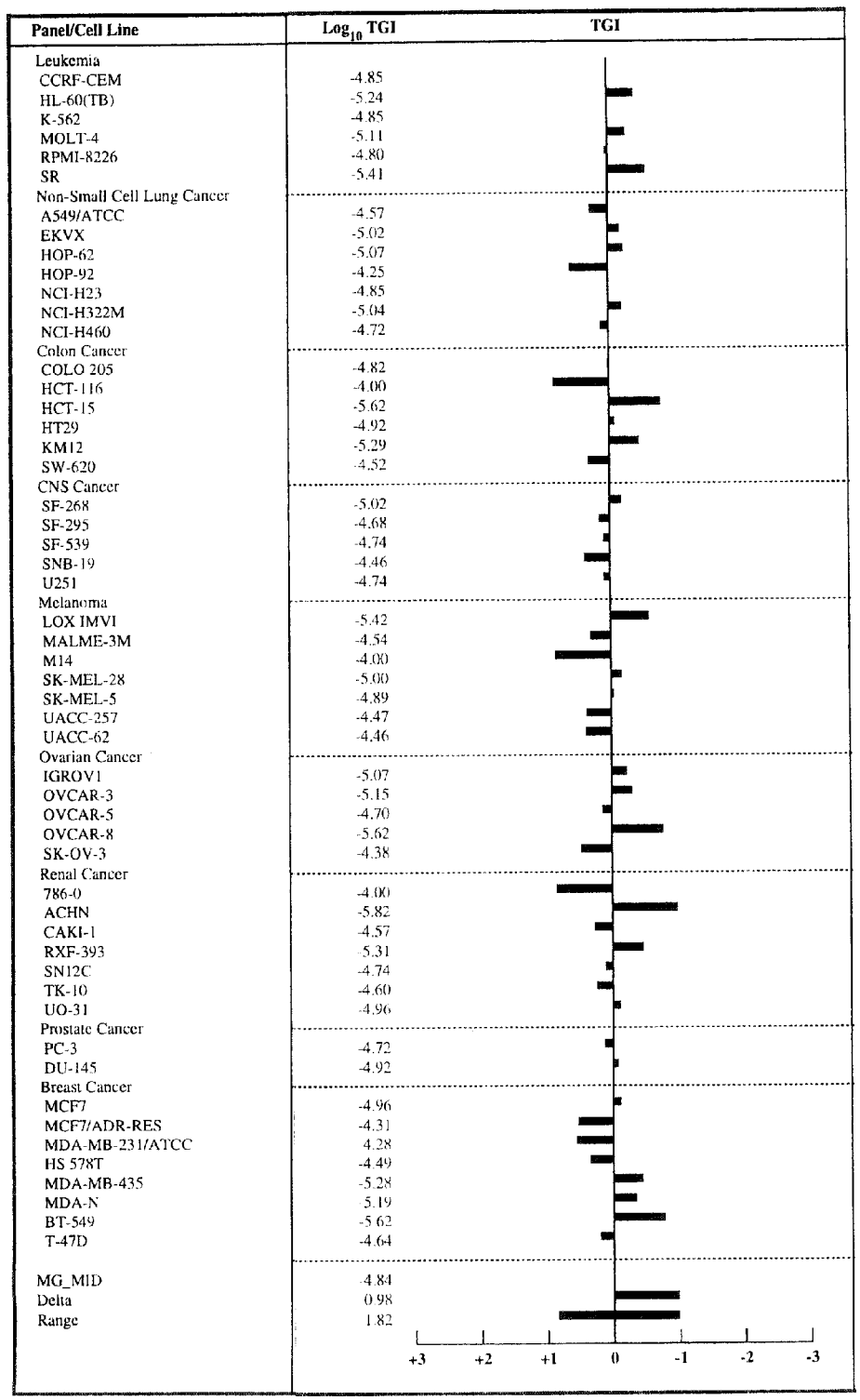
FIG. 3A provides cell line TGI data for 9-Bromo-2-(2,3-epoxypropyl-7,12-dihydroindolo[3,2-d][1]benzazepin-6(5H)-one.
Figure 3B:
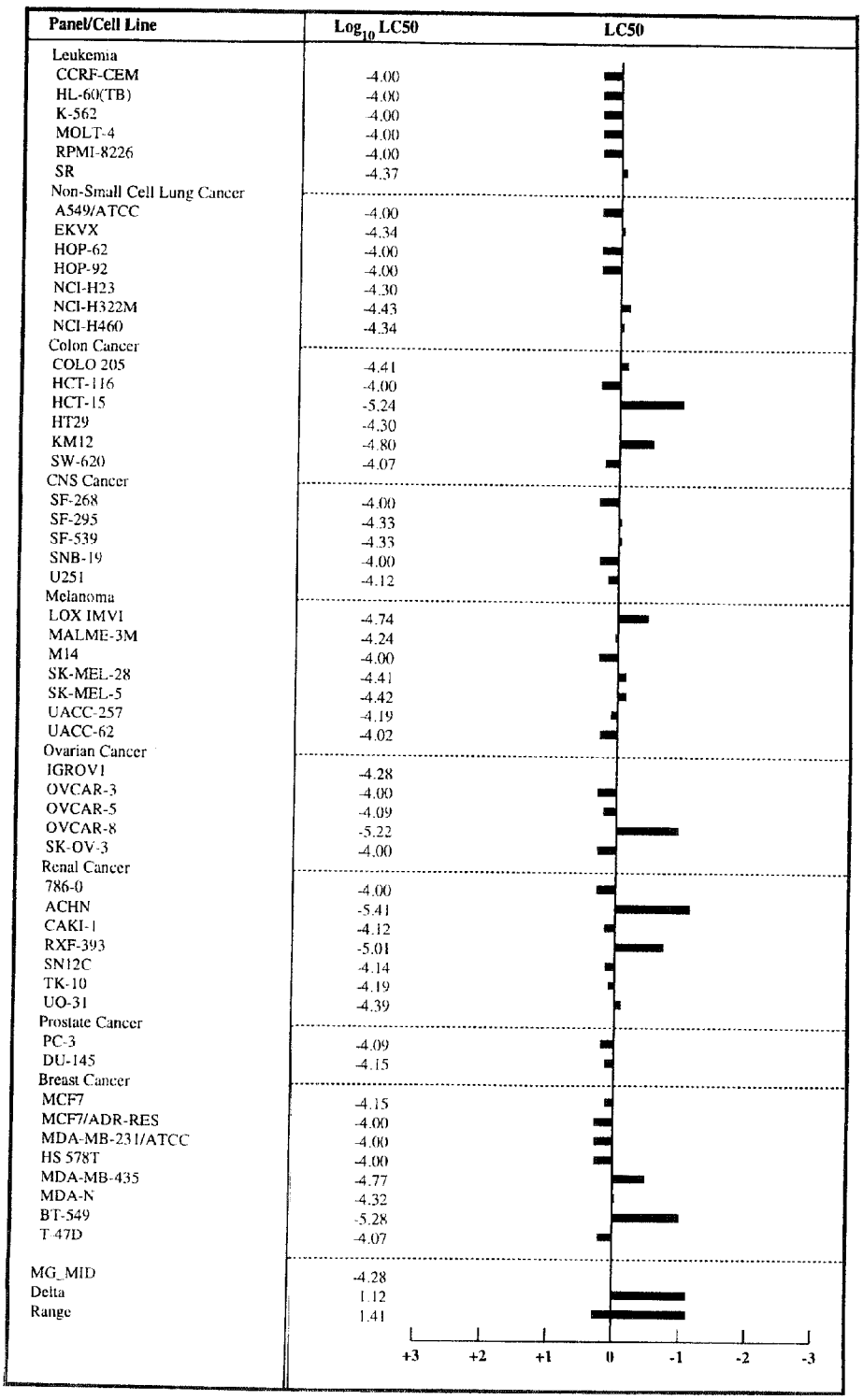
FIG. 3B provides cell line $LC_{50}$ data for 9-Bromo-2-(2,3-epoxypropyl-7,12-dihydroindolo[3,2-d][1]benzazepin-6(5H)-one.
Figure 4:
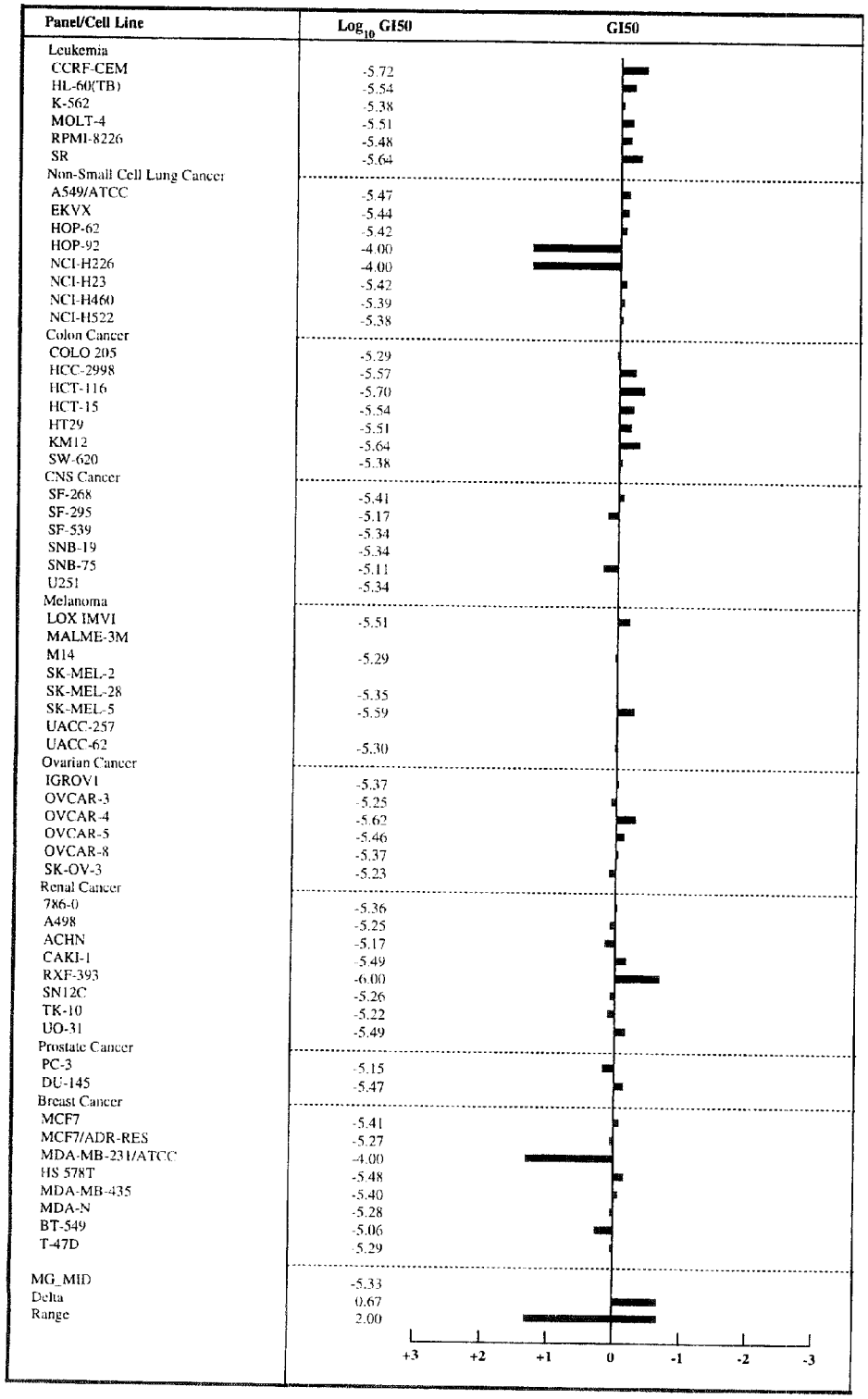
FIG. 4 provides cell line $GI_{50}$ data for 2-(2-oxopropyl)-9-trifluoromethyl-7,12-dihydroindolo[3,2-d][1]benzazepin-6(5H)-one.
Figure 4A:
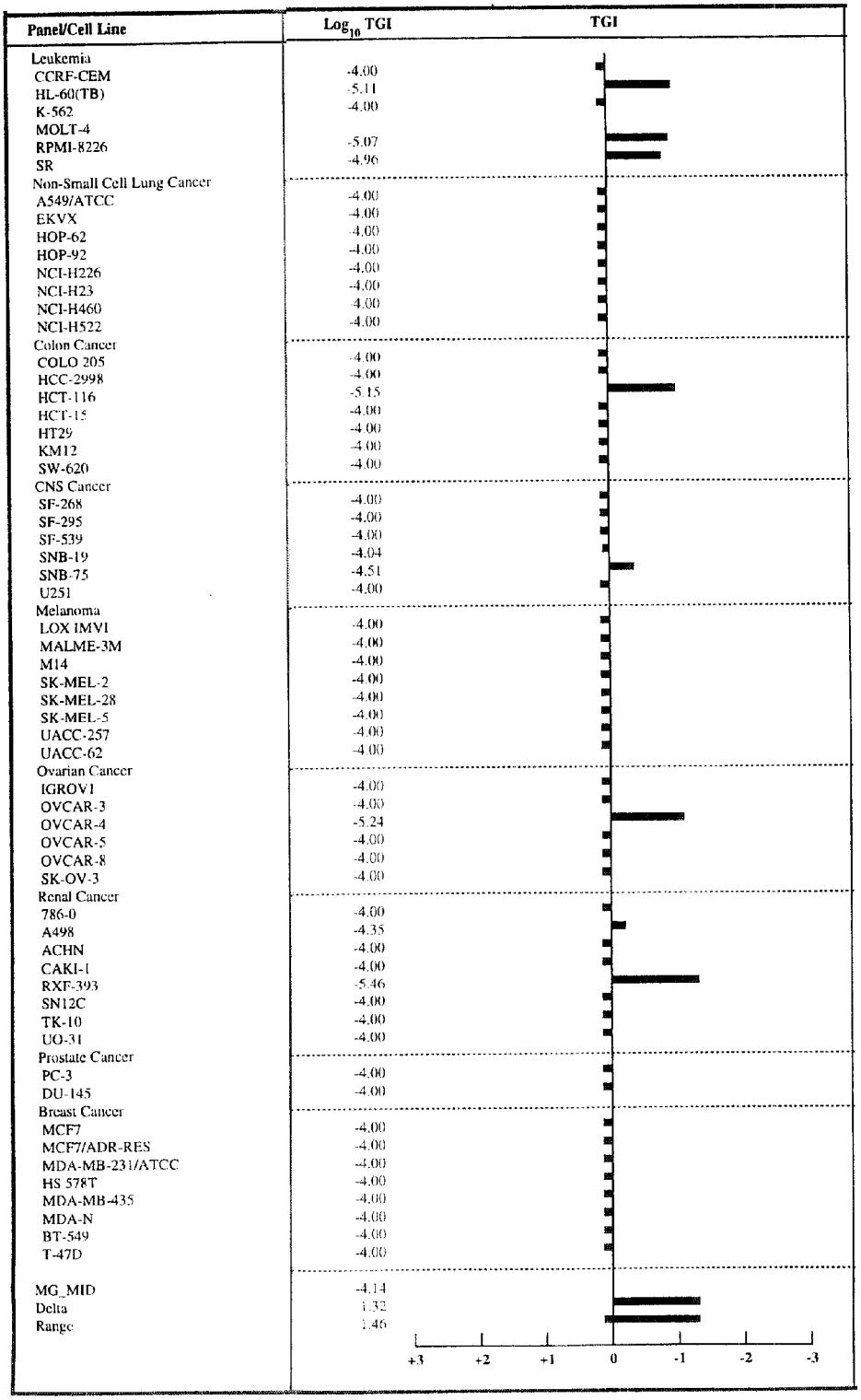
FIG. 4A provides cell line TGI data for 2-(2-oxopropyl)-9-trifluoromethyl-7,12-dihydroindolo[3,2-d][1]benzazepin-6(5H)-one.
Figure 4B:
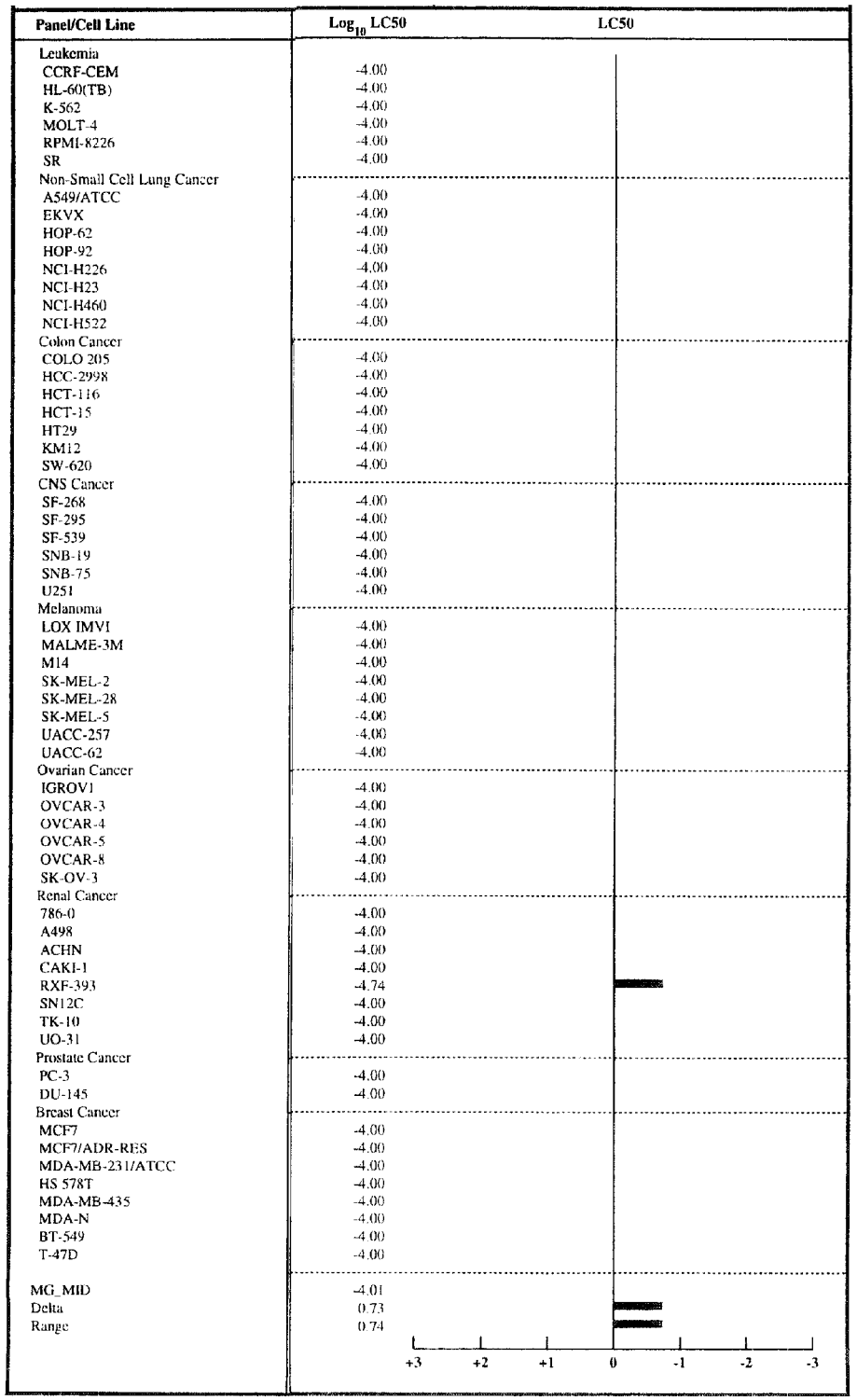
FIG. 4B provides cell line $LC_{50}$ data for 2-(2-oxopropyl)-9-trifluoromethyl-7,12-dihydroindolo[3,2-d][1]benzazepin-6(5H)-one.

Similar mean graphs are shown in FIG. 2 for the TGI (middle graph) and $LC_{50}$ (right-hand graph) response parameters.

FIGS. 1-30 as published with PCT/US99/13579 provide mean graph formats for particular compounds representative of the present invention. These FIGS. clearly show that compounds satisfying Formulas 1 and 2 above are useful for inhibiting the growth of human tumor cells. Certain results from the human tumor cell assays are summarized below in Table 2.

In Vitro Antitumor Activity on Cell Lines of the NCI Cancel Cell Screen by Compounds of the Present Invention: $GI_{50}[μM]$

TABLE 2

| Substitution | Average | SR | HCT-116 | RXF-393 |
|---|---|---|---|---|
| 2,3-dimethoxy,9-Br | 7 | 4 | 2 | 2 |
| 2-Br,9-trifluoromethyl | >100 | >100 | >100 | >100 |
| 2,3-dimethoxy,9-trifluoromethyl | 4 | 2 | 2 | 2 |
| 2-Br,9-Br | >100 | >100 | >100 | >100 |
| 9-Br(Parent Compound) | 43 | 4 | 2 | 5 |
| Roscovitine | 18 | 7 | 8 | 8 |
| 9-trifluoromethyl | 72 | 31 | 4 | 83 |
| 8-bromo-6,11-dihydro-thieno[3',2':2,3]azepino[4,5-b]indol-5(4H)-one | >89 | 28 | >100 | >100 |
| 12-$CH_2$COOMe | 66 | >100 | >100 | >100 |
| 6 = S,9-Br | 3 | — | — | 2 |
| 8,10-dichloro | >91 | >100 | >100 | >100 |
| 12-$CH_2CH_2$OH | 21 | 17 | 16 | 19 |
| 2,3dihydroxy,9-Br | >100 | >100 | >100 | >100 |
| 2,3-dimethoxy | 32 | 52 | 26 | 19 |
| 12-$CH_3$,9-Br | 34 | 3 | 7 | 18 |
| 5-$CH_2$COOMe,9-Br | 26 | 19 | 20 | 9 |
| Olomoucine | 51 | 27 | 38 | 20 |
| 5-$CH_3$,9-Br | 26 | 0.3 | 20 | 20 |
| 12-ethyl,9-Br | 51 | 5 | 34 | 22 |

TABLE 2-continued

| Substitution | Average | SR | HCT-116 | RXF-393 |
|---|---|---|---|---|
| 5-CH$_2$-Ph | 36 | 8 | 20 | 10 |
| 4-OH,9-Br | 39 | — | 50 | 27 |
| 6-thiomethyl,9-Br | 3 | 0.4 | 2 | 2 |
| 12-COO-tBu,9-Br | 6 | 3 | 3 | 4 |
| 12-allyl,9-Br | 65 | 40 | >100 | 51 |
| 5,7-di-COO-tBu,9-Br | >100 | >100 | >100 | >100 |
| 5,7,12-tri-COO-tBu,9-Br | 37 | >100 | 8 | 39 |
| 4-methoxy,9-Br | 20 | 33 | 10 | 20 |
| 4-methoxy | 79 | >100 | >100 | >100 |
| 5,12-di-COO-C-(CH$_3$)$_3$,9-Br | 44 | 14 | — | 87 |
| 2,3-dimethoxy,9-nitro | 1.2 | 0.20 | 0.30 | 0.76 |
| 9-cyano | 89 | 3 | 21 | >100 |
| 2,3-dimethoxy,9-cyano | 5.4 | 0.43 | 0.48 | 0.89 |
| 9-nitro | 0.37 | 0.02 | 0.07 | 0.27 |
| 3-(6-oxo-9-trifluoromethyl-5,6,7,12-tetrahydro-indolo[3,2-d][1]benzazepin-2-yl)-propionitrile | 2.2 | 0.05 | 0.79 | 1.9 |
| 2-Br,9-nitro | 87 | 24 | >100 | >100 |
| 3-(6-oxo-9-trifluoromethyl-5,6,7,12-tetrahydro-indolo[3,2-d][1]benzazepin-2-yl)-acrylonitrile | 83 | — | >100 | >100 |
| 2-(3-hydroxy-1-propinyl),9-trifluoromethyl | 14 | 0.33 | 2.8 | 8.1 |
| 2-I,9-Br | 55 | — | >100 | 47 |
| 2-(3-oxo-1-butenyl),9-trifluoromethyl | 2.7 | 0.5 | 1.3 | 2.9 |
| 8-chloro-6,11-dihydro-thieno[3',2':2,3]azepino[4,5-b]indol-5(4H)-one | 85 | 12 | >100 | >100 |
| 2-I,9-trifluoromethyl | 85 | >100 | >100 | >100 |
| 7,12-dihydro-pyrido[3',2':4,5]pyrrolo[3,2-d][1]benzazepin-6(5H)-one. | >100 | >100 | >100 | >100 |
| 11-methyl | 33 | 11 | 17 | 13 |
| 2-[2-(1-hydroxycyclohexyl)-ethinyl],9-trifluoromethyl | 2.5 | 2.6 | 2.3 | 2.2 |
| 2-cyano | 96 | >100 | >100 | >100 |
| 2-I | 25 | — | 20 | 24 |
| 11-ethyl | 58 | 7.0 | 74 | 24 |
| 8-methyl-6,11-dihydro-thieno[3',2':2,3]azepino[4,5-b]indol-5(4H)-one | 38 | 15 | 23 | 25 |
| 3-(6-Oxo-9-trifluoromethyl-5,6,7,12-tetrahydro-indolo[3,2-d][1]-benzazepin-2-yl)-acrylic acid, methyl ester | 96 | — | — | — |

Table 2 illustrates that compounds satisfying Formulas 1 and 2 not only are potent cyclin dependent kinase inhibitors, but also are potent inhibitors of the growth of human tumor cells.

Additional biological activity information is available for 9-bromo-7,12-dihydro-indolo[3,2-a][1]benzazepin-6(514)-one. For example, it also has been tested in the human tumor cell line screen and showed modest differential activity. This compound had an overall GI$_{50}$ of 43 μM and was most active in several colon lines (RCT-116 and KM12), along with a CNS line (SF-539). The compound also was able to totally inhibit the growth of two cell lines, HCT-116 and SF-539, both at a concentration of 28 μM.

Exponentially growing SUDHL-4 cells were exposed to 9-bromo-7,12-dihydro-indolo[3,2-d][1]benzazepin-6(5H)-one for 48 hours. The IC$_{50}$ for cell proliferation for this compound is about 3 μM. Cell cycle analysis of these cells revealed a prominent G2/M arrest, which is consistent with inhibition of cdk1.

Preliminary toxicity studies of 9-bromo-7,12-dihydro-indolo[3,2-d][1]benzazepin-6(5H)-one demonstrate that the maximum tolerated single dose to be about 400 mg/Kg.

Hollow fiber analyses also have been performed using 9-bromo-7,12-dihydro-indolo[3,2-d][1]benzazepin-6(5H)-one. These studies demonstrated that this compound showed substantial growth inhibition in the hollow fiber assay, i.e., 56% inhibition at 150 mg/Kg in the i.p. implanted fibers, 98% inhibition at 150 mg/Kg in the s.c. implanted fibers. See Example 31 below for the procedure used for the in vivo tests. Data is reported as % T/C according to the protocol of Example 31 for each of the 2 compound doses against each of the cell lines with separate values calculated for the intraperitoneal and subcutaneous samples, with a target value for % T/C being about 50 or less.

IV. EXAMPLES

The following examples are provided to illustrate certain particular features of the present invention. These examples should not be construed to limit the invention to the particular features exemplified.

Example 1

This example describes a general procedure for synthesizing compounds satisfying general Formula 2. A slurry of an appropriate IH-[I]benzazepine-2,5(3H,4H)-dione (6 mmol) in glacial acetic acid (10 mL) is placed in a round-bottomed flask equipped with oil bath, thermometer, reflux condenser and magnetic stirrer. After addition of the appropriate phenyl hydrazine (7 mmol) the mixture is heated to 70° C. with stirring for one hour. After cooling to room temperature concentrated sulfuric acid (0.5 mL) is added and the mixture is stirred at 70° C. for the indicated reaction time. After cooling to room temperature, the mixture is poured into a 10% aqueous sodium acetate solution (50 mL). A precipitate is formed, which is filtered off with suction and purified by recrystallization or column chromatography.

Example 2

This example describes a second general procedure for synthesizing compounds satisfying general Formula 2. A slurry of an appropriate 1H-[1]benzazepine-2,5(3H,4H)-dione (1 mmol) in glacial acetic acid (2 mL) is placed in a round-bottomed flask equipped with oil bath, thermometer, reflux condenser and magnetic stirrer. A suspension of sodium acetate (123 mg, 1.5 mmol) and the appropriate substituted phenylhydrazine (1.5 mmol) or the appropriate phenyl hydrazine hydrochloride (1.5 mmol) in glacial acetic acid(5 mL) is added dropwise with stirring. After stirring at 70° C. for 1 hour the mixture is cooled to room temperature. Concentrated sulfuric acid (0.1 mL) is added and the mixture is stirred at 70° C. for 1 hour. After cooling to room temperature, the mixture is poured into a 5% aqueous sodium acetate solution (15 mL). A precipitate forms, which is filtered off with suction and purified by recrystallization from the given solvent.

Example 3

This example describes a third general procedure for synthesizing compounds satisfying general Formula 2. To a suspension of 1H-[1]benzazepine-2,5(3H,4H)-dione (528 mg, 3 mmol) in glacial acetic acid (5 mL) is added a suspension of the appropriate substituted phenyl hydrazine (3.5 mmol) and sodium acetate (287 mg, 3.5 mmol) in glacial acetic acid dropwise and with stirring. The mixture is stirred for 1 hour at 70° C. and then cooled to room temperature. Concentrated sulfuric acid (0.25 mL) is added and the mixture is stirred for 1 hour at 70° C. The mixture is allowed to cool to room temperature and then poured into 5% aqueous sodium acetate solution (50 mL). A precipitate forms, which is filtered off with suction and then purified.

Example 4

This example describes a fourth general procedure for synthesizing compounds satisfying general Formula 2 involving the synthesis of phenols by cleavage of methoxy compounds. Boron tribromide (1002 mg, 4 mmol) was added to a solution of the appropriate methoxy compound (1 mmol) in dichloromethane (10 mL). The mixture was stirred by means of a magnetic stirrer, and the reaction was monitored by thin layer chromatography (silica gel, eluent acetone/toluene 1:1). When the spot caused by the starting methoxy compound was no longer detectable, water (10 mL) was added and the mixture was stirred for 1 hour. A solid formed, which was filtered off with suction, washed with water and recrystallized for purification.

Example 5

This example describes a fifth general procedure for synthesizing compounds satisfying general Formula 2 involving the reactions with alkyl halides. Powdered potassium hydroxide (56 mg, 1 mmol) was added with stirring and cooling by an ice bath to a solution of 9-bromo-7,12-dihydro-indolo[3,2-d][1]benzazepin-6(5H)-one (327 mg, 1 mmol) in dry acetone (120 mL). After stirring the mixture for 1 hour at 0° C., the appropriate alkyl halide (10 mmol) was added and stirring was continued for 3 days at room temperature. After addition of water (120 mL) a solid was formed, which was filtered off and recrystallized from ethanol/toluene.

Example 6

This example describes the synthesis of 9-cyano-7,12-dihydro-indolo[3,2-d][1]benzazapin-6(5H)-one.

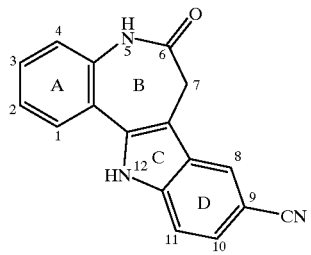

9-bromo-7,12-dihydro-indolo[3,2-d][1]benzazepin-6(5H)-one was first synthesized as a precursor for the synthesis of the 9-cyano derivative using the general procedure described above in Example 2. The synthesis was performed using lH-[1]benzazepine-2,5(3H,4H)-dione (1.05 g) and 4-bromophenylhydrazine (1.31 g), reaction time 1 hour. Pale yellow crystals in a 58% yield were obtained having: a mp. >330° C. (1,4-dioxane); ir (KBr): 3220 (NH), 1640 cm$^{-1}$ (C=O); $^1$H-nmr (DMSO-d$_6$, 300 MHz): δ (ppm)=3.50 (s, 2H, CH$_2$), 7.21–7.30 (m, 3H), 7.34–7.41 (m, 2H), 7.74 (bd, 1H, 7.5 Hz) 7.89 (d, 1H, 1.5 Hz), 10.05 (s, 1H, lactam NH), 11.75 (s, 1H, indole NH); $^{13}$C-nmr (DMSO-d$_6$, 75 MHz): δ (ppm)=31.3, 107.0, 111.4, 113.1, 120.1, 122.0, 122.1, 123.4, 124.2, 126.7,128.1, 128.1, 133.8, 135.4, 135.8, 171.1; C$_{16}$H, BrN$_2$O (327.2); Calcd. C 58.7, H 3.39, N 8.6; Found C 58.3, H 3.35, N 8.4.

A mixture of 9-bromo-7,12-dihydro-indolo[3,2-d][1]benzazepin-6(5H)-one (327 mg, 1 mmol) and copper(I) cyanide (180 mg, 2 mmol) in dimethyl formamide (15 mL) was refluxed for 12 hours. After cooling to room temperature water (20 mL) was added. The precipitate was filtered off with suction, washed with water, and then suspended in a mixture of water (25 mL) and 1,2-diaminoethane (40 mL). After stirring for 15 minutes, the solid was filtered off with suction, washed twice with 10% aqueous sodium cyanide solution and recrystallized twice from ethanol/toluene to yield 42% colorless crystals, m. p. >330° C.; ir (KBr): 3350, 3180 (NH), 2200 (CN), 1670 cm$^{-1}$ (C=O); $^1$H-nmr (DMSO-d$_6$, 400 MHz): δ (ppm)=3.59 (s, 2H, CH$_2$), 7.27–7.32 (m, 2H), 7.43 (dt, 1H, 1.0/7.6 Hz), 7.51 (dd, 1H, 1.3/8.4 Hz), 7.59 (d, 1H, 8.1 Hz), 7.76 (dd, 1H, 1.0/7.6 Hz), 8.32 (s, 1H), 10.16 (s, 1H, lactam-NH), 12.19 (s, 1H, indole-NH); $^{13}$C-nmr(DMSO-d$_6$, 100.6 MHz): δ(ppm)= 31.2, 101.2,108.2,112.5, 120.5,121.8,122.3, 123.7,123.9, 124.6, 126.3, 127.0, 128.7, 134.9, 135.8, 138.9, 171.3; C$_{17}$HIIN$_3$0 (273.31); Calcd. C 74.71, H 4.06, N 15.38; Found C 74.45, H 4.26, N 14.75.

Example 7

This example describes the synthesis of 7,12-dihydro-9-trifluoromethyl-indolo[3,2-d][1]benzazepin-6(5H)-one.

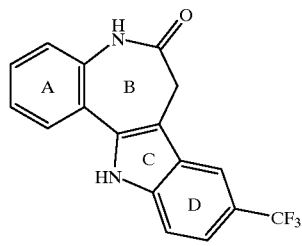

The synthesis was performed according to the general procedure described in Example 2 above using lH-[1]benzazepine-2,5(3H,4H)-dione (175 mg, 1 mmol) and trifluoromethylphenylhydrazine (264 mg, 1.5 mmol). The reaction yielded 33% of cream-colored crystals from ethanol, m. p. >330° C.; ir (KBr): 3200(NH), 1650 cm$^{-1}$ (C=O); $^1$H-nmr (DMSO-d$_6$, 400 MHz): δ (ppm)=3.61 (s, 2H, CH$_2$), 7.27–7.32 (m, 2H), 7.40–7.47 (m, 2H), 7.62 (d, 1H, 8.6 Hz), 7.78 (dd, 1H, 1.5/7.6 Hz), 8.13 (s, 1H), 10.15 (s, 1H, lactam-NH), 12.06 (s, 1H, indole-NH); $^{13}$C-nmr (DMSO-d$_6$, 100.6 MHz): δ (ppm)=31.2, 108.4, 112.0, 115.9 (q, J$_{C,F}$=4.1 Hz), 118.3 (q, J$_{C,F}$=3.2 Hz), 119.9 (q, J$_{C,F}$=34 Hz), 122.1, 122.3, 123.7,125.8, 127.0, 128.6, 134.7, 135.7, 138.7, 171.4 (one signal missing due to peak overlapping); C$_{17}$H$_{11}$FN$_2$O (316.30); Calcd. C 64.55, H 3.51, N 8.86; Found C 64.46, H 3.60, N 8.97.

Example 8

This example describes the synthesis of 7,12-dihydro-9-methyl-indolo[3,2-d][1]benzazepin-6(5H)-one.

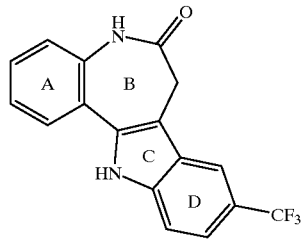

The synthesis was performed according to the general procedure described in Example 3 above using 4-methylphenylhydrazine hydrochloride (555 mg, 3.5 mmol). The reaction yield was 59% cream-colored crystals after recrystallization from ethanol, m. p. >330° C; ir (KBr): 3220 (NH), 1640 cm$^{-1}$ (C=O); $^1$H-nmr (DMSO-d$_6$, 400 MHz): δ (ppm)=2.41 (s, 3H, CH$_3$), 3.46 (s, 2H, CH$_2$), 7.00 (dd, 1H, 1.0/8.1 Hz), 7.22–7.38 (m, 4H), 7.43 (s, 1H), 7.73

(d, 1H, 6.9 Hz), 10.05 (s, 1H, lactam-NH), 11.42 (s, 1H, indole-NH); $^{13}$C-nmr (DMSO-d$_6$, 100.6 MHz): o (ppm)= 21.1, 31.5, 107.0, 111.1, 117.4, 122.2, 122.9, 123.5, 123.7, 126.7, 127.6, 127.7, 132.4, 135.3, 135.8, 171.5 (one signal missing due to peak overlapping); C$_{17}$H$_{14}$N$_2$O (262.31); Calcd. C 77.84, H 5.38, N 10.68; Found C 77.47, H 5.39, N 10.57.

Example 9

This example describes the synthesis of 7,12-dihydro-9-methoxy-indolo[3,2-d][1]benzazepin-6(5H)-one.

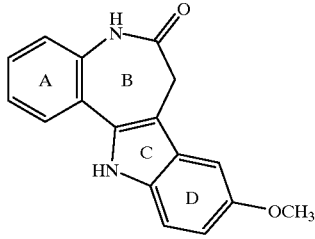

The synthesis was performed according to the general procedure described above in Example 3 using 4-methoxyphenylhydrazine hydrochloride (611 mg, 3.5 mmol). Purification by column chromatography (6 cm column of silica gel 60A, 100–200 mesh, eluent dichloromethane) yields 48% cream-colored powder, m. p. >330° C. (shrinking starting at 290° C.); ir (KBr): 3200 (NH), 1640 cm$^{-1}$ (C=O); $^1$H-nmr (DMSO-d$_6$, 400 MHz): δ (ppm)=3.49 (s, 2H, CH$_2$), 3.80 (s, 3H, OCH$_3$), 6.81 (dd, 1H, 2.0/8.6 Hz), 7.17 (d, 1H, 2.5 Hz), 7.22–7.28 (m, 2H), 7.30–7.38 (m, 2H), 7.72 (dd, 1H, 7.6 Hz), 10.04 (s, 1H, lactam-NH), 11.38 (s, 1H, indole-NH); $^{13}$C-nmr: not recorded; C$_{17}$H$_{14}$N$_2$O$_2$ (278.31); Calcd. C 73.37, H 5.07, N 10.07; Found C 72.32, H 5.39, N 9.75.

Example 10

This example describes the synthesis of 9-fluoro-7,12-dihydro-indolo[3,2-d][1]benzazepin-6(5H)-one.

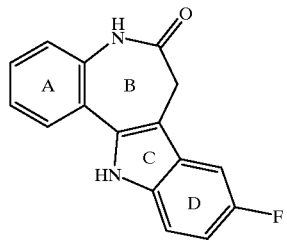

The synthesis was performed according to the general procedure described above in Example 4 using 4-fluorophenylhydrazine hydrochloride (569 mg, 3.5 mmol). Purification by column chromatography (6 cm column of silica gel 60A, 100–200 mesh, eluent dichloromethane) yields 52% cream-colored powder, m. p. >330° C. (shrinking starting at 180° C.); ir (KBr): 3220 (NH), 1635 cm$^{-1}$ (C=O); $^1$H-nmr (DMSO-d$_6$, 400 MHz): δ (ppm)=3.50 (s, 2H, CH$_2$), 7.00 (d"t", 1H, 2.5/9.2/9.2 Hz), 7.23–7.31 (m, 2H), 7.35–7.44 (m, 2H), 7.48 (dd, 1H, 2.5/9.7 Hz), 7.73 (dd, 1H, 1.5/7.6 Hz), 10.08 (s, 1H, lactam-NH), 11.67 (s, 1H, indole-NH); C$_{16}$H]IFN$_2$O (266.27); Calcd. C 72.17, H 4.16, N 10.52; Found C 72.03, H 4.23, N 10.47.

Example 11

This example describes the synthesis of 9-bromo-7,12-dihydro-2,3-dimethoxy-indolo[3,2-d][1]benzazepin-6(5H)-one.

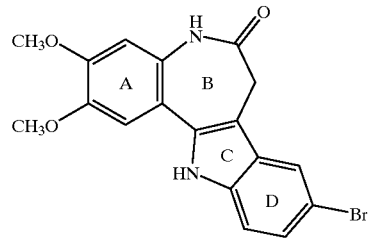

The preparation was performed according to the general procedure described above in Example 2 from 7,8-dimethoxy-lH-[1]benzazepin-2,5(3H,4H)-dione (235 mg, Immol) and 4-bromophenylhydrazine hydrochloride (336 mg, 1.5 mmol), yielding 55% red-brown crystals from ethanol/toluene, m.p.>330° C., ir (KBr): 3340, 3210 (NH), 1660 cm$^{-1}$ (C=O); $^1$H-nmr (DMSO-d$_6$, 400 MHz): δ (ppm)=3.45 (s, 2H, CH$_2$), 3.80 (s, 3H, OCH$_3$), 3.87 (s, 3H, OCH$_3$), 6.87 (s, 1H), 7.23–7.27 (m, 2H), 7.39 (d, 1H, 8.6 Hz), 7.86 (d, 1H, 2.0 Hz), 9.83 (s, 1H, lactam-NH), 11.70 (s, 1H, indole-NH); $^3$C-nmr (DMSO-d$_6$, 100.6 MHz): δ (ppm)= 31.3, 55.5, 55.7, 105.6, 106.0, 109.4, 111.5, 113.0, 114.4, 120.0, 124.0, 128.3, 129.4, 134.4, 135.7, 145.3, 148.9, 170.7; C$_{18}$H$_{15}$BrN$_2$O$_3$ (387.24); Calcd. C 55.83 H 3.90 N 7.24 Br 20.63; Found C 55.80 H 3.95 N 7.25 Br 20.34.

Example 12

This example describes the synthesis of 2-bromo-7,12-dihydro-indolo[3,2-d][1]benzazepin-6(5H)-one.

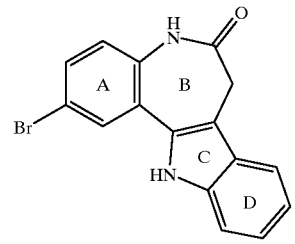

The synthesis was performed corresponding to the general procedure described above in Example 2, using 7-bromo-1H-[1]benzazepine-2,5(3H,4H)-dione (1.52 g) and phenyl hydrazine (0.69 mL) with a reaction time of about 1 hour Off-white crystals were obtained in a 63% yield, mp. >330° C. (ethanol); ir (KBr): 3260 (NH), 1650 cm$^{-1}$ (C=O); $^1$H-nmr (DMSO-d$_6$, 300 MHz): o (ppm)=3.53 (s, 2H, CH$_2$), 7.08 (ddd, 1H, J=1/7/8 Hz), 7.19 (ddd, 1H, 1/7/8 Hz), 7.20 (d, 1H, 8.5 Hz), 7.43 (ddd, 1H, 0.5/1/8 Hz), 7.52 (dd, 1H, 2.5/8.5 Hz), 7.66 (ddd, 1H, 0.5/1/8 Hz) 7.92 (d, 1H,2.5 Hz), 10.16 (s, 1H, lactam NH), 11.63 (s, 1H, indole NH); $^{13}$C-nmr(DMSO-d$_6$, 75 MHz): 6(ppm)=31.5, 108.3, 111.3, 115.4, 117.9, 119.1, 122.4, 124.0, 124.6, 126.2, 128.7, 130.2, 130.8, 134.4, 137.4, 171.0; C$_{16}$H$_{11}$BrN$_2$O (327.2); Calcd. C 58.7, H 3.39, N 8.6; Found C 58.6, H 3.28, N 8.7.

Example 13

This example describes the synthesis of 7,12-dihydro-2,3-dimethoxy-9-trifluormethyl-indolo[3,2-d][1]benzazepin-6(5H)-one.

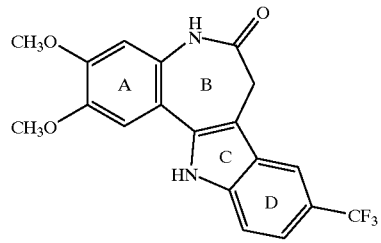

The synthesis was performed corresponding to the general procedure described above in Example 2 from 7,8-dimethoxy-1H-1-benzazepin-2,5(3H, 4H1)-dione (235 mg, 1 mmol) and 4-trifluormethylphenylhydrazine (264 mg, 1.5 mmol), yielding 38% pale yellow crystals, m.p.>330° C.; ir (KBr): 3240 (NH), 1635 cm$^{-1}$ (C=O); $^1$H-nmr (DMSO-d$_6$, 400 MHz): 5 (ppm)=3.55 (s, 2H, CH$_2$), 3.81 (s, 3H, OCH$_3$), 3.88 (s, 3H, OCH$_3$), 6.90 (s, 1H), 7.31 (s, 1H), 7.43 (dd, 1H, 1.0/8.6 Hz), 7.61 (d, 1H, 8.6 Hz), 8.08 (s, 1H), 9.87 (s, 1H, lactam-NH), 11.96 (s, 1H, indole-NH); $^1$C-nmr (DMSO-d$_6$, 100.6 MHz): 68(ppm)=31.2, 55.5, 55.7, 106.1, 106.8,106.8, 109.5, 111.8, 114.3, 115.4 (q, J$_{C,F}$=4.4 Hz), 117.9 (q, J$_{C,F}$=3.7 Hz), 120.0, 125.9, 129.6, 135.2, 138.5, 145.3, 149.1, 170.7; C$_{19}$H$_{15}$F$_3$N$_2$O$_3$ (376.35); Calcd. C 60.64, H 4.02, N 7.45; Found C 60.70, H 4.07, N 7.46.

Example 14

This example describes the synthesis of 2-bromo-7,12-dihydro-9-trifuormethyl-indolo[3, 2-d][1]benzazepin-6(5H)-one.

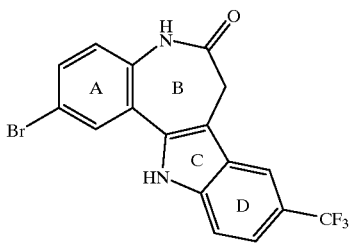

The synthesis was accomplished according to the general procedure described above in Example 2 using 7-bromo-1H-[1]benzazepin-2,5(3H, 4H)-dione (254 mg, 1 mmol) and 4-trifluormethylphenylhydrazine (264 mg, 1.5 mmol), yielding 51% colorless crystals from ethanol/toluene, m. p. >330° C.; ir (KBr): 3300 (NH), 1635 cm$^{-1}$ (C=O); $^1$H-nmr (DMSO-d$_6$, 400 MHz): δ (ppm)=3.64 (s, 2H, CH$_2$), 7.23 (d, 1H, 9.2 Hz), 7.48 (dd, 1H, 1.0/8.7 Hz), 7.58–7.63 (m, 2H), 7.95 (d, 1H, 2.0 Hz), 8.15 (s, 1H), 10.25 (s, 1H, lactam-NH), 12.15 (s, 1H, indole-NH); $^{13}$C-nmr (DMSO-d$_6$, 100.6 MHz): δ (ppm)=31.2, 109.2, 112.2, 115.6,116.1 (q, J$_{C,F}$=4.1 Hz), 118.7 (q, J$_{C,F}$=3.7 Hz), 124.1, 124.2, 124.3, 125.7,129.1, 131.1, 133.2, 134.8, 134.9, 138.8, 171.2; C$_{17}$H$_1$OBrF$_3$N$_2$O (395.19); Calcd. C 51.67, H 2.55, N 7.09, Br 20.22; Found C 51.62, H 2.58, N 7.04, Br 20.12.

Example 15

This example describes the synthesis of 9-bromo-7,12-dihydro-5-methyloxycarbonylmethyl-indolo[3, 2-d][1]benzazepin-6(5H)-one.

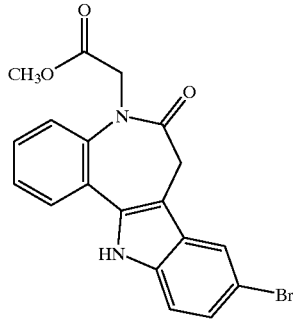

A solution of 9-bromo-7,12-dihydro-indolo[3,2-d][11]benzazepin-6(5H1)-one (327 mg, 1 mmol) in THF (35 mL) was refluxed with sodium hydride (24 mg, 1 mmol, 60% suspension in white oil) for 1.5 hours. Bromoacetic acid ethyl ester (153 mg, 1 mmol) was added and refluxing was continued for 5 hours. After cooling to room temperature, water (50 mL) was added. The mixture was extracted three times with dichloromethane (20 mL, respectively). The combined organic layers were dried with sodium sulfate and evaporated to furnish a residue, which was recrystallized from ethanol to yield 46% colorless crystals, m. p. 240° C., ir (KBr): 3340 (NH), 1750, 1655 cm$^{-1}$ (C=O); $^1$H-nmr (DMSO-d$_6$, 400 MHz): 3 (ppm)=3.10 (br s, lH, azepine-CH), 3.63 (s, 3 H, COOCH$_3$), 3.94 (br s, 11H, azepine-CH), 4.43 (br s, 2H, CH$_2$COOCH$_3$), 7.29 (dd, 1H, 1.8/8.4 Hz), 7.40–7.43 (m, 2H), 7.46–7.52 (m, 2H), 7.72–7.74 (m, 1H), 7.93 (d, 1H, 1.5 Hz), 11.94 (s, 1 H, NH); $^{13}$ C-nmr (DMSO-d$_6$, 100.6 MHz): 3 (ppm) 30.9, 51.8, 52.2, 108.7, 111.7, 113.5, 120.5, 123.9, 124.6, 125.1, 125.3, 127.2, 127.8, 128.6, 133.8, 135.9, 139.4, 169.7, 170.4; C$_{19}$H$_{15}$BrN$_2$O$_3$ (399.25); Calcd. C 57.16, H 3.79, N 7.02, Br 20.01; Found C 57.07, H 3.90, N 6.99, Br 20.02.

Example 16

This example describes the synthesis of 9-bromo-7,12-dihydro-12-(2-hydroxyethyl)-indolo[3,2-d][1]benzazepin-6(5H)-one.

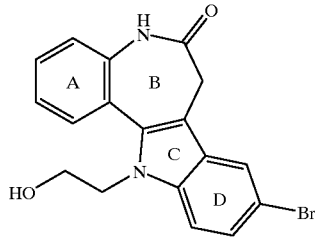

A solution of 9-bromo-12-methyloxycarbonylmethyl-7,12-dihydro-indolo[3,2-d][1]benzazepin-6 (5H)-one (399 mg, 1 mmol) in THF (80 mL) was added by means of a dropping funnel to a stirred suspension of lithium alumino hydride (19 mg, 0.5 mmol) in THF (10 mL). After the addition was complete, the mixture was refluxed for 2 hours. An additional portion of lithium alumino hydride (19 mg, 0.5 mmol) was added and refluxing was continued for 1 hour. After cooling to room temperature, water was cautiously added until the hydrogen evolution was finished. (Caution: the evolved hydrogen is flammable and may ignite!) A precipitate of aluminium hydroxide was formed, which was redissolved by dropwise addition of 25% sulfuric acid. The solution was extracted twice with dichloromethan (20 mL, respectively). The combined organic layers were dried with sodium sulfate and evaporated. The residue was recrystallized from ethanol to yield 48% colorless crystals, m.p. 267° C.; ir (KBr): 3420, 3340 (OH), 3260 (NH), 1650 cm$^{-1}$ (C=O); $^1$H-nmr (DMSO-d$_6$, MHz): δ (ppm)=3.05(br s, 1H, azepin-CH), 3.35 (br s, 1H, azepine-CH, overlapping the H$_2$O-signal), 3.68–3.75 (br m, 2H, CH$_2$-N), 4.32–4.35 (m, 2H, O—CH$_2$), 5.02 (t, 1H, 5.3 Hz, OH), 7.29–7.35 (m, 3H), 7.42–7.46 (m, 1H), 7.59 (d, 1H, 8.6 Hz), 7.94 (d, 1H, 2.0 Hz), 7.97 (d, 1H, 7.5 Hz), 10.01 (s, 1H, NH); $^{13}$C-nmr (DMSO-d$_6$, 100.6 MHz): δ (ppm)=31.1, 46.6, 59.5, 109.8, 112.1, 113.0, 120.3, 121.7, 122.9, 123.5, 124.4, 127.2, 128.4, 128.8, 135.2, 136.7, 137.2, 172.5; C$_{18}$H$_{15}$BrN$_2$O$_2$ (371.24); Calcd. C 58.24, H 4.07, N 7.55, Br 21.52; Found C 58.17, H 4.35, N 7.47, Br 21.68.

Example 17

This example describes the synthesis of 9-bromo-7,12-dihydro-12-methyl-indolo[3,2-d][1]benzazepin-6(5H)-one.

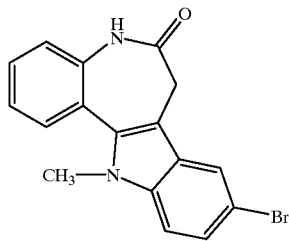

The synthesis was performed according to the general procedure described above in Example 5 using iodomethane (1420 mg, 10 mmol) to furnish 28% of yellowish crystals, m. p. 313° C. from ethanol/toluene; ir (KBr): 3170 (NH), 1665 cm$^{-1}$ (C=O); $^1$H-nmr (DMSO-d$_6$, 400 MHz): δ (ppm)=3.08–3.99 (very broad signal, 2H, CH$_2$, overlapping the H$_2$O-signal) 3.84 (s, 3H, CH$_3$), 7.30–7.33 (m, 2H), 7.36 (dd, 1H, 1.6/6.9 Hz), 7.43–7.47 (m, 1H), 7.54 (d, 1H, 7.1 Hz), 7.74 (dd, 1H, 1.1/6.4 Hz), 7.95 (d, 1H, 1.5 Hz), 10.06 (s, 1H, NH); $^{13}$C-nmr (DMSO-d$_6$, 100.6 MHz): δ(ppm)= 31.2, 31.8,109.3, 112.1, 112.3, 120.4, 121.4, 122.8, 123.4, 124.6, 126.8, 128.5, 128.8, 135.1, 136.6, 137.4, 172.3; C$_{17}$H$_{13}$BrN$_2$O (341.21); Calcd. C 59.84, H 3.84,N 8.21, Br 23.42; Found C 59.63, H 3.91, N 8.10, Br 23.09.

Example 18

This example describes the synthesis of 9-bromo-7,12-dihydro-indolo[3,2-d][1]benzazepine-6(5H)-thione.

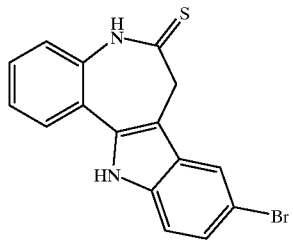

A solution of 9-bromo-7,12-dihydroindolo[3,2-d]-1-benzazepin-6(5H)-one (327 mg, 1 mmol) in THF (30 mL) was stirred under nitrogen at 50° C. Phosphorus pentasulfide (250 mg, 1,12 mmol) and sodium hydrogencarbonate (370 mg, 4.4 mmol) were added successively. After refluxing for 3 hours under nitrogen, the mixture is allowed to cool to room temperature and then poured onto crushed ice (50 g). The mixture was then stirred until the ice is molten, and the precipitate which formed was filtered off with suction, washed with water and recrystallized from ethanol/toluene yielding 67% pale yellow crystals, m. p. >330°, ir (KBr): 3430, 3140 cm$^{-1}$ (NH); $^1$H-nmr (DMSO-d$_6$, 400 MHz): δ (ppm)=3.91 (s, 2H, CH$_2$), 7.30 (dd, 1H, 1.5/8.6 Hz), 7.39–7.45 (m, 4H), 7.79 (d, 1H, 7.1 Hz), 7.86 (d, 1H, 1.5 Hz), 11.92 (s, 1H, NH), 12.07(s, 1H, NH); 13C-nmr (DMSO-d$_6$, 100.6 MHz): δ (ppm)=39.6, 109.3, 111.8, 113.5, 120.3, 123.1, 123.7,124.8, 125.5, 126.9, 127.8, 128.1, 133.3, 136.2, 136.2, 200.2; C$_{16}$H$_{11}$BrN$_2$S (343.24); Calcd. C 55.99, H 3.23, N 8.16, Br 23.28, S 9.34; Found C 55.81, H 3.28, N 8.00, Br 22.42, S 9.51.

Example 19

This example describes the synthesis of 8-hromo-6,11-dihydro-thieno[3 ', 2 ':2,3]azepino[4,5-b] indol-5(4H)-one.

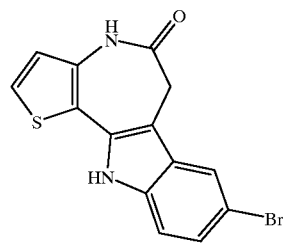

A suspension of 4-bromophenylhydrazine hydrochloride (391 mg; 1.75 mmol) and sodium acetate (144 mg, 1.75 mmol) in glacial acetic acid (2.5 mL) was added dropwise to a suspension of 4H-thieno[3,2-b]azepin-5,8(6H,7H)-dione (264 mg, 1.5 mmol) in glacial acetic acid (2.5 mL). After stirring for 1 hour at 70° C. the mixture was allowed to cool to room temperature. Concentrated sulfuric acid (0.125 mL) was added and the mixture is stirred for 1.5 hours at 70° C. After cooling to room temperature, the mixture is poured into a 25% aqueous sodium acetate solution (25 mL). A precipitate was formed, which was filtered with suction and recrystallized from ethanol/toluene to yield 26% of metallic shimmering crystals, mp>280° C. (decomposition above 288° C.). ir (KBr): 3400 (NH), 1650 cm$^{-1}$ (C=O); $^1$H-nmr (DMSO-d$_6$, 400 MHz): δ (ppm)=3.54 (s, 2H, CH$_2$), 6.94 (d, 1H, 5 Hz), 7.24 (dd, 1lH, 2.0/8.6 Hz), 7.34 (d, 1H, 8.6 Hz), 7.62 (d, 1H, 5 Hz), 7.86 (d, 1H, 1.5 Hz), 10.37 (s, 1H, lactam-NH), 11.73 (s, 1H, indole-NH); $^{13}$C-nmr (DMSO-d$_6$, 100.6 MHz): δ (ppm)=32.0, 104.5, 111.9, 113.2, 115.7,120.0, 123.1, 124.2,125.4, 128.3, 130.8, 135.1, 136.3, 168.4; C$_{14}$H$_9$BrN$_2$O S (333.21); Calcd. C 50.46, H 2.72, N 8.41, S 9.62; Found C 50.39, H 2.90, N 8.32, S 9.53.

Example 20

This example describes the synthesis of 9-nitro-7,12-dihydro-indolo[3,2-d][1]benzazepin-6(5H)-one.

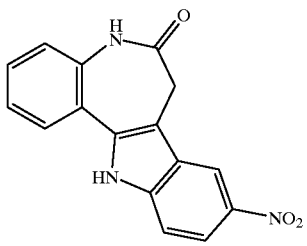

1H-[1]benzazepine-2,5(3H,4H)-dione (175 mg, 1 mmol), 4-nitro-phenylhydrazine hydrochloride (284 mg, 1.5 mmol), and sodium acetate (123 mg, 1.5 mmol) were stirred in glacial acetic acid (10 mL) for 1 hour at 70° C. After addition of concentrated sulfuric acid (0.1 mL) stirring was continued at 70° C. After 1 hour and 2 hours of stirring further portions of concentrated sulfuric acid (0.1 mL, respectively) were added. After a total reaction time of 4 hours the mixture was cooled to room temperature and poured into a 5% aqueous sodium acetate solution (20 mL). The precipitate was filtered off with suction and crystallized from ethanol/toluene to yield 33% yellow crystals, mp. >330° C.; ir (KBr): 3380 (NH), 1660 (C=O); $^1$H-nmr (DMSO-d$_6$, 400 MHz): δ (ppm)=3.65 (s, 2H, CH$_2$), 7.29–7.34 (m, 2H), 7.43–7.47 (m, 1H), 7.60 (d, 1H, 9.2 Hz), 7.77–7.79 (m, 1H), 8.08 (dd, 1H, 8.6/2.0 Hz), 8.74 (d, 1H, 2.0 Hz), 10.22 (s, 1H, lactam NH), 12.39 (s, 1H, indole NH); $^{13}$C-nmr (DMSO-d$_6$, 125.8 MHz): δ (ppm) =31.2, 109.6,111.8, 115.3, 117.3, 121.7,122.3, 123.7,125.8, 127.0, 129.0, 135.9, 136.1, 140.3, 140.8, 171.2; $C_{16}H_{11}N_3O_3$ (293.29); Calcd. C 65.5, H 3.8, N 14.3; Found C 65.5, H 3.9, N 14.5.

In vitro time course assays were performed with this compound in order to determine the concentration and duration of drug application necessary to inhibit cell proliferation. Four cell lines (CoLo-205, HL-60 TB, A-498, UO-31) were cultured in media containing the compound for incremental times, then were switched to compound-free media for the rest of the observation time. The results (illustrated in FIGS. 31 and 32 of PCT/US99/13579) indicate that this particular compound causes total inhibition of growth (as measured by GI$_{50}$, TGI and LC$_{50}$) at 2–5 μM and that short exposures were sufficient for maximum inhibition. Cells exposed to the compound for 48 hours required a lower concentration of 1–3 μM to achieve total growth inhibition. The data are effective in determining a dosing schedule that achieves maximum cell growth inhibition, i.e., a plasma or blood level concentration of 2–5 μM compound when exposed for 45 minutes once per day.

Initial experiments to determine if these exposures are achievable in animals were done in Sprague Dawley rats. A single i.v. dose of this compound dissolved in DMSO was given to two animals, one at 5 mg/kg and one at 10 mg/kg. Plasma concentrations of the parent compound were determined by HPLC assay and are listed in the table. At 5 mg/kg the half life in the plasma was 46 minutes, clearance was 16 mL/min/kg, and concentrations in excess of 2 μM were determined for over two hours. At 10 mg/kg the half life in plasma was 66 minutes, the clearance was 14 mL/min/kg and concentrations in excess of 2 μM were maintained for over three hours.

TABLE 3

| Time (min) | Plasma Concentration (μM) 10 mg/kg dose | Plasma Concentration (μM) 5 mg/kg dose |
| --- | --- | --- |
| 3 | 54.0 | 22.9 |
| 6 | 32.3 | 17.8 |
| 9 | 24.6 | 14.8 |
| 12 | 21.2 | 12.9 |
| 15 | 18.9 | 12.2 |
| 20 | 17.5 | 10.4 |
| 30 | 15.6 | 8.7 |
| 60 | 14.2 | 6.4 |
| 90 | 9.9 | 4.9 |
| 120 | 7.5 | 2.6 |
| 180 | 3.1 | 0.9 |

Example 21

This example describes the synthesis of 2-bromo-9-nitro-7,12-dihydro-indolo[3,2-d][1]benzazepin-6(5H)-one.

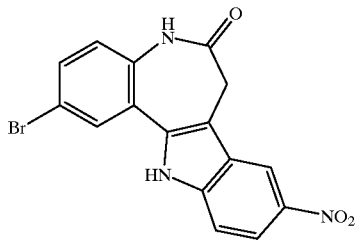

7-bromo-1H-[1]benzazepine-2,5(3H,4H)-dione (254 mg, 1 mmol), 4-nitro-phenylhydrazin hydrochloride (284 mg, 1.5 mmol), and sodium acetate (123 mg, 1.5 mmol) were stirred in glacial acetic acid (10 mL) for 1 hour at 70° C. After cooling to room temperature, the mixture was poured into 5% aqueous sodium acetate solution (20 mL). The precipitate was filtered off with suction, washed with water, and crystallized from ethanol to furnish 52% yellow crystals of precursor, 7-bromo-5-(4-nitro-phenylhydrazono)-4,5-dihydro-]H-[1]benzazepin-2(3H)-one, mp. 300° C. (dec.); ir (KBr): 3220 (NH), 1670 (C=O); $^1$H-nmr (DMSO-d$_6$, 400 MHz): δ (ppm) 2.56–2.59 and 3.02–3.06 (m, AA'XX', 4H, CH$_2$—CH$_2$), 6.99 (d, 1H, 8.1 Hz), 7.33 (d, 2H, 9.2 Hz), 7.56 (dd, 1H, 8.7/2.6 Hz), 7.75 (d, 1H, 2.0 Hz), 8.16 (d, 2H, 9.6 Hz), 9.87 (s, 1H, NH), 10.19 (s, 1H, NH); $^{13}$C-nmr(DMSO-d$_6$, 100.6 MHz): 6(ppm)=29.7,30.5, 112.4,116.2, 124.0, 125.8, 131.6, 132.1, 132.3, 136.8, 139.1, 147.1, 150.8, 172.7; $C_{16}H_{13}BrN_4O_3$ (389.22); Calcd. C 49.4, H 3.4, N 14.4, Br 20.5; Found C 49.1, H 3.4, N 14.1, Br 20.2.

7-bromo-5-(4-nitro-phenylhydrazono)-4,5-dihydro-1H-[1]benzazepin-2(3H)-one (389 mg, 1 mmol) was refluxed in diphenyl ether (20 mL) for 2 hours under nitrogen. After cooling to room temperature, hexane (50 mL) was added. The precipitate was filtered off with suction, washed with hexane and crystallized from ethanol/toluene to furnish 35% yellow-brown crystals, mp. >330° C.; ir (KBr): 3310 (NH), 1670 (C=O); $^1$H-nmr (DMSO-d$_6$, 400 MHz): δ (ppm)=3.69 (s, 2H, CH$_2$), 7.23 (d, 1H, 8.6 Hz), 7.59–7.64 (m, 2H), 7.96 (d, 1H, 2.0 Hz), 8.09 (dd, 1H, 9.1/2.0 Hz), 8.77 (d, 1H, 1.5 Hz), 10.32 (s, 1H, lactam NH), 12.46 (s, 1H, indole NH); $^{13}$C-nmr(DMSO-d$_6$, 100.6 MHz): 8(ppm)=31.2, 110.5, 111.9, 115.58, 115.62, 117.7,123.6, 124.3, 125.6, 129.1, 131.4, 134.6, 135.1, 140.4, 140.9, 171.0; $C_{16}H_{10}BrN_3O_3$ (372.19); Calcd. C 51.6, H 2.7, N 11.2, Br 21.5; Found C 51.5, H 3.0, N 10.8, Br 21.3.

Example 22

This example describes the synthesis of 2,3-dimethoxy-9-nitro-7,12-dihydro indolo[3,2-d][]]benzazepin-6(5H)-one.

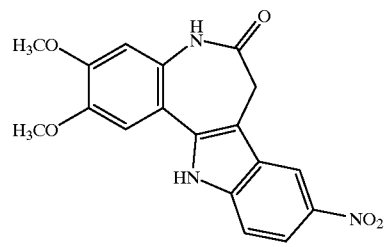

7,8-dimethoxy-1H-[1]benzazepine-2,5(3H,4H)-dione (235 mg, 1 mmol), 4-nitro-phenylhydrazine hydrochloride (569 mg, 3 mmol) and sodium acetate (246 mg, 3 mmol) were stirred in glacial acetic acid (10 mL) for 1 hour at 70° C. After cooling to room temperature, the mixture was poured into 5% aqueous sodium acetate solution (20 mL). The precipitate was filtered off with suction, washed with water, and crystallized from ethanol to furnish 60% yellow crystals of precursor 7,8-dimethoxy-5-(4-nitro-phenylhydrazono)-4,5-dihydro-]H-[1]benzazepin-2(3H)-one, mp. 286° C. (dec.); ir (KBr): 3260/3180 (NH), 1680 (C=O); $^1$H-nmr (DMSO-$d_6$, 400 MHz): δ (ppm)=2.53–2.56 and 2.99–3.03 (m, AA'XX', 4H, $CH_2$—$CH_2$), 3.77 (s, 3H, $OCH_3$), 3.81 (s, 3H, $OCH_3$), 6.65 (s, 1H), 7.20 (s, 1H), 7.32 (d, 2H, 9.2 Hz), 8.13 (d, 2H, 9.2 Hz), 9.53 (s, 1H, NH), 10.06 (s, 1H, NH); $^{13}$C-nmr (DMSO-$d_6$, 100.6 MHz): δ (ppm)=29.9, 30.7, 55.5, 55.9, 105.9, 112.1, 122.0, 125.8, 131.1, 138.6, 145.3, 148.6, 149.8, 151.1, 172.8 (one signal missing due to peak overlapping); $C]_8HI8N_4O_5$ (370.38); Calcd. C 58.4, H 4.9, N 15.1; Found C 57.8, H 4.9, N 14.8.

7,8-dimethoxy-5-(4-nitro-phenylhydrazono)-4,5-dihydro-1H-[1]benzazepin-2(3H)-one (370 mg, 1 mmol) was refluxed in diphenyl ether (20 mL) for 2 hours under nitrogen. After cooling to room temperature, hexane (50 mL) was added. The precipitate was filtered off with suction, washed with hexane and crystallized from ethanol/toluene, yielding 63% yellow-brown crystals, mp. >330° C.; ir (KBr): 3340 (NH), 1660 (C=O); $^1$H-nmr (DMSO-$d_6$, 400 MHz): 6 (ppm)=3.58 (s, 2H, $CH_2$), 3.81 (s, 3H, $OCH_3$), 3.88 (s, 3H, $OCH_3$), 6.90 (s, 1H), 7.31 (s, 1H), 7.59 (d, 1H, 9.2 Hz), 8.05 (dd, 1H, 8.9/2.3 Hz), 8.69 (d, 1H, 2.0 Hz), 9.94 (s, 1H, lactam NH), 12.32 (s, 1H, indole NH); $^{13}$C-nmr (DMSO-$d_6$, 100.6 MHz): δ (ppm)=31.2, 55.5, 55.8,106.0, 108.0, 109.3, 111.5, 113.8, 114.8, 116.9, 125.9, 129.9, 136.6, 140.1, 140.7, 145.3, 149.3, 170.5; $C_{18}H_{15}N_3O_5$ (353.35); Calcd. C 61.2, H 4.3, N 11.9; Found C 60.9, H 4.4, N 11.8.

Example 23

This example describes the synthesis of 2-iodo-9-trifluoromethyl-7,12-dihydro-indolo[3,2-d][1]benzazepin-6(5H)-one.

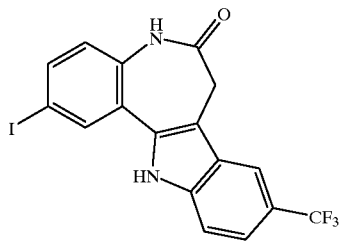

A solution of methyl succinyl chloride (3011 mg, 20 mmol) in toluene (10 mL) was added dropwise by means of a dropping funnel to a mixture of 2-amino-5-iodobenzoic acid methyl ester (4156 mg, 15 mmol), pyridine (1.7 mL), and toluene (10 mL) with stirring and cooling. The resulting suspension was refluxed for 3 hours. After cooling to room temperature, water (15 mL) was added. The organic layer was separated and washed successively with 10% hydrochloric acid (5 mL) and 5% aqueous sodium carbonate solution (5 mL). Subsequently, the organic layer was dried over sodium sulfate and evaporated. The residue was crystallized from ethanol to yield 72% colorless crystals of precursor 5-iodo-2-[(4-methoxy-1,4-dioxobutyl)amino]-benzoic acid methyl ester, mp. 133° C.; ir (KBr): 3250 (NH), 1730/1720/1680 (C=O); $^1$H-nmr (DMSO-$d_6$, 400 MHz): δ (ppm)=2.59–2.69 (m, AA'BB', 4H, $CH_2$—$CH_2$), 3.60 (s, 3H, $OCH_3$), 3.85 (s, 3H, $OCH_3$), 7.91 (dd, 1H, 8.7/2.0 Hz), 7.99 (d, 1H, 8.7 Hz), 8.14 (d, 1H, 2.0 Hz), 10.53 (s, 1H, NH); $^{13}$C-nmr (DMSO-$d_6$, 100.6 MHz): δ (ppm)=28.3, 31.4, 51.3, 52.5, 86.3, 120.1, 123.2, 138.3, 138.8, 141.9, 166.1, 170.1, 172.5; $C_{13}H_{14}INO_5$ (391.17); Calcd. C 39.9, H 3.6, N 3.6, 132.4; Found C 39.9, H 3.7, N 3.6, 132.4.

Potassium hydride (4 g, 100 mmol) was washed three times with toluene (20 mL) under nitrogen, then suspended in toluene (20 mL). A solution of 5-iodo-2-[(4-methoxy-1,4-dioxobutyl)amino]-benzoic acid methyl ester (7823 mg, 20 mmol) in N,N-dimethylformamide (9 mL) and toluene (80 mL) was added dropwise by means of a dropping funnel to the potassium hydride suspension with cooling and stirring under a nitrogen atmosphere. After the evolution of hydrogen had ceased, the mixture was warmed to 80° C. and stirred continuously for 3 hours. After cooling to room temperature, glacial acetic acid (6 mL) and then water (60 mL) were cautiously added dropwise with stirring. The resulting suspension was stirred in an ice bath for 15 minutes. A precipitate formed, which was filtered off with suction and washed with water and hexanes. Crystallization from ethanol/toluene yields 41% colorless crystals of precursor 5-hydroxy-7-iodo-2-oxo-2, 3-dihydro-JH-[]]henzazepine-4-carbonic acid methyl ester, mp. 271° C.; ir (KBr): 3150 (NH), 1680/1670 (C=O); $^1$H-nmr (DMSO-$d_6$, 400 MHz): 6 (ppm)=2.94 (s, 2H, $CH_2$), 3.84 (s, 3H, $OCH_3$), 6.99 (d, 1H, 8.1 Hz), 7.85 (dd, 1H, 8.6/2.0 Hz), 8.04 (d, 1H, 2.0 Hz), 10.42 (s, 1H, NH), 12.34 (br. s, 1H, OH); $^{13}$C-nmr (DMSO-$d_6$, 100.6 MHz): δ (ppm) 30.6, 52.5, 87.2, 96.4, 123.7,126.7, 136.1, 137.6, 140.1, 164.4, 170.5, 171.7; $C_{12}H_{10}INO_4$ (349.12); Calcd. C 40.1, H 2.8, N 3.9, 134.4; Found C 40.1, H 3.0, N 4.0, I 34.1.

Water (0.5 mL) was added to a solution of 5-hydroxy-7-iodo-2-oxo-2,3-dihydro-1H-[1]benzazepine-4-carboxylic acid methyl ester (349 mg, 1 mmol) in dimethyl sulfoxide (10 mL). The mixture was stirred under nitrogen at 150° C. Water (0.5 mL) was added after 1 hour and 2 hours of stirring, respectively. After a total reaction time of 3 hours the mixture was cooled to room temperature and poured into water (20 mL). A solid precipitated from the solution upon standing (12 hours at 6° C.) and was filtered off with suction and crystallized from ethanol to yield 78% colorless crystals of precursor 7-iodo-1H-[1]benzazepine-2,5(3H,4H)-dione, mp. 217° C.; ir (KBr): 3180 (NH), 1650 (C=O); $^1$H-nmr (DMSO-$d_6$, 400 MHz): δ (ppm) =2.66–2.69 und 2.89–2.92 (m, AA'XX', 4H, $CH_2$—$CH_2$), 6.97 (d, 1H, 8.6 Hz), 7.86 (dd, 1H, 8.6/2.0 Hz), 8.05 (d, 1H, 2.0 Hz), 10.17 (s, 1H, NH); $^{13}$C-nmr (DMSO-$d_6$, 100.6 MHz): δ (ppm) =28.9, 37.7, 86.9, 123.9, 128.3, 138.2, 138.9, 142.0, 173.3, 197.3; $CIoH_8INO_2$ (301.08); Calcd. C 39.9, H 2.7, N 4.7,I 42.2; Found C 39.9, H 2.7, N 4.6,I 42.3.

Next, a mixture of 7-iodo-1H-[1]benzazepine-2,5(3H,4H)-dione (301 mg, 1 mmol), 4-trifluoromethyl-phenylhydrazine (264 mg, 1.5 mmol) and glacial acetic acid (10 mL) was stirred at 70° C. for 1 hour. Concentrated sulfuric acid (0.1 mL) was added and stirring continued for 1 hour. The mixture was then cooled to room temperature and poured into 5% aqueous sodium acetate solution (20 mL). The precipitate was filtered off with suction, washed with water and crystallized from ethanol to yield 50% yellow crystals, mp. >330° C.; ir (KBr): 3320 (NH), 1645 (C=O); $^1$H-nmr (DMSO-$d_6$, 400 MHz): δ (ppm)=3.63 (s, 2H, $CH_2$), 7.07 (d, 1H, 8.6 Hz), 7.47 (dd, 1H, 8.6/1.5 Hz), 7.61 (d, 1H, 8.6 Hz), 7.73 (dd, 1H, 8.6/2.0 Hz), 8.10 (d, 1H, 2.0 Hz), 8.16 (s, 1H), 10.24 (s, 1H, lactam NH), 12.14 (s, 1H, indole NH); $^{13}$C-nmr (DMSO-$d_6$, 100.6 MHz): δ (ppm)= 31.2, 87.7, 109.1, 112.2, 116.1 (q, $J_{C,F}$=4.1 Hz), 116.2, 118.6

(q, JCF=3.1 Hz), 120.2 (q, JCF=32 Hz), 124.3, 125.4 (q, $J_{C,F}$=272 Hz), 125.6, 133.1, 134.9, 135.4, 136.8, 138.8, 171.2; $C_{17}H_{10}F_3IN_2O$ (442.19); Calcd. C 46.2, H 2.3, N 6.3,128.7; Found C 46.0, H 2.4, N 6.3, I 28.7.

Example 24

This example describes the synthesis of 3-(6-oxo-9-trifluoromethyl-5, 6, 7,12-tetrahydro-indolo[3,2-d][1]benzazepin-2-yl)-acrylonitrile.

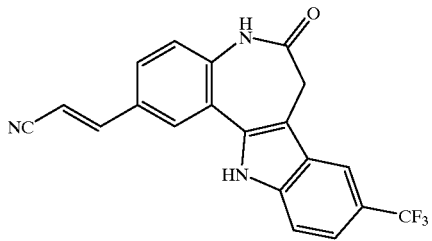

2-iodo-9-trifluoromethyl-7,12-dihydro-indolo[3,2-d][1]benzazepin-6(5H1)-one (442 mg, 1 mmol), acrylonitrile (531 mg, 10 mmol), triethylamine (121 mg, 1.2 mmol), palladium(II)-acetate (45 mg, 0.2 mmol), and triphenylphosphine (52 mg, 0.2 mmol) were stirred in N,N-dimethylformamide (30 mL) under nitrogen at 150° C. for about 8 hours, until the starting material 2-iodo-9-trifluoromethyl-7,12-dihydro-indolo[3,2-d][1]benzazepin-6(5H)-one was no longer detectable by thin layer chromatography (silica gel, toluene/acetone 1:1). The reaction mixture was then filtered hot and the resulting solution evaporated. The residue was crystallized from ethanol (ethanol/toluene may also be used). Crystallization from ethanol yielded 43% yellow crystals, mp. >330° C.; ir (KBr): 3310/3200 (NH), 2220 (CN), 1670 (C=O); $^{1}$H-nmr (DMSO-$d_6$, 400 MHz): δ (ppm)=3.67 (s, 2H, $CH_2$), 6.48 (d, 11H, 16.8 Hz), 7.31 (d, 1H, 8.7 Hz), 7.49 (dd, 1H, 8.7/1.0 Hz), 7.64 (d, 1H, 8.6 Hz), 7.71 (d, 1H, 16.8 Hz and dd, 1H, 8.6/2.0 Hz; overlapping signals), 8.05 (d, 1H, 1.5 Hz), 8.17 (s, 1H), 10.41 (s, 1H, lactam NH), 12.11 (s, 1H, indoleNH); $^{13}$C-nmr(DMSO-$d_6$, 100.6MHz): o(ppm)=31.3, 96.1, 108.6, 112.1, 116.1 (q, JCF=4.1 Hz), 118.6 (q, $J_{C,F}$=3.0 Hz), 118.8, 120.2 (q, $J_{C,F}$=32 Hz), 122.2, 122.5, 125.4 (q, $J_{C,F}$=271 Hz), 125.8, 126.9, 127.6, 129.1, 133.9, 137.7, 138.8, 149.5, 171.2; $C_2OH_{12}F_3N_3O$ (367.35); Calcd. C 65.4, H 3.3, N 11.4; Found C 65.0, H 3.3, N 11.2.

Example 25

This example describes the synthesis of 3-(6-oxo-9-trifluoromethyl-5, 6, 7,12-tetrahydro-indolo[3,2-d][1]benzazepin-2-yl)-propionitrile.

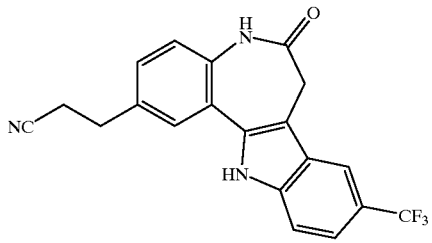

A mixture of 3-(6-oxo-9-trifluoromethyl-5,6,7,12-tetrahydro-indolo[3,2-d][1]benzazepin-2-yl)-acrylonitrile (367 mg, 1 mmol), magnesium turnings (972 mg, 40 mmol), and methanol (50 mL) was refluxed for 1 hour. After cooling to room temperature, the mixture was neutralized by addition of 10% aqueous hydrochloric acid. The mixture was then extracted five times with dichloromethane (portions of 20 mL, respectively). The combined organic layers were dried by means of sodium sulfate and evaporated. Crystallization of the residue from ethanol affords 51% light yellow crystals, mp. 286° C.; ir (KBr): 3340 (NH), 2240 (CN), 1660 (C=O); $^{1}$H-nmr (DMSO-$d_6$, 400 MHz): o (ppm)=2.88–2.99 (m, AA'BB', 4H, $CH_2$—$CH_2$), 3.61 (s, 2H, $CH_2$), 7.23 (d, 1H, 8.1 Hz), 7.36 (dd, 1H, 8.4/1.8 Hz), 7.47 (dd, 1H, 8.6/1.6 Hz), 7.63 (d, 1H, 8.6 Hz), 7.69 (d, 1H, 1.6 Hz), 8.14 (s, 1H), 10.14 (s, 1H, lactam NH), 12.06 (s, 1H, indole NH); $^{13}$C-nmr (DMSO-$d_6$, 100.6 MHz): δ (ppm)=18.0, 30.0, 31.3, 108.4, 112.1, 115.9 (q, $J_{C,F}$=4.1 Hz), 118.3 (q, JCF=3.1 Hz), 120.0 (q, JC=32 Hz), 120.2, 122.1, 122.4, 125.5 (q, JCF=270 Hz), 125.8, 126.8, 128.7, 134.2, 134.4, 134.6, 138.7, 171.2; $C_{20}H_4F_3N_3O$ (369.36); Calcd. C 65.0, H 3.8, N 11.4; Found C 64.5, H 4.0, N 11.3.

Example 26

This example describes the synthesis of 2-(3-oxo-1-butenyl)-9-trifluoromethyl-7,12-dihydro-indolo[3, 2-d][1]benzazepin-6(5H)-one.

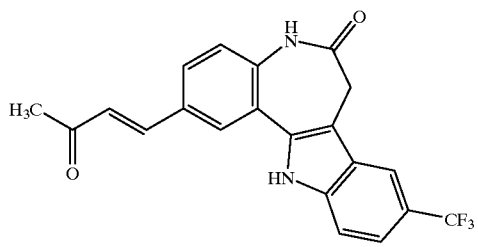

2-iodo-9-trifluoromethyl-7,12-dihydro-indolo[3,2-d][1]benzazepin-6(5H)-one (442 mg, 1 mmol), methyl vinyl ketone (701 mg, 10 mmol), triethylamine (121 mg, 1.2 mmol), palladium(II)-acetate (45 mg, 0.2 mmol), and triphenylphosphine (52 mg, 0.2 mmol) were stirred in N,N-dimethylformamide (30 mL) under nitrogen at 150° C. for about 4 hours, until the starting material 2-iodo-9-trifluoromethyl-7,12-dihydro-indolo[3,2-d][1]benzazepin-6(5H)-one was no longer detectable by thin layer chromatography (silica gel, toluene/acetone 1:1). The reaction mixture was then filtered hot and the resulting solution evaporated. The residue was crystallized from ethanol (ethanol/toluene may also be used), yielding 48% yellow crystals, mp. >330° C.; ir (KBr): 3270 (NH), 1670/1655 (C=O); $^{1}$H-nmr (DMSO-$d_6$, 400 MHz): δ (ppm)=2.37 (s, 3H, $CH_3$), 3.68 (s, 2H, $CH_2$), 6.90 (d, 1H, 16.3 Hz), 7.31 (d, 1H, 8.1 Hz), 7.49 (d, 1H, 8.6 Hz), 7.64 (d, 1H, 8.6 Hz), 7.69 (d, 1H, 16.3 Hz), 7.75 (dd, 1H, 8.1/1.5 Hz), 8.14 (d, 1H, 1.5 Hz), 8.17 (s, 1H), 10.38 (s, 1H, lactam NH), 12.12 (s, 1H, indole NH); $^{13}$C-nmr (DMSO-$d_6$, 100.6MHz): 6(ppm)= 27.2,31.3, 108.4, 112.1, 116.1 (q,$J_{C,F}$=4.1 Hz), 118.5(q,$J_{C,F}$=2.0 Hz), 120.1 (q,$J_{C,F}$=32 Hz), 122.2, 122.6, 125.4 (q, $J_{C,F}$=272 Hz), 125.8, 126.9, 127.0, 128.1, 128.6, 129.7, 134.1, 137.3, 142.2, 171.1, 197.9; $C_{21}H_{15}F_3N_2O_2$ (384.37); Calcd. C 65.6, H 3.9, N 7.3; Found C 65.1, H 4.2, N 7.4.

Example 27

This example describes the synthesis of 2-(3-hydroxy-1-propinyl)-9-trifluoromethyl-7,12-dihydro-indolo[3,2-d][1]benzazepin-6(5H)-one.

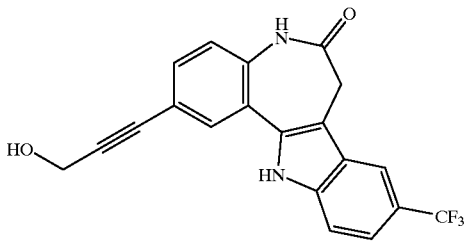

2-iodo-9-trifluoromethyl-7,12-dihydro-indolo[3,2-d][] benzazepin-6(5H)-one (221 mg, 0.5 mmol), propargyl alcohol (112 mg, 2 mmol), bis-(triphenylphosphine)-palladium (II)-dichloride (7 mg, 0.01 mmol), and copper(I) iodide (3.8 mg, 0.02 mmol) were stirred in triethylamine (10 mL) under nitrogen at 50° C. for about 5 hours, until the starting material 2-iodo-9-trifluoromethyl-7, 12-dihydro-indolo[3,2-d][1]benzazepin-6(5H)-one was no longer detectable by thin layer chromatography (silica gel, toluene/acetone 1:1). Acetone (25 mL) was then added. Subsequently, the mixture was filtered and the resulting solution evaporated. The residue was crystallized from ethanol to yield 59% yellow crystals, mp. >330° C.; ir (KBr): 3500–3100 (OH, NH), 1660 (C=O); $^1$H-nmr (DMSO-$d_6$, 400 MHz): δ (ppm)=3.66 (s, 2H, $CH_2$), 4.35 (d, 2H, 6.1 Hz, $CH_2$), 5.39 (t, 1H, 6.1 Hz, OH), 7.26 (d, 1H, 8.2 Hz), 7.45–7.48 (m, 2H), 7.61 (d, 1H, 8.1 Hz), 7.87 (d, 1H, 1.5 Hz), 8.16 (s, 1H), 10.33 (s, 1H, lactam NH), 12.15 (s, 1H, indole NH); $^{13}$C-nmr(DMSO-$d_6$, 100.6 MHz): δ (ppm)=31.3,49.4,82.9,89.8,108.6, 112.2, 116.1 (q,$J_{C,F}$=4.1 Hz), 117.5, 118.5 (q,$J_{C,F}$=3.1 Hz), 120.1 (q,$J_{C,F}$=32 Hz), 122.1, 122.5, 125.4 (q, $H_{C,F}$=271 Hz), 125.8, 129.8, 131.1, 133.7, 135.6, 138.8, 171.2; $C_2OH_{13}F_3N_2O_2$ (370.34); Calcd. C 64.9, H 3.5, N 7.6; Found C 64.5, H 3.8, N 7.3.

Example 28

This example describes the synthesis of 2-[2-(1-hydroxycyclohexyl)-ethinyl]-9-trifluoromethyl-7,12-dihydro-indolo[3,2-d][1]-benzazepin-6(5H)-one.

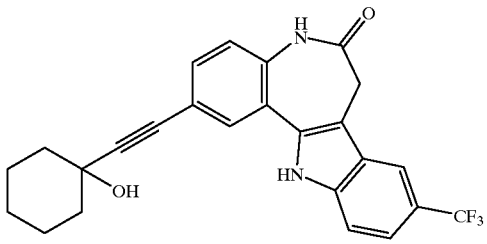

2-iodo-9-trifluoromethyl-7,12-dihydro-indolo[3,2-d][1] benzazepin-6(5H)-one (221 mg, 0.5 mmol), 1-ethinyl-1-cyclohexanol (248 mg, 2 mmol), bis-(triphenylphosphine)-palladium(II)-dichloride (7 mg, 0.01 mmol), and copper(I) iodide (3.8 mg, 0.02 mmol) were stirred in triethylamine (10 mL) under nitrogen at 50° C. for about 1hour, until the starting material 2-iodo-9-trifluoromethyl-7,12-dihydro-indolo[3,2-d][1]benzazepin-6(5H)-one was no longer detectable by thin layer chromatography (silica gel, toluene/ acetone 1:1). Acetone (25 mL) was then added. Subsequently, the mixture was filtered and the resulting solution is evaporated. The residue was crystallized from ethanol to yield 55% colorless crystals, mp.>330° C.; ir (KBr): 3540 (OH), 3280/3180 (NH), 1670 (C=O); $^1$H-nmr (DMSO-$d_6$, 400 MHz): δ (ppm)=1.23–1.28 (m, 1H), 1.51–1.60 (m, 5H), 1.66–1.68 (m, 2H), 1.87–1.90 (m, 2H), 3.64 (s, 2H, $CH_2$), 5.47 (s, 1H, OH), 7.25 (d, 1H, 8.6 Hz), 7.43 (dd, 1H, 8.4/1.8 Hz), 7.47 (dd, 1H, 8.7/1.0 Hz), 7.61 (d, 1H, 8.6 Hz), 7.83 (d, 1H, 2.0 Hz), 8.15 (s, 1H), 10.31 (s, 1H, lactam NH), 12.16 (s, 1H, indole NH); $^{13}$C-nmr (DMSO-$d_6$, 100.6 MHz): δ (ppm)=22.8, 24.9, 31.3, 39.7, 67.0, 82.0, 94.8,108.6,112.1, 116.1 (q, $J_{C,F}$=4.1 Hz), 117.8, 118.5 (q, $J_{C,F}$=3.1 Hz), 120.1 (q, $J_{C,F}$=31 Hz), 122.2, 122.5, 125.4 (q, JCF=272 Hz), 125.7,129.7, 131.1, 133.7, 135.4, 138.8, 171.2; $C_{25}H_{21}F_3N_2O_2$ (438.46); Calcd. C 68.5, H 4.8, N 6.4; Found C 68.1, H 5.0, N 6.3.

Example 29

This example describes the synthesis of 3-(6-oxo-9-trifluoromethyl-5,6,7,12-tetrahydro-indolo[3,2d][1]benzazepin-2-yl)-acrylic acid methyl ester.

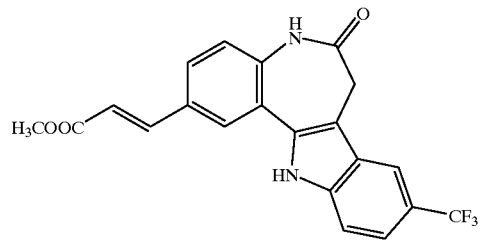

2-iodo-9-trifluoromethyl-7,12-dihydro-indolo[3,2-d][] benzazepin-6(5H)-one (442 mg, 1 mmol), acrylic acid methyl ester (861 mg, 10 mmol), triethylamine (121 mg, 1.2 mmol), palladium(II)-acetate (45 mg, 0.2 mmol), and triphenylphosphine (52 mg, 0.2 mmol) were stirred in N,N-dimethylformamide (30 mL) under nitrogen at 150° C. for about 14 hours, until the starting material 2-iodo-9-trifluoromethyl-7,12-dihydro-indolo[3,2-d][1]benzazepin-6 (5H)-one was no longer detectable by thin layer chromatography (silica gel, toluene/acetone 1:1). The reaction mixture was then filtered hot and the resulting solution evaporated. The residue was crystallized from ethanol/toluene (ethanol may also be used) yielding beige crystals (28%), mp.>330° C.; ir (KBr): 3240 (NH), 1690/1635 (C=O); $^1$H-nmr (DMSO-$d_6$, 400 MHz): δ (ppm) 3.68 (s, 2H, $CH_2$), 3.76 (s, 3H, $OCH_3$), 6.72 (d, 1H, 16.3 Hz), 7.30 (d, 1H, 8.6/1.0 Hz), 7.48 (dd, 1H, 8.6/1.0 Hz), 7.64 (d, 1H, 8.6 Hz), 7.72 (d, 1H, 16.3 Hz), 7.77 (dd, 1H, 8.6/1.5 Hz), 8.14 (d, 1H, 1.5 Hz), 8.17 (s, 1H, arom. H), 10.38 (s, 1H, lactam NH), 12.10 (s, 1H, indole NH); $^{13}$C-nmr (DMSO-$d_6$, 100.6 MHz): δ (ppm)=31.3, 51.4, 108.4, 112.1, 116.1 (q, $J_{C,F}$=3.6 Hz), 117.4, 118.5 (q, $J_{C,F}$=3.6 Hz), 120.1 (q, $J_{C,F}$=33 Hz), 122.1, 122.5, 125.4 (q, $J_{C,F}$=272 Hz), 125.8, 127.0, 128.7, 129.3, 134.1, 137.3, 138.7, 143.5, 166.8, 171.8; $C_{21}H_{15}F_3N_2O_3$ (400.37); Calcd. C 63.0, H 3.8, N 7.0; Found C 62.6, H 3.9, N 7.0.

Example 30

This example describes the synthesis of 2,3-dimethoxy-6-oxo-5, 6, 7,12-tetrahydro-indolo[3,2-d][1]benzazepine-9-carbonitrile.

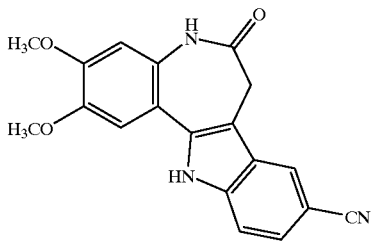

9-bromo-2,3-dimethoxy-7,12-dihydro-indolo[3,2-d][1]benzazepin-6(5h7)-one (387 mg, 1 mmol) and copper(I) cyanide (179 mg, 2 mmol) were refluxed for 2 hours in N-methyl-2-pyrrolidone (10 mL). After cooling to room temperature, water (10 mL) was added and the mixture was stirred for 15 minutes. The precipitate was filtered off with suction and subsequently stirred for 15 minutes in a mixture of water (10 mL) and ethylene diamine (2.5 mL). The precipitate was then filtered off with suction, washed with a 10% solution of sodium cyanide in water and crystallized from ethanol/toluene to furnish 40% of colorless crystals, mp. >330° C.; ir (KBr): 3300/3200 (NH), 2220 (CN), 1660 (C=O); $^1$H-nmr (DMSO-$d_6$, 400 MHz): δ (ppm)=3.53 (s, 2H, $CH_2$), 3.80 (s, 3H, $OCH_3$), 3.87 (s, 3H, $OCH_3$), 6.89 (s, 1H), 7.29 (s, 1H), 7.49 (dd, 1H, 8.6/1.5 Hz), 7.58 (d, 1H, 8.2 Hz), 8.27 (s, 1H), 9.89 (s, 1H, lactam NH), 12.10 (s, 1H, indole NH); $^{13}$C-nmr (DMSO-$d_6$, 100.6 MHz): δ (ppm)= 31.1, 55.5, 55.7, 101.0, 106.0, 106.6, 109.4, 112.3, 113.9, 120.6, 123.4, 124.3, 126.4, 129.7, 135.4, 138.7, 145.3, 149.2, 170.7; $C_{19}H_{15}N_3O_3$ (333.36); Calcd. C 68.5, H 4.5, N 12.6; Found C 68.0, H 4.6, N 12.0.

Example 31

This example describes the synthesis of 2-(2,3-Epoxypropyl)-9-trifluoromethyl-7,12-dihydroindolo[3,2-d][1]benzazepin-6(5H)-one.

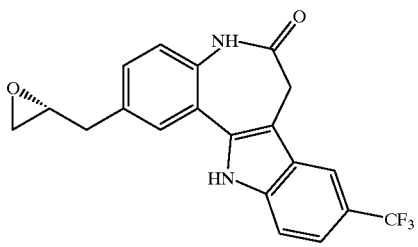

To a suspension of 2-(2-propenyl)-9-trifluoromethyl-7,12-dihydroindolo[3,2-d][1]benzazepin-6(5H)-one (90 mg, 0.25 mmol) and $K_2CO_3$ (100 mg) in MeOH (10 ml) was added 1 ml of MeCN. $H_2O_2$ (35%, 5 ml) was added drop-wise at rt over a period of 3 h. Ice water (50 ml) was added and a while solid precipitated, which was filtered off with suction, washed with water, and purified by column chromatography (ethyl acetate: petrol ether=50:50) to recover 43 mg of 2-(2-propenyl)-9-trifluoromethyl-7,12-dihydroindolo[3,2-d][1]benzazepin-6(5H)-one (48%) and 42 mg of 2-(2,3-Epoxypropyl)-9-trifluoromethyl-7,12-dihydroindolo[3,2-d][1]benzazepin-6(5H)-one (45%): mp295–296° C. (ethanol); IR 3400, 1660, 1500, 1300, 1260, 1100 cmi'; $^1$H NMR (400 MHz) 2.56–2.63 (m, 1 H), 2.77–2.80 (m, 1 H), 2.87 (d, J=5.6 Hz, 2 H), 3.20–3.22 (m, 1 H), 3.60 (s, 2 H), 7.22 (d, J=8.3 Hz, 1 H), 7.33 (d, J=8.1 Hz, 1 H), 7.46 (d, J=8.6 Hz, 1 H), 7.62 (d, J. 8.1 HZ, 1 H), 7.67 (s, 1 H), 8.14 (s, 1 H), 10.12 (s, 1 H), 12.26 (s, 1 H); $^{13}$C NMR(100 MHz) 31.2, 37.5, 46.1, 51.8,108.4, 112.0, 115.8 (q, J=2 Hz), 118.0 (q, J=31 Hz), 118.2 (q, J=2 Hz), 122.1, 122.3, 125.5 (q, J=270 Hz, $CF_3$), 125.8, 127.2, 129.2, 132.9, 134.2, 134.6, 138.7, 171.3; Anal. ($C_2OH_{15}N_2O_2F_3$, 372.342): calcd. C, 64.52; H 4.06; N, 7.52; found C 64.25; H, 4.34; N, 7.49.

Example 32

This example describes the synthesis of 2-(Epoxyethyl)-9-trifluoromethyl-7,12-dihydroindolo[3,2-d][1]benzazepin-6(5H)-one. To a suspension of 2-ethenyl-9-trifluoromethyl-7, 12-dihydroindolo[3,2-d][1]benzazepin-6 (5H)-one (0.25 mmol) and $K_2CO_3$ (100 mg) in MeOH (10 ml) was added 1 ml of MeCN. $H_2O_2$ (35%, 5 ml) was added drop-wise at rt over a period of 3 h. Ice water (50 ml) was added and a while solid precipitated, which was filtered off with suction, washed with water, and purified by column chromatography (ethyl acetate: petrol ether=50:50) to recover 2-(Epoxyethyl)-9-trifluoromethyl-7,12-dihydroindolo[3,2-d][1]benzazepin-6(5H)-one (31%): mp309–310° C. (darkening at 280° C.); IR 3300, 1640, 1300, 1260, 1100 cm$^{-1}$; $^1$HNMR (400 MHz) 2.97 (dd, J=5.1/2.5 Hz, 1 H), 3.19 ("t", J=5.0 Hz, 1 H), 3.62 (s, 2 H), 4.00–4.02 (m 1 H), 7.26 (d, J=8.1 Hz, 1 H), 7.36 (dd, $J_{1\ =8.6}$ Hz, $J_{2=1.5}$ Hz, 1 H), 7.47 (dd, J =8.6 Hz, $J_2$ =1.5 Hz, 1 H), 7.62 (d, J=8.1 Hz, 1 H), 7.68 (d, J. -1.5 Hz, 1 H), 8.20 (s, 1 H), 10.21 (s, 1 H), 12.12 (s, 1 H); $^3$C NMR (125 MHz) 31.2, 50.2, 51.2, 108.5, 112.1, 115.9 (q, J=5 Hz), 118.4 (q, J=2 Hz), 120.0 (q, J=30 Hz), 122.1, 122.4, 124.1, 125.5 (q, J=273 Hz), 125.8, 126.1, 133.0, 134.4, 135.5, 138.7, 171.3; Anal. ($Cl_9H_{13}N_2O_2F_3$, 358.319): calcd. C, 63.69; H 3.66; N, 7.82; found C 62.93; H, 3.75; N, 7.57.

Example 33

This example describes the synthesis of 9—Bromo-2-epoxyethyl-7,12-dihydroindolo[3,2-d][1]benzazepin-6(5H)-one.

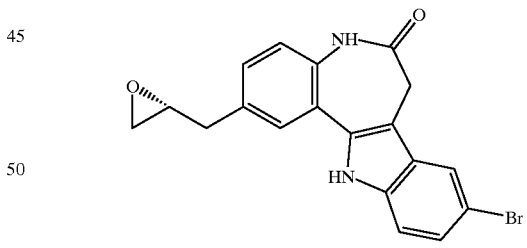

To a suspension of 9-bromo-2-ethenyl-7,12-dihydroindolo [3,2-d][1]benzazepin-6(5H1)-one (80 mg, 0.22 mmol) and $K_2CO_3$ (40 mg) in ethanol (20 ml) was added 2 ml of MeCN. $H_2O_2$ (35% 5 ml) was added drop-wise at rt over a period of 3 h. Ice water (50 ml) was added and a pale yellow solid precipitated, which was filtered off with suction, washed with water, and purified by flash chromatography (ethyl acetate: petrol ether=50:50) recovering 40 mg of 9-bromo-2-ethenyl-7,12-dihydroindolo[3,2-d][1]benzazepin-6(5Th-one (50%) and 32 mg of 9—Bromo-2-epoxyethyl-7,12-dihydroindolo[3,2-d][1]benzazepin-6(5H)-one (38%): mp320–321° C. (darkening at 260° C.); IR 3300, 1640, 1300, 1260, 830 cm$^{-1}$; $^1$H NMR (400 MHz) 2.95 (dd, J=5.6/2.5 Hz, 1 H), 3.17 ("t", J=4.6 Hz, 1 H), 3.49, 3.53 (AB, JAB=14.7 Hz, 2 H), 3.99–4.01 (m, 1 H), 7.24 (d, J=8.6 Hz, 1 H), 7.28 (dd, J,=8.6 Hz, J$_2$=2.0 Hz, 1 H), 7.33 (dd, J=8.6 Hz, J2=2.0 Hz, 1 H), 7.40 (d, J=8.6 Hz, 1 H), 7.64 (d, J=2.0 Hz, 1 H), 7.91 (d, J=2.0 Hz, 1 H), 10.15 (s, 1 H), 11.84 (s, 11H); $^3$C NMR (10 O MHz) 31.3, 50.2, 51.2, 107.3, 111.6, 113.3, 120.4, 122.3, 124.1, 124.6, 125.9, 128.2, 133.0, 133.7, 135.4, 136.0, 171.3; HRMS (Cl$_8$H$_{13}$BrN$_2$O$_2$, 368.0160) found 368.0168

Example 34

This example describes the synthesis of 9—Bromo-2-(2, 3-epoxypropyl-7,12-dihydroindolo[3,2-][1]benzazepin-6 (5H)-one.

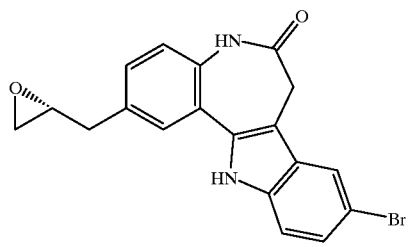

To a suspension of 9-bromo-2-(2-propenyl)-7,12-dihydroindolo[3,2-d][1]benzazepin-6(5H)-one and K$_2$CO$_3$ (40 mg) in ethanol (20 ml) was added 2 ml of MeCN. H$_2$O$_2$ (35%, 5 ml) was added drop-wise at rt over a period of 3 h. Ice water (50 ml) was added and a pale yellow solid precipitated, which was filtered off with suction, washed with water, and purified by flash chromatography (ethyl acetate: petrol ether=50:50) recovering 9-bromo-2-(2-propenyl)-7,12-dihydroindolo[3,2-d][1]benzazepin-6(5H)-one (50%) and 9—Bromo-2-(2,3-epoxypropyl-7,12-dihydroindolo[3,2-ad[1]benzazepin-6(5H)-one (26%): mp308–310° C. (darkening at 260° C.); IR 3200, 1640, 1400, 1300, 12200, 830 cm$^{-1}$; $^1$HNMR (400 MHz) 2.61 (dd, J=4.6/2.5 Hz, 1 H), 2.78 ("t", J=4.1 Hz, 1 H), 2.86 (d,J=5.6 Hz, 2 H), 3.17–3.21 (m 1 H), 3.49 (s, 2 H), 7.19 (d, J =8.1 Hz, 1 H), 7.27 (dd, J,=8.6 Hz, J$_2$ =2.0 Hz, 1 H), 7.30 (dd, J1=8.1 Hz, J2 =2.0 Hz, 1 H), 7.40 (d, J=8.6 Hz, 1 H), 7.63 (s, 1 H), 7.90 (s, 1 H), 10.07 (s, 1 H), 11.80 (s, 1 H); $^{13}$C NMR (100 MHz) 31.3, 37.5, 46.1, 51.8,107.1, 111.6,113.3, 120.3, 122.2, 122.3, 124.4, 127.1, 128.0, 129.0, 132.9, 133.9, 134.1, 135.9, 171.3; Anal. (Cl$_8$H$_{13}$BrN$_2$O$_2$, 383.245): calcd. C, 59.55; H, 3.95; N, 7.31 found C, 59.03; H 4.44; N, 7.21 HRMS calcd. 382.0317 found 382.0322.

Example 35

This example describes the synthesis of 2-(2-oxopropyl)-9-trifluoromethyl-7,12-dihydroindolo[3,2-a][1]benzazepin-6(5H)-one.

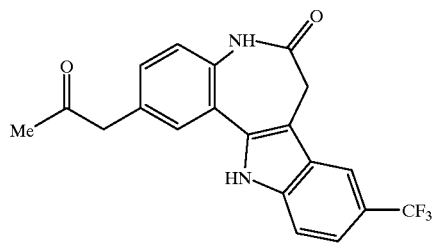

To a solution of $^2$-($^2$-propenyl)-9-trifluoromethyl-7,12-dihydroindolo[3,2-d][1]benzazepin-6(5H)-one (108 mg, 0.3 mmol) in DMF (6 ml) and H20 (1 ml) was added PdCl2 (6 mg, 0.03 mmol) and CuC12 (48 mg, 0.36 mmol). After stirring the mixture overnight at room temperature it was poured into 30 ml of water and extracted with ethyl acetate (50 ml X 3). The organic layers were combined, washed with water (10 ml×3) and dried over NaSO4. Evaporation of the solution yielded a residue, which was purified by flash chromatography (ethyl acetate: petrol ether=70:30) to yield 78 mg of 2-(2-oxopropyl)-9-trifluoromethyl-7,12-dihydroindolo[3,2-d][1]benzazepin-6(5H)-one (69%), mp295–297° C. (ethanol); IR 3310, 1710, 1650, 1310, 800 cm$^{-1}$; $^1$H NMR (400 MHz) 2.20 (s 3 H), 3.58 (s, 2 H), 3.78 (s, 2 H), 7.18–7.30 (m, 2 H), 7.46 (d, J=8.6 Hz, 1 H), 7.57 (s, 1 H), 7.61 (d, J=8.1 Hz, 1 H), 8.13 (s, 1 H), 10.14 (s, 1 H), 12.07 (s, 1 H); $^{13}$C NMR (100 MHz) 29.5, 31.2, 49.9, 108.4, 112.1, 115.8, (q, J. 3 Hz), 118.3 (q 3 Hz), 120.0 (q, J=37 Hz), 122.0, 122.3, 125.5 (q, J=270 Hz), 125.8, 127.8, 130.0, 130.3, 134.3, 134.5, 138.7, 171.3, 205.9; Anal. (C$_2$OH$_{15}$N$_2$O$_2$F$_3$, 372.346): calcd. C, 64.51; H 4.06; N, 7.52; found C 64.30; H, 4.23; N, 7.50

Example 36

This example describes the method used for hollow fiber in vivo testing of mice. Human cancer cells were cultivated in polyvinylidene fluoride (PVDF) hollow fibers. A sample of each cancer cell line was implanted intraperitoneally and subcutaneously in mice. Each mouse received plural fibers, several both intraperitoneally and subcutaneously, representing distinct cancer cell lines. Mice were treated with 9-bromo-7,12-dihydro-indolo[3,2-d][1]benzazepin-6(5H)-one made according to the present invention at each of two test doses intraperitoneally using a QD×4 treatment schedule. Vehicle controls consisted of mice receiving the compound diluent only. The fiber cultures were collected on the day following the last treatment. Anticancer effects were assessed by determining viable cell mass for each of the cell line using a formazan dye (MTT) conversion assay. From this, the % T/C was calculated using the average optical density of the compound-treated samples divided by the average optical density of the vehicle controls. In addition, the net increase in cell mass was determined for each sample as samples of fiber cultures were assessed for viable cell mass on the day of implantation into mice. This allowed cytostatic and cytocidal capacities of these compounds to be assessed.

Example 37

This example describes a method for treating humans with the compounds of the present invention. Compounds satisfying Formulas 1 and/or 2 are obtained. These compounds are then administered orally or intravenously to humans at a dose of from about 30 mg/kg of subject/dose up to about 400 mg/Kg of subject/dose, but preferably between about 30 mg/Kg of subject/dose to about 50 mg/kg of subject/dose, or to provide a total amount of compound or compounds to the subject per treatment of from about 0.1 gram to about 3 grams. Alternatively, compositions comprising one or more compounds satisfying Formula 1 or 2, and at least one material selected from the group consisting of inert carriers, excipients, diagnostics, direct compression binders, buffers, stabilizers, fillers, disintegrants, flavors, colors, lubricants, other active ingredients, other materials conventionally used in the formulation of pharmaceutical compositions, or mixtures thereof, are administered orally or intravenously to humans. The compositions are administered to provide a total amount of compound or compounds to the subject of from about 30 mg/kg of subject/dose up to about 400 mg/Kg of subject/dose, but preferably between about 30 mg/Kg of subject/dose to about 50 mg/kg of subject/dose, or to provide a total amount of compound or compounds to the subject per treatment of from about 0.1 gram to about 3 grams.

The present invention has been described with reference to preferred embodiments. Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A compound according to the formula

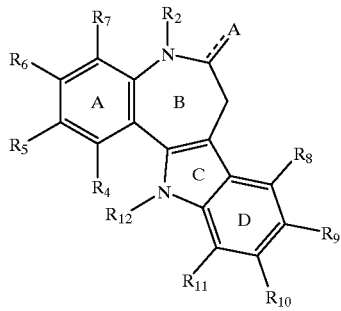

wherein A is a hydroxy, alkoxy, sulfhydryl, or sulfide moiety bonded to ring B by a single bond or is a carbonyl or thiocarbonyl moiety bonded to ring B by a double bond; $R_2$ is selected from the group consisting of hydrogen, aryl, alkoxycarbonylalkyl, alkanoyl, alkoxycarbonyl, alkyl, alkenyl and alkynyl groups; $R_4$–$R_7$ are independently selected from the group consisting of alkoxy, amino, alkanoyl, alkenoyl, alkynoyl, alkyl, alkenyl, alkynyl, cyano, nitro, carboxyl, halogen, hydrogen, hydroxyl, and imino groups; $R_8$–$R_{11}$ are independently selected from the group consisting of alkyl alkoxy, alkenyl alkoxy, alkynyl alkoxy, alkanoyl, alkenoyl, alkynoyl, cyano, nitro, halogen, hydrogen and hydroxyl groups; $R_{12}$ is selected from the group consisting of alkyl, alkenyl, alkynyl, alkoxy, carboxy and hydrogen; and where ring A or D includes a substituent other than hydrogen and halogen.

2. The compound according to claim 1 wherein A is oxygen in a double bond.

3. The compound according to claim 1 wherein $R_2$ is selected from the group consisting of H, —$CH_2COOCH_3$, —$CH_3$, and —$CH_2Ph$.

4. The compound according to claim 1 wherein $R_2$ is hydrogen.

5. The compound according to claim 1 wherein $R_4$–$R_7$ are independently selected from the group consisting of alkoxy, amino, alkanoyl, alkenoyl, alkynoyl, alkyl, alkenyl, alkinyl, aminoalkyl, cyano, nitro, carboxyl, halogen, hydrogen, hydroxyl and imino, lower aliphatic alcohols, lower aliphatic nitriles, and α, β unsaturated ketones.

6. The compound according to claim 1 wherein $R_4$–$R_7$ are independently selected from the group consisting of —H, —OH, —C(=NH)$NH_2$, —$CO_2H$, —Br, —$OCH_3$, cyanoethyl, 3-hydroxy-1-propinyl, 3-oxo-1-butenyl, and 2-(1-hydroxycyclohexyl)-ethinyl.

7. The compound according to claim 1 wherein $R_8$–$R_{11}$ are independently selected from the group consisting of alcohols, alkoxy, alkanoyl, alkenoyl, alkynoyl, alkyl, alkenyl, alkinyl, cyano, nitro, epoxy, haloalkyl, halogen, hydrogen, hydroxyl, lower alkyl, sulfoxide, sulfone, and aminosulfone.

8. The compound according to claim 1 wherein $R_8$–$R_{11}$ are independently selected from the group consisting of -H, halogens, —OH, —$CH_2OH$, —$CH_2CHOCH_2$, —$CH_2CH_2CHOCH_2$, —$CF_3$ and —$OCH_3$.

9. The compound according to claim 1 wherein $R_{12}$ is selected from the group consisting of alcohols, cyano, nitro, carboxylic acids, hydrogen and lower alkyl groups.

10. The compound according to claim 1 wherein $R_{12}$ is selected from the group consisting of —H, —$CH_2CH_2OH$, —$CH_3$ and —$CH_2CH_3$.

11. The compound according to claim 1 selected from the group consisting of 9-bromo-7,12-dihydro-4-methoxy-indolo[3,2-d][1]benzazepin-6(5H)-one; 9-bromo-7,12-dihydro-4-hydroxy-indolo[3,2-d][1]benzazepin-6(5H)-one; 7,12-dihydro-4-methoxy-indolo[3,2-d][1]benzazepin-6(5H)-one; 9-bromo-7,12-dihydro-2,3-dimethoxy-indolo[3,2-d][1]benzazepin-6(5H)-one; 9-bromo-7,12-dihydro-2,3-dihydroxy-indolo[3,2-d][1]benzazepin-6(5H)-one; 7,12-dihydro-2,3-dimethoxy-indolo[3,2-d][1]benzazepin-6(5H)-one; 7,12-dihydro-9-trifluormethyl-indolo[3,2-d][1]benzazepin-6(5H)-one; 7,12-dihydro-2,3-dimethoxy-9-trifluoromethyl-indolo[3,2-d][1]benzazepin-6(5H)-one; 2-bromo-7,12-dihydro-9-trifluoromethyl-indolo[3,2-d][1]benzazepin-6(5H)-one; 9-cyano-7,12-dihydro-indolo[3,2-d][1]benzazepin-6(5H)-one; 9-bromo-7,12-dihydro-12-(2-propenyl)-indolo[3,2-d][1]benzazepin-6(5H)-one; 7,12-dihydro-9-methyl-indolo[3,2-d][1]benzazepin-6(5H)-one; 7,12-dihydro-9-methoxy-indolo[3,2-d][1]benzazepin-6(5H)-one; 9-bromo-7,12-dihydro-2-(methyliminoamine)-indolo[3,2-d][1]benzazepin-6(5H)-one; 9-bromo-7,12-dihydro-2-(carboxylic acid)-indolo[3,2-d][1]benzazepin-6(5H)-one; 9-bromo-7,12-dihydro-10-hydroxy-indolo[3,2-d][1]benzazepin-6(5H)-one; 9-bromo-7,12-dihydro-11-hydroxymethyl-indolo[3,2-d][1]benzazepin-6(5H)-one; 7,12-dihydro-4-hydroxy-indolo[3,2-d][1]benzazepin-6(5H)-one; 7,12-dihydro-2,3-dihydroxy-indolo[3,2-d][1]benzazepin-6(5H)-one; 2,3-dimethoxy-9-nitro-7,12-dihydro-indolo[3,2-d][1]benzazepin-6(5H)-one; 9-cyano-7,12-dihydro-indolo[3,2-d][1]benzazepin-6(5H)-one; 2,3-dimethoxy, 9-cyano-7,12-dihydro-indolo[3,2-d][1]benzazepin-6(5H)-one; 9-nitro-7,12-dihydro-indolo[3,2-d][1]benzazepin-6(5H)-one; 3-(6-oxo-9-trifluoromethyl-5,6,7,12-tetrahydro-indolo[3,2-d][1]benzazepin-2-yl)-propionitrile; 2-bromo-9-nitro-7,12-dihydro-indolo[3,2-d][1]benzazepin-6(5H)-one; 3-(6-oxo-9-trifluoromethyl-5,6,7,12-tetrahydro-indolo[3,2-d][1]benzazepin-2-yl)-acrylonitrile; 2-(3-hydroxy-1-propinyl), 9-trifluoromethyl-7,12-dihydro-indolo[3,2-d][1]benzazepin-6(5H)-one; 2-(3-oxo-1-butenyl), 9-trifluoromethyl-7,12-tetrahydro-indolo[3,2-d][1]benzazepin-6(5H)-one; 2-iodo,9-trifluoromethyl-7,12-dihydro-indolo[3,2-d][1]benzazepin-6(5H)-one; 11-methyl-7,12-dihydro-indolo[3,2-d][1]-benzazepin-6(5H)-one; 2-[2-(1-hydroxycyclohexyl)-ethinyl], 9-trifluoromethyl-7,12-dihydro-indolo[3,2-d][1]benzazepin-6(5N)-one; 2-cyano-7,12-dihydro-indolo[3,2-d][1]benzazepin-6(5H)-one; 11-ethyl-7,12-dihydro-indolo[3,2-d][1]-benzazepin-6(5H)-one; and 3-(6-Oxo-9-trifluoromethyl-5,6,7,12-tetrahydro-indolo[3,2-d][1]-benzazepin-2-yl)-acrylic acid, methyl ester.

12. The compound according to claim 1 selected from the group consisting of 9-cyano-7,12-dihydro-indolo[3,2-d][1]

benzazepin-6(5H)-one; 9-bromo-7,12-dihydro-2,3-dimethoxy-indolo[3,2-d][1]benzazepin-6(5H)-one; 2-bromo-7,12-dihydro-9-trifluoromethyl-indolo[3,2-d][1]benzazepin-6(5H)-one; 7,12-dihydro-2,3-dimethoxy-9-trifluoromethyl-indolo[3,2-d][1]benzazepin-6(5H)-one; 7,12-dihydro-9-trifluormethyl-indolo[3,2-d][1]benzazepin-6(5H)-one; 7,12-dihydro-9-methoxy-indolo[3,2-d][1]benzazepin-6(5H)-one; 9-methyl-7,12-dihydro-indolo[3,2-d][1]benzazepin-6(5H)-one; 9-bromo-7,12-dihydro-2,3-dihydroxy-indolo[3,2-d][1]benzazepin-6(5H)-one; and 7,12-dihydro-2,3-dimethoxyindolo[3,2-d][1]benzazepin-6(5H)-one.

13. The compound according to claim 1 selected from the group consisting of 9-cyano-7,12-dihydro-indolo[3,2-d][1]benzazepin-6(5H)-one; 9-bromo-7,12-dihydro-2,3-dimethoxyindolo[3,2d][1]benzazepin-6(5H)-one; 2-bromo-7,12-dihydro-9-trifluoromethyl-indolo[3,2d][1]benzazepin-6(5H)-one; 7,12-dihydro-2,3-dimethoxy-9-trifluoromethyl-indolo[3,2-d][1]benzazepin-6(5H)-one; 2,9-dibromo-7,12-dihydro-indolo[3,2-d][1]benzazepin-6(5H)-one; 7,12-dihydro-9-trifluormethylindolo[3,2-d][1]benzazepin-6(5H)-one; 7,12-dihydro-9-methoxy-indolo[3,2-d][1]benzazepin-6(5H)-one.

14. The compound according to claim 1 where the compound is 9-nitro-7,12-dihydro-indolo[3,2-d][1]benzazepin-6(5H)-one.

15. A composition comprising an amount of a compound effective to reduce cell proliferation according to the formula

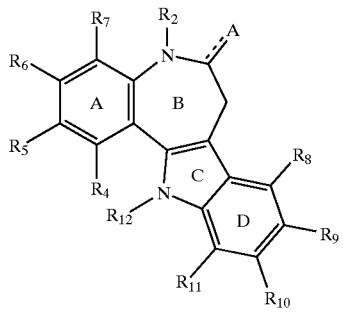

wherein A is a hydroxy, alkoxy, sulfhydryl, or sulfide moiety bonded to ring B by a single bond or is a carbonyl or thiocarbonyl moiety bonded to ring B by a double bond; $R_2$ is selected from the group consisting of hydrogen, aryl, alkoxycarbonylalkyl, alkanoyl, alkoxycarbonyl, alkyl, alkenyl and alkynyl groups; $R_4$–$R_7$ are independently selected from the group consisting of alkoxy, amino, alkanoyl, alkenoyl, alkynoyl, alkyl, alkenyl, alkynyl, cyano, nitro, carboxyl, halogen, hydrogen, hydroxyl, and imino groups; $R_8$–$R_{11}$ are independently selected from the group consisting of alkyl alkoxy, alkenyl alkoxy, alkynyl alkoxy, alkanoyl, alkenoyl, alkynoyl, cyano, nitro, halogen, hydrogen and hydroxyl groups; $R_{12}$ is selected from the group consisting of alkyl, alkenyl, alkynyl, alkoxy, carboxy and hydrogen; and where ring A or D includes a substituent other than hydrogen and halogen.

16. The composition according to claim 15 wherein A is double bonded to oxygen.

17. The composition according to claim 15 wherein $R_2$ is selected from the group consisting of H, —CH$_2$COOCH$_3$, —CH$_3$, and —CH$_2$Ph.

18. The composition according to claim 15 wherein $R_2$ is hydrogen.

19. The composition according to claim 15 wherein $R_4$–$R_7$ are independently selected from the group consisting of alkoxy, amino, alkanoyl, alkenoyl, alkynoyl, alkyl, alkenyl, alkinyl, aminoalkyl, cyano, nitro, carboxyl, halogen, hydrogen, hydroxyl, imino, lower aliphatic alcohols, lower aliphatic nitriles, and α, β unsaturated ketones.

20. The composition according to claim 15 wherein $R_4$–$R_7$ are independently selected from the group consisting of —H, —OH, —C(=NH)NH$_2$, —CO$_2$H, —Br, —OCH$_3$, cyanoethyl, 3-hydroxy-1-propinyl, 3-oxo-1-butenyl, and 2-(1-hydroxycyclohexyl)-ethinyl.

21. The composition according to claim 15 wherein $R_8$–$R_{11}$ are independently selected from the group consisting of alcohols, alkoxy, alkanoyl, alkenoyl, alkynoyl, alkyl, alkenyl, alkinyl, cyano, nitro, epoxy, haloalkyl, halogen, hydrogen, hydroxyl, lower alkyl, sulfoxide, sulfone, and aminosulfone.

22. The composition according to claim 15 wherein $R_8$–$R_{11}$ are independently selected from the group consisting of —H, halogens, —OH, —CH$_2$OH, —CH$_2$CHOCH$_2$, —CH$_2$CH$_2$CHOCH$_2$, —CF$_3$ and —OCH$_3$.

23. The composition according to claim 15 wherein $R_{12}$ is selected from the group consisting of alcohols, carboxylic acids, hydrogen and lower alkyl groups.

24. The composition according to claim 15 wherein $R_{12}$ is selected from the group consisting of —H, —CH$_2$CH$_2$OH, —CH$_3$ and —CH$_2$CH$_3$.

25. The composition according to claim 15 and further comprising inert carriers, excipients, diagnostics, direct compression binders, buffers, stabilizers, fillers, disintegrants, flavors, colors, lubricants, other active ingredients, other materials conventionally used in the formulation of pharmaceutical compositions, and mixtures thereof.

26. A method for treating a subject, comprising: providing a compound effective against a disorder selected from the group consisting of leukemia, lung cancer, central nervous system cancer, melanoma, ovarian cancer, renal cancer, prostate cancer, and breast cancer, the compound having the formula

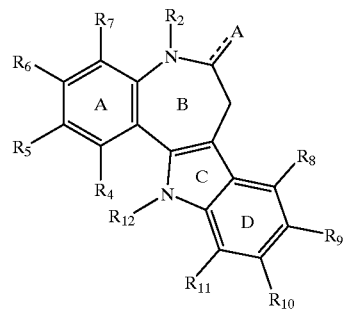

wherein A is a hydroxy, alkoxy, sulfhydryl, or sulfide moiety bonded to ring B by a single bond or is a carbonyl or thiocarbonyl moiety bonded to ring B by a double bond; $R_2$ is selected from the group consisting of hydrogen, aryl, alkoxycarbonylalkyl, alkanoyl, alkoxycarbonyl, alkyl, alkenyl and alkynyl groups; $R_4$–$R_7$ are independently selected from the group consisting of alkoxy, amino, alkanoyl, alkenoyl, alkynoyl, alkyl, alkenyl, alkynyl, cyano, nitro, carboxyl, halogen, hydrogen, hydroxyl, and imino groups; $R_8$–$R_{11}$ are independently selected from the group consisting of alkyl alkoxy, alkenyl alkoxy, alkynyl alkoxy, alkanoyl, alkenoyl, alkynoyl, cyano, nitro, halogen, hydrogen and hydroxyl groups; $R_{12}$ is selected from the group consisting of alkyl, alkenyl, alkynyl, alkoxy, carboxy and hydrogen; and administering the compound to the subject.

27. The method according to claim 26 wherein A is oxygen.

28. The method according to claim 26 wherein $R_2$ is selected from the group consisting of H, —$CH_2COOCH_3$, —$CH_3$, and —$CH_2Ph$.

29. The method according to claim 26 wherein $R_2$ is hydrogen.

30. The method according to claim 26 wherein $R_4$–$R_7$ are independently selected from the group consisting of alkoxy, amino, aminoalkyl, carboxyl, halogen, hydrogen, hydroxyl, imino, lower aliphatic alcohols, lower aliphatic nitrites, and ox, P unsaturated ketones.

31. The method according to claim 26 wherein $R_4$–$R_7$ are independently selected from the group consisting of —H, —OH, —C(=NH)$NH_2$, —$CO_2H$, —Br, —$OCH_3$, cyanoethyl, 3-hydroxy-1-propinyl, 3-oxo-1-butenyl, and 2-(1-hydroxycyclohexyl)-ethinyl.

32. The method according to claim 26 wherein $R_8$–$R_{11}$ are independently selected from the group consisting of alcohols, alkoxies, epoxies, haloalkyl groups, halogen, hydrogen, hydroxyl, lower alkyl groups, sulfoxide, sulfone, and aminosulfone.

33. The method according to claim 26 wherein $R_8$–$R_{11}$ are independently selected from the group consisting of —H, halogens, —OH, —$CH_2OH$, —$CH_2CHOCH_2$, —$CH_2CH_2CHOCH_2$, —$CF_3$ and —$OCH_3$.

34. The method according to claim 26 wherein $R_{12}$ is selected from the group consisting of alcohols, carboxylic acids, hydrogen and lower alkyl groups.

35. The method of according to claim 26 wherein $R_{12}$ is selected from the group consisting of —H, —$CH_2CH_2OH$, —$CH_3$ and —$CH_2CH_3$.

36. The compound according to claim 1 wherein $R_2$ comprises an alkanoyl substituent.

37. The compound according to claim 1 wherein at least one of $R_4$–$R_7$ comprises an α,β unsaturated ketone.

38. The compound according to claim 1 wherein at least one of $R_8$–$R_{11}$ comprises an epoxy group a haloalkyl group, or both.

39. A compound selected from the group consisting of 2,9-dibromo-7,12-dihydro-indolo[3,2-d][1]benzazepin-6(5H)-one; 8,10-dichloro-7,12-dihydro-indolo[3,2-d][1]benzazepin-6(5H)-one; 2-iodo-9-bromo-7,12-dihydro-indolo[3,2-d][1]benzazepin-6(5H)-one; 2-iodo-7,12-dihydro-indolo[3,2-d][1]benzazepin-6(5H)-one; 6-methylthio-7,12-dihydro-indolo[3,2-d][1]benzazepine; 9-bromo-7,12-dihydro-5-methyloxycarbonylmethyl-indolo[3,2-d][1]benzazepin-6(5H)-one; 9-bromo-7,12-dihydro-5-methyl-indolo[3,2-d][1]benzazepin-6(5H)-one; 9-bromo-7,12-dihydro-indolo[3,2-d][1]benzazepin-6(5H)-thione; 9-bromo-5,12-bis-(t-butyloxycarbonyl)-7,12-dihydro-indolo[3,2-d][1]benzazepin-6(5H)-one; 9-bromo-12-(t-butyloxycarbonyl)-7,12-dihydro-indolo[3,2-d][1]benzazepin-6(5H)-one; 9-bromo-5,7-bis-(t-butyloxycarbonyl)-7,12-dihydro-indolo[3,2-cl][1]benzazepin-6(5H)-one; 9-bromo-5,7,12-tri-(t-butyloxycarbonyl)-7,12-dihydro-indolo[3,2-d][1]benzazepin-6(5H)-one; 9-bromo-7,12-dihydro-12-methyloxycarbonylmethyl-indolo[3,2-d][1]bcnzazepin-6(5H)-one; 9-bromo-7,12-dihydro-12-(2-hydroxyethyl)-indolo[3,2-d][1]benzazepin-6(5H)-one; 2,9-dibromo-7,12-dihydro-indolo[3,2-d][1]benzazepin-6(5H)-one; 8,10-dichloro-7,12-dihydro-indolo[3,2-d][1]benzazepin-6(5H)-one; 5-benzyl-9-bromo-7,12-dihydro-5-methyl-indolo[3,2-d][1]benzazepin-6(5H)-one; 9-bromo-7,12-dihydro-12-methyl-indolo[3,2-d][1]benzazepin-6(5H)-one; 9-bromo-12-ethyl-7,12-dihydro-indolo[3,2-d][1]benzazepin-6(5H)-one; 11-bromo-7,12-dihydro-indolo[3,2-d][1]benzazepin-6(5H)-one; 2-iodo-9-bromo-7,12-dihydro-indolo[3,2-d][1]benzazepin-6(5H)-one; 2-iodo-7,12-dihydro-indolo[3,2-d][1]benzazepin-6(5H)-one; and 9-fluoro-7,12-dihydro-indolo[3,2-d][1]benzazepin-6(5H)-one.

* * * * *

UNITED STATES PATENT AND TRADEMARK OFFICE
CERTIFICATE OF CORRECTION

PATENT NO.     : 6,610,684 B2
DATED          : August 26, 2003
INVENTOR(S)    : Zaharevitz et al.

It is certified that error appears in the above-identified patent and that said Letters Patent is hereby corrected as shown below:

Column 1,
Line 63, "p 16" should read -- p16 --.

Column 4,
Line 39, "$R_8$-$R_1$" should read -- $R_8$-$R_{11}$ --.

Column 8,
Line 9, "trifluorynethyl" should read -- trifluormethyl --.
Line 29, "[3,2-d [1]" should read -- [3,2-*d*][1] --.
Line 40, "2-dl[1]" should read -- 2-*d*][1] --.
Lines 45-46, "[3,2-d 1]" should read -- [3,2-*d*][1] --.
Line 48, "[3,2-d1[1]" should read--[3,2-*d*][1] --.
Line 63, "[I]" should read -- [1] --.

Column 9,
Line 2, "d][]" should read -- d][1] --.

Column 14,
Line 19, "PCTIUS99" should read -- PCT/US99 --.

Column 16,
Line 7, "IC50's" should read -- $IC_{50's}$ --.
Line 14, "[3,24d][1]" should read -- [3,2-*d*][1] --.
Line 20, "[3,2-dj [1]" should read -- [3,2-*d*][1] --.
Line 32, "[3,2-4[1]" should read -- [3,2-*d*][1] --.
Line 41, "6(5H-one" should read -- 6(5*H*)-one --.

Column 17,
Line 5, "$IC_{50}S$" should read -- $IC_{50's}$ --.
Line 22, "[3,2-][lI]" should read -- [3,2-*d*][1] --.
Line 25, "[I]" should read -- [1] --.
Line 27, "[3, 2-4]" should read -- [3,2-*d*] --.
Line 37, "1-1" should read -- 11 --.

Column 18,
Line 43, "Cancel" should read -- cancer --.

Column 19,
Line 47, "6(514)" should read -- 6(5H) --.
Line 51, "(RCT-116" should read -- (HCT-116) --.

UNITED STATES PATENT AND TRADEMARK OFFICE
CERTIFICATE OF CORRECTION

PATENT NO. : 6,610,684 B2
DATED : August 26, 2003
INVENTOR(S) : Zaharevitz et al.

It is certified that error appears in the above-identified patent and that said Letters Patent is hereby corrected as shown below:

Column 20,
Line 19, "IH-[I]" should read -- 1H-[1] --.

Column 21,
Line 55, "$C_{16}H$," should read -- $C_{16}H_{11}$ --.

Column 22,
Line 8, "6 (ppm)" should read -- δ (ppm) --.
Line 10, "$C_{17}HIIN_3O$" should read -- $C_{17}H_{11}N_3O$ --.

Column 23,
Line 2, "o (ppm)" should read -- δ (ppm) --.
Line 11, "[]]" should read -- [1] --.
Line 66, "$C_{16}H]IFN_2O$" should read -- $C_{16}H_{11}FN_2O$ --.

Column 24,
Line 22, "Immol)" should read -- 1 mmol) --.
Line 29, "$^3$C-nmr" should read -- $^{13}$C-nmr --.
Line 59, "o (ppm)" should read -- δ (ppm) --.
Line 62, "6 (ppm)" should read -- δ (ppm) --.

Column 25,
Line 21, "4H1)" should read -- 4H) --.
Line 25, "5 (ppm)" should read -- δ (ppm) --.
Line 28, "$^1$C-" should read -- $^{13}$C- --.
Line 29, "68 (ppm)" should read -- δ (ppm) --.
Line 32, "$Cl_9$" should read -- $C_{19}$ --.
Line 65, "$H_1O$" should read -- $H_{10}$ --.

Column 26,
Line 20, "[11]" should read -- [1] --.
Line 21, "(5H1" should read -- (5H) --.
Line 40, "$Cl_9$" should read -- $C^{19}$ --.

Column 28,
Line 13, "13C" should read -- $^{13}$C --.
Line 18, "-hromo-" should read -- bromo- --.
Line 45, "11H" should read -- 1H --.
Line 50, "$N_{20}S$" should read -- $N_2OS$ --.

UNITED STATES PATENT AND TRADEMARK OFFICE
CERTIFICATE OF CORRECTION

PATENT NO. : 6,610,684 B2
DATED : August 26, 2003
INVENTOR(S) : Zaharevitz et al.

It is certified that error appears in the above-identified patent and that said Letters Patent is hereby corrected as shown below:

Column 30,
Line 25, "]H" should read -- 1H --.

Column 31,
Line 17, "C]$_8$H18N$_4$O$_5$" should read -- $C_{18}H_{18}N_4O_5$ --.

Column 32,
Line 5, "$C_{13}HI_4INO_5$" should read -- $C_{13}N_{14}N_4INO_5$ --.
Line 11, "dimethylfornamide" should read -- dimethylformamide --.
Lines 23-24, "-JH-[]]henzazepine-" should read -- 1H[1]benzazepine --.
Line 29, "(ppm) 30.6" should read -- (ppm)=30.6 --.
Line 31, "134.4" should read -- I 34.4 --.
Line 50, "CIoH$_8$INO$_2$" should read -- $C_{10}H_8N_4INO_2$ --.

Column 33,
Line 1, "JCF (2 times)" should read -- $J_{C,F}$ (2 times) --.
Line 3, "N$_{20}$" should read -- $N_2O$ --.
Line 23, "(5H1)-one" should read -- (5H)-one --.
Line 28, "11H" should read -- 1H --.
Line 43, "JCF" should read -- $J_{C,F}$ --.
Line 46, "C$_2$OH$_{12}$..." should read -- $C_{20}H_{12}$... --.

Column 34,
Line 20, "$C_{20}H_4F_3N_{30}$" should read -- $C_{20}H_{14}F_4N_3O$ --.

Column 35,
Line 18, "[ ]" should read -- [1] --.
Line 38, "$H_{C,F}$" should read -- $J_{C,F}$ --.
Line 39, "C$_2$OH$_{13}$" should read -- $C_{20}H_{13}$ --.
Line 64, "I hour" should read -- 1 hour --.

Column 37,
Line 19, "(5h7)" should read -- (5H) --.

Column 38,
Line 1, "1100 cmi$^1$" should read -- 1100 cm$^{-1}$ --.
Line 10, "C$_2$OH$_{15}$" should read -- $C_{20}H_{15}$ --.
Line 30, "J=8.6 Hz" should read -- $J_1$=8.6 Hz --.
Line 36, "(CL$_9$H$_{13}$..." should read -- ($C_{19}H_{13}$… --.
Line 56, "(5H1)" should read -- (5H) --.

UNITED STATES PATENT AND TRADEMARK OFFICE
CERTIFICATE OF CORRECTION

PATENT NO. : 6,610,684 B2
DATED : August 26, 2003
INVENTOR(S) : Zaharevitz et al.

It is certified that error appears in the above-identified patent and that said Letters Patent is hereby corrected as shown below:

Column 39,
Line 2, "JAB" should read -- $J_{AB}$ --.
Line 3, "J,=8.6 Hz, J2=2.0 Hz" should read -- $J_1$=8.6 Hz, $J_2$=2.0 Hz --.
Line 6, "11H" should read -- 1H --.
Line 6, "(10 O MHz)" should read -- (100 MHz) --.
Line 8, "($CL_8H_{13}$..." should read -- ($C_{18}H_{13}$... --.
Line 13, "[3,2-]" should read -- [3,2-d] --.
Line 36, "[3,2-ad[l]" should read -- [3,2-d][1] --.
Line 52, "[3,2-a]" should read -- [3,2-d] --.
Line 66, "$^2$-($^2$-propenyl)" should read -- 2-(2-propenyl) --.

Column 40
Line 16, "J. 3 Hz)" should read -- J=3 Hz --.
Line 16, "q 3 Hz" should read -- q = 3 Hz --.
Line 19, "$C_2OH_{15}$..." should read -- $C_{20}H_{15}$... --.

Column 42,
Line 35, "(5H)-one; 9-bromo-7," should read -- (5H)-one; 9-fluoro-7,12-dihydro-12-(2-propenyl)-indolo[3,2-d][1]benzazepin-6(5H)-one; 9-bromo-7, --.
Line 57, "benzazepin-6(5H)-one; 11-methyl-7," should read -- -benzazepin-6(5H)-one; 7,12-dihydro-pyrido[3',c2':4,5]pyrrolo[3,2-d][1]benzazepin-6(5H)-one; 11-methyl-7, --.
Line 61, "(5N)" should read -- (5H) --.

Column 43,
Line 9, "(5H)-one; 9-bromo-7," should read -- (5H)-one; 9-bromo-7,12-dihydro-12-(2-hydroxyethyl)-indolo[3,2-*d*][1]benzazepin-6(5H)-one; 9-bromo-7, --.
Line 11, "dimethoxyindolo" should read -- dimethoxy-indolo --.
Line 12, "(5H)-one." should read -- (5H)-one; 9-bromo-7,12-dihydro-12-mehtyl-indolo[3,2-*d*][1]benzazepin-6(5H)-one. --.
Line 16, "[3,2d]" should read -- [3,2-*d*] --.
Line 21, "trifluormethylindolo" should read -- trifluromethyl-indolo --.

Column 45,
Line 16, "ox, P unsaturated" should read -- α, β unsaturated --.

UNITED STATES PATENT AND TRADEMARK OFFICE
CERTIFICATE OF CORRECTION

PATENT NO. : 6,610,684 B2
DATED : August 26, 2003
INVENTOR(S) : Zaharevitz et al.

It is certified that error appears in the above-identified patent and that said Letters Patent is hereby corrected as shown below:

<u>Column 46,</u>
Line 36, "...benzazepin-6(5H)-one; and..." should read -- ...benzazepin-6(5H)-one; 9-chloro-7,12-dihydro-indolo[3,2-*d*][1]benzazepin-6(5H)-one; 10-bromo-7,12-dihydro-indolo[3,2-*d*][1]benzazepin-6(5H)-one; 9-fluoro-7,12-dihydro-indolo[3,2-*d*][1]benzazepin-6(5H)-one; 2-bromo-7,12-dihydro-indolo[3,2-*d*][1]benzazepin-6(5H)-one; and 7, 12-dihydro-indolo[3,2-*d*][1]benzazepin-6(5H)-one. --.

Signed and Sealed this

Twenty-sixth Day of July, 2005

JON W. DUDAS
*Director of the United States Patent and Trademark Office*